US012747227B2

(12) United States Patent
Hodgetts et al.

(10) Patent No.: US 12,747,227 B2
(45) Date of Patent: *Sep. 29, 2026

(54) EAAT2 ACTIVATORS AND METHODS OF USING THEREOF

(71) Applicants: OHIO STATE INNOVATION FOUNDATION, Columbus, OH (US); THE BRIGHAM AND WOMEN'S HOSPITAL, INC., Boston, MA (US)

(72) Inventors: Kevin Hodgetts, Boston, MA (US); Chien-Liang Glenn Lin, Columbus, OH (US)

(73) Assignees: OHIO STATE INNOVATION FOUNDATION;, Columbus, OH (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/354,330

(22) Filed: Jul. 18, 2023

(65) Prior Publication Data

US 2024/0208936 A1 Jun. 27, 2024

Related U.S. Application Data

(63) Continuation of application No. 17/959,654, filed on Oct. 4, 2022, now Pat. No. 12,286,420, which is a continuation of application No. 16/972,311, filed as application No. PCT/US2019/035452 on Jun. 4, 2019, now Pat. No. 11,702,403.

(60) Provisional application No. 62/680,418, filed on Jun. 4, 2018, provisional application No. 62/680,423, filed on Jun. 4, 2018.

(51) Int. Cl.

| | |
|---|---|
| ***C07D 401/14*** | (2006.01) |
| ***A61P 25/22*** | (2006.01) |
| ***A61P 25/24*** | (2006.01) |
| ***A61P 25/28*** | (2006.01) |
| ***C07D 237/14*** | (2006.01) |
| ***C07D 401/04*** | (2006.01) |
| ***C07D 413/14*** | (2006.01) |

(52) U.S. Cl.

CPC ............ *C07D 401/14* (2013.01); *A61P 25/22* (2018.01); *A61P 25/24* (2018.01); *A61P 25/28* (2018.01); *C07D 237/14* (2013.01); *C07D 401/04* (2013.01); *C07D 413/14* (2013.01)

(58) Field of Classification Search

CPC .. C07D 401/14; C07D 401/04; C07D 413/14; C07D 237/14

USPC ...................................................... 514/236.5

See application file for complete search history.

(56) References Cited

FOREIGN PATENT DOCUMENTS

| | | | | | |
|---|---|---|---|---|---|
| WO | WO-03004494 | A1 * | 1/2003 | .............. | A61P 25/00 |
| WO | WO-2008103277 | A2 * | 8/2008 | ................ | A61P 9/10 |
| WO | WO-2014121931 | A1 * | 8/2014 | ................ | A61P 3/10 |
| WO | WO-2017028798 | A1 * | 2/2017 | ......... | C07D 491/048 |

OTHER PUBLICATIONS

Journal of Organic Chemistry (1963), 28(7), 1919-21.*

* cited by examiner

*Primary Examiner* — Kahsay Habte

(74) *Attorney, Agent, or Firm* — Meunier Carlin & Curfman LLC

(57) ABSTRACT

Disclosed are compounds that activate excitatory amino acid transporter 2 (EAAT2), as well as methods of using these compounds to treat or preventing diseases, disorders, and conditions associated with glutamate excitotoxicity.

4 Claims, 22 Drawing Sheets

EAAT2 ACTIVATORS AND METHODS OF USING THEREOF

CROSS-REFERENCE TO RELATED APPLICATIONS

This application is a continuation of U.S. patent application Ser. No. 17/959,654 filed Oct. 4, 2022, issued as U.S. Pat. No. 12,286,420 on Apr. 29, 2025, which is a continuation of U.S. patent application Ser. No. 16/972,311 filed Dec. 4, 2020, issued as U.S. Pat. No. 11,702,403 on Jul. 18, 2023, which is a national stage entry under 35 U.S.C. § 371 of International Patent Application No. PCT/US2019/035452, filed Jun. 4, 2019, which claims benefit of U.S. Provisional Application No. 62/680,418, filed Jun. 4, 2018, and U.S. Provisional Application No. 62/680,423, filed Jun. 4, 2018, each of which is hereby incorporated herein by reference in its entirety.

STATEMENT REGARDING FEDERALLY SPONSORED RESEARCH OR DEVELOPMENT

This invention was made with Government Support under Grant No. U01AG054444 awarded by the National Institutes on Aging, a division of the National Institutes of Health. The Government has certain rights in the invention.

TECHNICAL FIELD

This application relates generally to compounds that increase expression of excitatory amino acid transporter 2 (EAAT2), and methods of use thereof for treating or preventing diseases, disorders, and conditions associated with glutamate excitotoxicity.

BACKGROUND

Glutamate is a major neurotransmitter in the mammalian central nervous system (CNS) and essential for normal brain function including cognition, memory, and learning. However, the extracellular concentration of glutamate must remain below excitotoxic levels (~1 μM) to avoid overstimulation of glutamate receptors, leading to neuronal damage or death (Sheldon and Robinson, Neurochem. Int. 2007, 51, 333). Excitotoxicity has been associated with multiple acute neurological conditions such as ischemic stroke, epilepsy, and trauma, chronic adult-onset neurodegenerative disorders such as Alzheimer's disease and amyotrophic lateral sclerosis (ALS) (Guo et al., Hum. Mol. Genet. 2003, 12, 2519; Tian et al., J. Biol. Chem. 2007, 282, 1727; Hazell, Neurochem. Int. 2007 50, 941; Seifert et al., Brain. Res. Rev. 2010, 63, 212; Tian et al., J. Neurochem. 2010, 113, 978), and depression. One potential approach to preventing excitotoxicity is to enhance glutamate reuptake. EAAT2 is the major glutamate transporter and functions to remove glutamate from synapses (Lin et al., Am. J. Physiol. Gastrointest Liver Physiol. 2009, 296, 129). An increase in EAAT2 protein expression and function can provide a means to prevent insufficient glutamate reuptake and consequently reduce neuronal damage.

SUMMARY

Provided herein are compounds defined by Formula I

Formula I

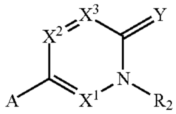

wherein

Y is O, S, or $NR^1$;

$X^1$ is CH or N;

$X^2$ is $CR^3$ or N;

$X^3$ is $CR^4$ or N;

A is selected from the group consisting of 6-10 membered aryl and 5-10 membered heteroaryl, each of which is optionally substituted by 1, 2, 3, or 4 independently selected $R^A$ groups;

$R^1$ is selected from H and $C_{1-6}$ alkyl;

$R^2$ is $-(CR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^CR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^CR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, A can be phenyl, which can be unsubstituted or substituted by 1, 2, 3, or 4 independently selected $R^A$ groups. In other embodiments, A can be a 5-10 membered heteroaryl, which can be unsubstituted or substituted by 1, 2, 3, or 4 independently selected $R^A$ groups. In certain embodiments, A can be an unsubstituted 5-6 membered heteroaryl. In certain embodiments, A can be unsubstituted pyridyl. In certain embodiments, A can be selected from the group consisting of unsubstituted 2-pyridyl and unsubstituted 3-pyridyl.

In some embodiments, Y can be O.

In some embodiments, one of $X^1$, $X^2$, and $X^3$ is N. For example, in some embodiments, $X^1$ is N, $X^2$ is $CR^3$, and $X^3$ is $CR^4$. In other embodiments, $X^1$ is CH, $X^2$ is N, and $X^3$ is $CR^4$.

In some embodiments, $R^3$, when present, is H.

In some embodiments, $R^4$, when present, is H.

In some embodiments, the compound can be defined by Formula II

Formula II

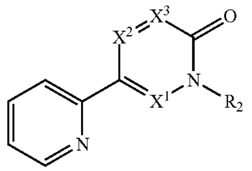

wherein $X^1$ is CH orN;

$X^2$ is $CR^3$ or N;

$X^3$ is $CR^4$ or N;

$R^2$ is $—(CHR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NRW)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, the compound can be defined by Formula IIA

Formula IIA

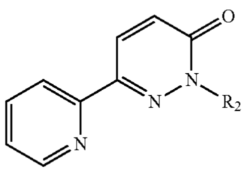

wherein $R^2$ is —$(CR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^CR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, the compound can be defined by Formula IIB

Formula IIB

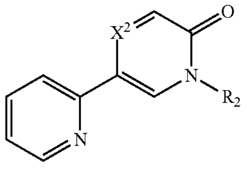

wherein $R^2$ is —$(CHR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^CR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)$ $NR^cR^d$, $NR^cC(=NRW)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^CR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups; $R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, the compound can be defined by Formula III

Formula III

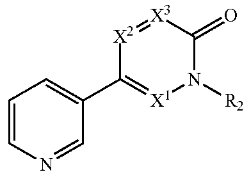

wherein $X^1$ is CH orN;

$X^2$ is $CR^3$ or N;

$X^3$ is $CR^4$ or N;

$R^2$ is —$(CR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^CR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NRW)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^CR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, the compound can be defined by Formula IIIA

Formula IIIA

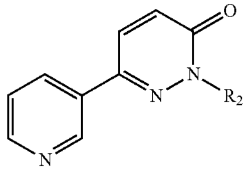

wherein $R^2$ is —$(CHR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^CR^d$, $C(O)OR^a$, $OC(O)R^b$, $OC(O)NR^cR^d$, $NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NRW)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, the compound can be defined by Formula IIIB

Formula IIIB

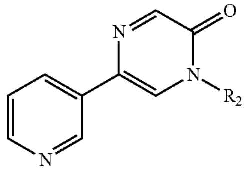

wherein $R^2$ is —$(CR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NRW)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, $R^2$ can be selected from the group consisting of $—(CH_2)_nR^5$, $—(CH(CH_3))_nR^5$, and $—(CH_2CH(NH_2))_nR^5$.

In some embodiments, $R^5$ can be selected from the group consisting of $OR^C$, $NR^CR^D$, $C(O)NR^CR^D$, $C_{6-10}$ aryl, $C_{3-10}$ cycloalkyl, 4-10 membered heterocycloalkyl, and 5-10 membered heteroaryl, wherein the $C_{6-10}$ aryl, $C_{3-10}$ cycloalkyl, 4-10 membered heterocycloalkyl, and 5-10 membered heteroaryl are each optionally substituted by 1, 2, 3, or 4 independently selected $R^B$ groups.

In some embodiments, $R^5$ can be selected from the group consisting of $OR^C$, $NR^CR^D$, $C(O)NR^cR^D$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups. In certain embodiments, $R^5$ can be selected from the group consisting of $OR^C$, $NR^CR^D$, $C(O)NR^cR^D$, phenyl, $C_{3-6}$ cycloalkyl, 4-6 membered heterocycloalkyl, and 5-6 membered heteroaryl, wherein the phenyl, 4-6 membered heterocycloalkyl, and 5-6 membered heteroaryl are each optionally substituted by 1 or 2 independently selected $R^B$ groups.

In some embodiments, $R^5$ can be selected from the group consisting of $OCH_3$, $N(CH_3)_2$, $C(O)N(CH_3)_2$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups. In certain embodiments, $R^5$ can be selected from the group consisting of $OCH_3$, $N(CH_3)_2$, $C(O)N(CH_3)_2$, phenyl, $C_{3-6}$ cycloalkyl, 4-6 membered heterocycloalkyl, and 5-6 membered heteroaryl, wherein the phenyl, 4-6 membered heterocycloalkyl, and 5-6 membered heteroaryl are each optionally substituted by 1 or 2 independently selected $R^B$ groups.

In some embodiments, $R^C$ and $R^D$, when present, can be independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-6 membered heteroaryl, 4-6 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-6 membered heteroaryl, 4-6 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups.

In some embodiments, each $R^B$, when present, can be independently selected from the group consisting of $C_{1-6}$ alkyl and $NR^cR^d$. In certain embodiments, each $R^B$, when present, can be independently selected from the group consisting of $C_{1-3}$ alkyl and $N(C_{1-3}$ alkyl$)_2$.

In some embodiments, n can be 0, 1, or 2.

Also provided herein are pharmaceutical compositions comprising a compound described herein and a pharmaceutically acceptable excipient.

Also provided herein are methods for treating or preventing glutamate excitotoxicity in a subject in need thereof.

These methods can comprise administering to the subject an effective amount of a compound provided herein.

Further provided herein are methods for increasing EAAT2 protein expression in a cell or a subject in need thereof. These methods can comprise contacting the cell or administering to the subject an effective amount of a compound provided herein.

Further provided herein are methods for activating the NRF2 pathway in a cell or a subject in need thereof. These methods can comprise contacting the cell or administering to the subject an effective amount of a compound provided herein.

Also provided herein are methods for treating a disease or disorder selected from the group consisting of ischemic stroke, epilepsy, or a trauma, including blunt trauma, an abrasion, an avulsion, an incision, a laceration, a puncture, a penetration, a surgical trauma, iatrogenic trauma, a spinal cord injury, a traumatic brain injury, or any combination thereof; a chronic neurodegenerative disorder, including mild cognitive impairment, Parkinson's disease, Alzheimer's disease, multiple sclerosis, mesial temporal sclerosis, Huntington's disease, AIDS dementia complex, essential tremor, or amyotrophic lateral sclerosis (ALS); a psychotic disorder including schizophrenia, bipolar disorder, or autism; a pain disorder including migraine, temporomandibular disorders, neuropathic pain, visceral pain, or complex regional pain syndrome; an addiction including alcohol addiction, cocaine addiction, heroin addiction, methamphetamine addiction, or nicotine addiction; or a cancer, including glioblastoma; or a mood disorder, including anxiety disorders, depressive disorders, borderline personality disorder, attention-deficit-hyperactivity disorder, suicidal behavior, eating disorders, posttraumatic stress disorder, gulf war illness, and obsessive-Compulsive Disorder in a subject in need thereof. These methods can comprise administering to the subject an effective amount of a compound provided herein, or a pharmaceutically acceptable salt thereof.

DESCRIPTION OF DRAWINGS

FIG. 2A: Western blots show dose-dependent increase of EAAT2 protein levels. FIG. 2B: Time-dependent fold increase in EAAT2 protein expression in response to compound treatment at 4 hours (1.54±0.13) and 24 hours (1.98±0.19) post-treatment. Quantification of EAAT2 expression time course (normalized to flotilin; n=4/group). Data represented as mean±SEM and analyzed using one-way ANOVA with Tukey post-hoc test. *p<0.05, p<0.01. FIG. 2C: Compound treatment enhances CA3-CA1 LTP in the hippocampus. Mice were treated with vehicle or compound for seven days and acute hippocampal sections were collected for LTP recordings. Compound treated animals (10 slices, 4 animals) exhibit increased CA1 field potential response after CA3 afferent theta-burst stimulation (TBS) compared to control animals (11 slices, 4 animals). Data represented as mean±SEM analyzed using one-way ANOVA with Bonferroni post-hoc tests. Statistical significance denoted as *p<0.001.

FIGS. 4A-4D show the results of a behavioral battery (n=27/27/23/27 respectively). Compound treatment normalized hyperactivity in the open field (FIG. 4A), short-term memory in the Y-maze (FIG. 4B), recognition memory in the novel object recognition (FIG. 4C) and cognition in the T-maze (FIG. 4D). As shown in FIG. 4E, PSD-95 expression in hippocampal postsynaptic densities of rTg4510 was significantly reduced (n=5/5/4/4 respectively), showing synaptic loss. Compound 100 treatment in rTg4510 mice restored synaptic integrity. As showed in FIG. 4F, hippocampal crude membrane preparations (n=5/5/4/4 respectively) revealed increased EAAT2 in the rTg4510 vehicle group which was partially normalized by compound treatment. FIG. 4G shows representative immunohistochemistry images of hippocampal sub-regions (n=4 animals/group; average of ≥3 sections/animal). Cell nuclei were stained by DAPI. Quantification (right) is percent change relative to control vehicle (dashed line), except MC1 (compared to rTg4510 vehicle). Control groups exhibited no differences. NeuN immunostaining demonstrated significant neurodegeneration in CA1 and DG of rTg4510 mice, which was prevented by compound-treatment. Compound-treatment maintained CA3 synaptic integrity (synaptophysin) and significantly reduced neurofibrillary tangle accumulation (MC1) in CA1 of rTg4510 mice. Finally, GFAP immunoreactivity was significantly increased in both rTg4510 groups, but compound treatment reduced gliosis. Scale bar=100 m. *P<0.05, P<0.01, *P<0.001.

FIGS. 5A-5E show the results of a behavioral battery (n=34/21/28/32 respectively). Long-term compound-treatment continued to prevent development of agitation-like behavior (FIG. 5A) while maintaining improved cognition in Y-maze (FIG. 5B) recognition memory in the novel object recognition (FIG. 5C) and spatial memory in Barnes Maze (FIG. 5D, FIG. 5E) in rTg4510 mice. As shown in FIG. 5F, loss of PSD-95 in rTg4510 hippocampal postsynaptic densities was robust (n=8/group); compound-treatment continued to significantly reduce synaptodegeneration. FIGS. 5G and 5H show PFC tripartite-synapse integrity (n=4/group). Similar to the hippocampus at four-months, rTg4510 PFC postsynaptic densities exhibit increased crude membrane EAAT2 expression (FIG. 5G) and decreased PSD-95 expression (FIG. 5H). Compound 100 treatment partially normalized both phenotypes. FIG. 5I show representative immunohistochemistry images of the hippocampus (n=4/group). Cell nuclei were stained by DAPI. Quantification (right) is percent change relative to control vehicles (dashed line). Neurodegeneration (as assessed by NeuN) was observed in CA1 and DG of rTg4510 vehicle mice; however, compound-treatment significantly reduced neuronal loss. A similar pattern was observed for synaptic integrity (synaptophysin). rTg4510 mice exhibit increased GFAP and Ibal in CA1, which was reduced and partially normalized by compound treatment. Scale bar=100 m. *P<0.05,P<0.01, *P<0.001.

As shown in FIG. 6C, PSD-95 protein expression in hippocampal postsynaptic densities of rTg4510 mice continued to remain significantly higher in the treatment STOP group compared to the vehicle group. FIGS. 6D and 6E show hippocampal functional connectivity in the CA3-CA1 circuit along the Schaffer collateral pathway (n=4/11; 4/17, 3/10; 4/14; and 2/9 respectively). FIG. 6D show input/output curves for all five groups of mice. All rTg4510 mice exhibit reduced synaptic strength compared to controls. However, both compound cessation and continuation groups show enhanced synaptic strength compared to rTg4510 vehicle mice. FIG. 6E show vehicle-treated rTg4510 mice displayed significantly reduced LTP, while compound treatment cessation and continuation groups displayed LTP that was indistinguishable from control vehicle mice. Of note, compound-treated controls displayed significantly increased LTP relative to control vehicles. TBS, theta-burst stimulation. *P<0.05, P<0.01, *P<0.001.

FIGS. 7A and 7B illustrate the effect of compound treatment on phosphorylated tau in total lysates (TCL) and in the Sarkosyl insoluble (P3) fraction (n=4/group). Dashed-line represents expression in rTg4510 vehicle group. As shown in FIG. 7A, long-term Compound 100 treatment reduced phosphorylated (AT8 and PHF1) as well as confirmation specific (MC1) forms of tau. There was a very significant reduction of total tau in the P3 fraction and subsequent reductions of phospho-tau expression. As shown in FIG. 7B, single dosing of compound significantly reduced tau phosphorylation. As shown in FIG. 7C, treatment with Compound 100 significantly increased phosphorylation of GSK30 at Ser9 in rTg4510 mice approximately 2-fold within one hour of treatment (n=4/group). *P<0.05, P<0.01, *P<0.001.

DETAILED DESCRIPTION

Figure 1A:
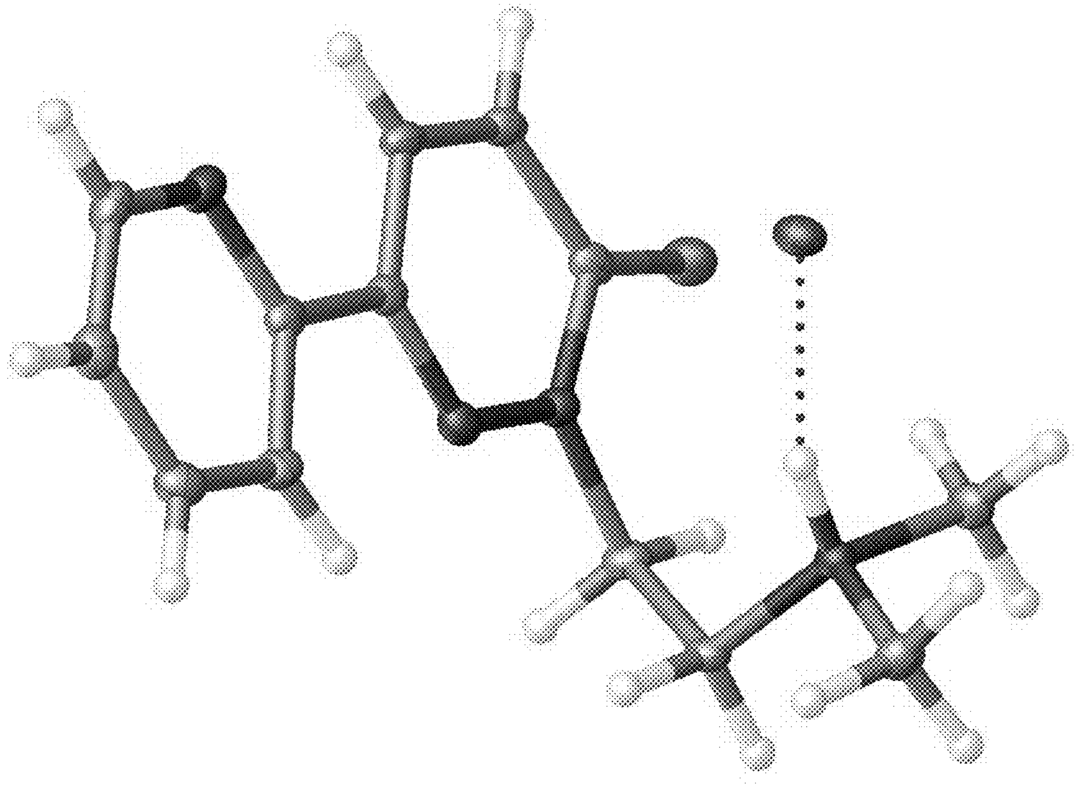
FIG. 1A shows the crystal structure of Compound 100.

The compounds provided herein may be useful for activating EAAT2, and thus useful in methods of reducing extracellular glutamate levels, thereby reducing glutamate excitotoxicity in cells and tissues, making the compounds therapeutically useful in treating or preventing conditions associated with glutamate excitotoxicity (e.g., acute neurological conditions such as ischemic stroke, epilepsy, and trauma, as well as chronic adult-onset neurodegenerative disorders such as Alzheimer's disease and amyotrophic lateral sclerosis (ALS)). In some embodiments, the compounds provided herein may be therapeutically useful in treating or preventing depression.

Definitions

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

At various places in the present specification, divalent linking substituents are described. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —$NHS(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —$S(O)_2NH_2$.

As used herein, the term "$C_{n-m}$ alkylaminosulfonyl" refers to a group of formula —$S(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —$S(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —$NHS(O)_2NH_2$.

As used herein, the term "$C_{n-m}$ alkylaminosulfonylamino" refers to a group of formula —$NHS(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —$NHS(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —$NHC(O)NH_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —$NHC(O)N(alkyl)_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —$S(O)_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —$NH_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, the term "carbamyl" to a group of formula —$C(O)NH_2$.

As used herein, the term "carbonyl", employed alone or in combination with other terms, refers to a —C(═O)— group, which may also be written as C(O).

As used herein, the term "di($C_{n-m}$-alkyl)amino" refers to a group of formula —$N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —$C(O)N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "halo" refers to F, Cl, Br, or I. In some embodiments, a halo is F, Cl, or Br. In some embodiments, a halo is F or Cl.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms.

In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membereted heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H—, 2H— and 4H—1,2,4-triazole, 1H- and 2H— isoindole, and 1H- and 2H-pyrazole. Tautomeric forms can be in equilibrium or sterically locked into one form by appropriate substitution.

In some embodiments, the compounds described herein can contain one or more asymmetric centers and thus occur as racemates and racemic mixtures, enantiomerically enriched mixtures, single enantiomers, individual diastereomers and diastereomeric mixtures (e.g., including (R)- and (S)-enantiomers, diastereomers, (D)-isomers, (L)-isomers, (+) (dextrorotatory) forms, (−) (levorotatory) forms, the racemic mixtures thereof, and other mixtures thereof). Additional asymmetric carbon atoms can be present in a substituent, such as an alkyl group. All such isomeric forms, as well as mixtures thereof, of these compounds are expressly included in the present description. The compounds described herein can also or further contain linkages wherein bond rotation is restricted about that particular linkage, e.g. restriction resulting from the presence of a ring or double bond (e.g., carbon-carbon bonds, carbon-nitrogen bonds such as amide bonds). Accordingly, all cis/trans and E/Z isomers and rotational isomers are expressly included in the present description. Unless otherwise mentioned or indicated, the chemical designation of a compound encompasses the mixture of all possible stereochemically isomeric forms of that compound.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, IN 1972), each of which is incorporated herein by reference in their entireties. It is also understood that the compounds described herein include all possible regioisomers, and mixtures thereof, which can be obtained in pure form by standard separation procedures known to those skilled in the art, and include, but are not limited to, column chromatography, thin-layer chromatography, and high-performance liquid chromatography.

Unless specifically defined, compounds provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}C$], [$^{18}F$]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in Remington's *Pharmaceutical Sciences,* 17th ed., Mack Publishing Company, Easton, Pa., 1985, p. 1418 and *Journal of Pharmaceutical* Science, 66, 2 (1977). Conventional methods for preparing salt forms are described, for example, in Handbook of *Pharmaceutical Salts: Properties, Selection, and Use, Wiley*-VCH, 2002.

EAAT2 Activators

Provided herein are compounds defined by Formula I

Formula I

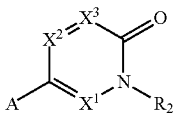

wherein

Y is O, S, or $NR^1$;

$X^1$ is CH orN;

$X^2$ is $CR^3$ or N;

$X^3$ is $CR^4$ or N;

A is selected from the group consisting of 6-10 membered aryl and 5-10 membered heteroaryl, each of which is optionally substituted by 1, 2, 3, or 4 independently selected $R^A$ groups;

$R^1$ is selected from H and $C_{1-6}$ alkyl;

$R^2$ is $—(CHR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^CR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, A can be phenyl, which can be unsubstituted or substituted by 1, 2, 3, or 4 independently selected $R^A$ groups. In other embodiments, A can be a 5-10 membered heteroaryl, which can be unsubstituted or substituted by 1, 2, 3, or 4 independently selected $R^A$ groups. In certain embodiments, A can be an unsubstituted 5-6 membered heteroaryl. In certain embodiments, A can be unsubstituted pyridyl. In certain embodiments, A can be selected from the group consisting of unsubstituted 2-pyridyl and unsubstituted 3-pyridyl. In certain embodiments, A can be unsubstituted 2-pyridyl. In certain embodiments, A can be unsubstituted 3-pyridyl.

In some embodiments, Y can be O.

In some embodiments, one of $X^1$, $X^2$, and $X^3$ is N. For example, in some embodiments, $X^1$ is N, $X^2$ is $CR^3$, and $X^3$ is $CR^4$. In other embodiments, $X^1$ is CH, $X^2$ is N, and $X^3$ is $CR^4$.

In some embodiments, $R^3$, when present, is H.

In some embodiments, $R^4$, when present, is H.

In some embodiments, the compound can be defined by Formula II

Formula II

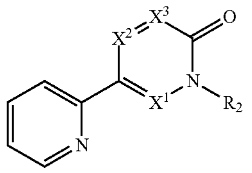

wherein $X^1$ is CH or N;

$X^2$ is $CR^3$ or N;

$X^3$ is $CR^4$ or N;

$R^2$ is $-(CHR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NRW)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^CR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, the compound can be defined by Formula IIA

Formula IIA

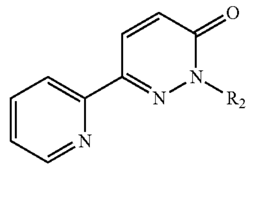

wherein $R^2$ is —$(CHR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NRW)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^CR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, the compound can be defined by Formula IIB

Formula IIB

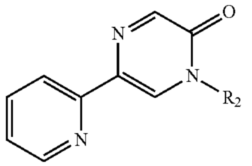

wherein $R^2$ is —$(CR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NRW)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^CR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups; $R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, the compound can be defined by Formula III

Formula III

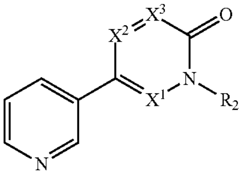

wherein $X^1$ is CH or N;

$X^2$ is $CR^3$ or N;

$X^3$ is $CR^4$ or N;

$R^2$ is —$(CR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^CR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NRW)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^CR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, the compound can be defined by Formula IIIA

Formula IIIA

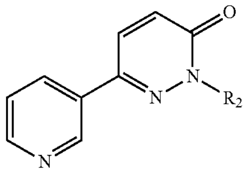

wherein $R^2$ is —$(CHR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR)NR^cR^d$, $NRS(O)R^b$, $NRS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, the compound can be defined by Formula IIIB

Formula IIIB

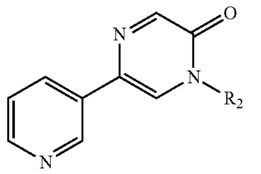

wherein $R^2$ is —$(CHR^E)_nR^5$;

$R^5$ is selected from the group consisting of $OR^C$, $NR^CR^D$, $C(O)NR^CR^D$, $C(O)OR^C$, H, $C_{1-6}$ alkyl, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl,and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In some embodiments, $R^2$ can be selected from the group consisting of —$(CH_2)_nR^5$, —$(CH(CH_3))_nR^5$, and —$(CH_2CH(NH_2))_nR^5$. In some embodiments, $R^2$ is —$(CH_2)_n R^5$. In some embodiments, $R^2$ is —$(CH(CH_3))_nR^5$. In some embodiments, $R^2$ is —$(CH_2CH(NH_2))_nR^2$. In some embodiments, n is 0, 1 or 2. In some embodiments, n is 0. In some embodiments, n is 1. In some embodiments, n is 2.

In some embodiments, $R^5$ can be selected from the group consisting of $OR^C$, $NR^CR^D$, $C(O)NR^CR^D$, $C_{6-10}$ aryl, $C_{3-10}$ cycloalkyl, 4-10 membered heterocycloalkyl, and 5-10 membered heteroaryl, wherein the $C_{6-10}$ aryl, $C_{3-10}$ cycloalkyl, 4-10 membered heterocycloalkyl, and 5-10 membered heteroaryl are each optionally substituted by 1, 2, 3, or 4 independently selected $R^B$ groups.

In some embodiments, $R^5$ can be selected from the group consisting of $OR^C$, $NR^CR^D$, $C(O)NR^cR^D$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups. In certain embodiments, $R^5$ can be selected from the group consisting of $OR^C$, $NR^CR^D$, $C(O)NR^cR^D$, phenyl, $C_{3-6}$ cycloalkyl, 4-6 membered heterocycloalkyl, and 5-6 membered heteroaryl, wherein the phenyl, 4-6 membered heterocycloalkyl, and 5-6 membered heteroaryl are each optionally substituted by 1 or 2 independently selected $R^B$ groups.

In some embodiments, $R^5$ can be selected from the group consisting of $OCH_3$, $N(CH_3)_2$, $C(O)N(CH_3)_2$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups. In certain embodiments, $R^5$ can be selected from the group consisting of $OCH_3$, $N(CH_3)_2$, $C(O)N(CH_3)_2$, phenyl, $C_{3-6}$ cycloalkyl, 4-6 membered heterocycloalkyl, and 5-6 membered heteroaryl, wherein the phenyl, 4-6 membered heterocycloalkyl, and 5-6 membered heteroaryl are each optionally substituted by 1 or 2 independently selected $R^B$ groups.

In some embodiments, $R^5$ can be selected from the group consisting of $OCH_3$, $N(CH_3)_2$, $C(O)NH_2$, $C(O)NHCH_3$, $C(O)N(CH_3)_2$, $C(O)N(CH_2CH_3)_2$, phenyl, cyclopentyl, cyclohexyl, oxazolyl, pyridyl, thiazolyl, imidazolyl, pyrazolyl, piperidinyl, piperidinonyl, pyrrolidinyl, pyrrolidinonyl, benzoimidazolyl, and quinolinyl, wherein the phenyl, cyclopentyl, cyclohexyl, oxazolyl, pyridyl, thiazolyl, imidazolyl, pyrazolyl, piperidinyl, piperidinonyl, pyrrolidinyl, pyrrolidinonyl, benzoimidazolyl, and quinolinyl are each optionally substituted by 1 or 2 independently selected $R^B$ groups.

In some embodiments, $R^5$ can be selected from the group consisting of H and $C_{1-6}$ alkyl, wherein the $C_{1-6}$ alkyl is optionally substituted by 1, 2, 3, or 4 independently selected $R^B$ groups. In some embodiments, $R^5$ can be hydrogen. In some embodiments, $R^5$ can be a $C_{1-6}$ alkyl group optionally substituted by one or more halogens (e.g., fluorines). In certain embodiments, $R^5$ can by a trifluoromethyl group.

In some embodiments, $R^C$ and $R^D$, when present, can be independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-6 membered heteroaryl, 4-6 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-6 membered heteroaryl, 4-6 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups.

In some embodiments, each $R^B$, when present, can be independently selected from the group consisting of $C_{1-6}$ alkyl and $NR^cR^d$. In certain embodiments, each $R^B$, when present, can be independently selected from the group consisting of $C_{1-3}$ alkyl and $N(C_{1-3}\text{ alkyl})_2$.

In some embodiments, $R^2$ is not one of the groups shown below.

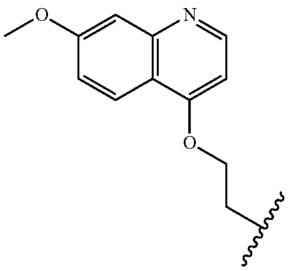

-continued

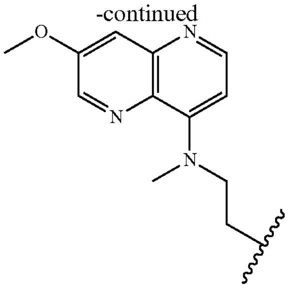

In particular embodiments, the compound can be defined by the formula below

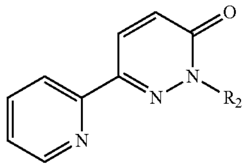

wherein $R^2$ is $—(CH_2)_nNR^CR^D$;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In particular embodiments, the compound can be defined by the formula below

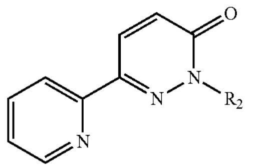

wherein $R^2$ is —$(CH_2)_nNR^cR^D$; and $R^C$ and $R^D$ are independently selected from H, $C_{1-6}$ alkyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In particular embodiments, the compound can be defined by the formula below

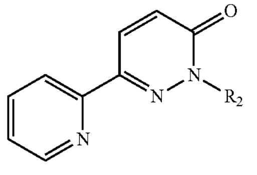

wherein $R^2$ is —$(CH_2)_nNR^cR^D$; and $R^C$ and $R^D$ are independently selected from H, $C_{1-6}$ alkyl, $C_{1-4}$ haloalkyl, 6-10 membered aryl, 5-10 membered heteroaryl; wherein the $C_{1-6}$ alkyl, $C_{1-4}$ haloalkyl, 6-10 membered aryl, and 5-10 membered heteroaryl, are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

In particular embodiments, the compound can be defined by the formula below

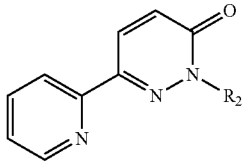

wherein $R^2$ is —$(CH_2)_nNR^cR^D$; and $R^C$ and $R^D$ are independently selected from H, $C_{1-6}$ alkyl, and $C_{1-4}$ haloalkyl; wherein the $C_{1-6}$ alkyl and $C_{1-4}$ haloalkyl are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group optionally substituted with 1, 2, or 3 independently selected $R^6$ groups;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5;

or a pharmaceutically acceptable salt, ester, or N-oxide thereof.

Example Compounds are Shown Below
| Compound | Structure |
|---|---|
| 100 | 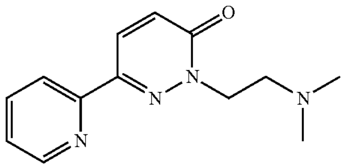 |
| 101 | 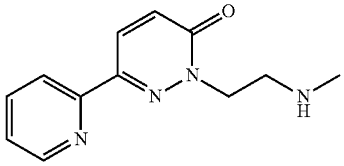 [SMILES: CNCCn1nc(-c2ccccn2)ccc1=O] |
| 102 | 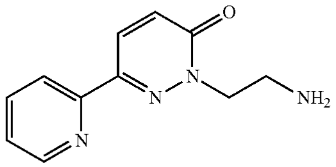 [SMILES: NCCn1nc(-c2ccccn2)ccc1=O] |
| 103 | 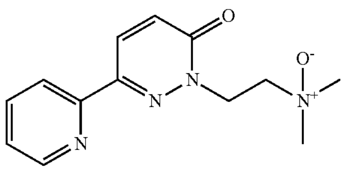 [SMILES: C[N+](C)([O-])CCn1nc(-c2ccccn2)ccc1=O] |
| 104 | 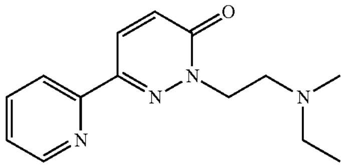 [SMILES: CCN(C)CCn1nc(-c2ccccn2)ccc1=O] |
| 105 | 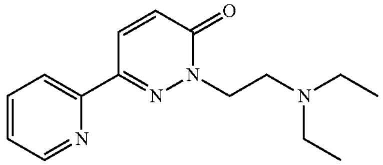 [SMILES: CCN(CC)CCn1nc(-c2ccccn2)ccc1=O] |
| 106 | 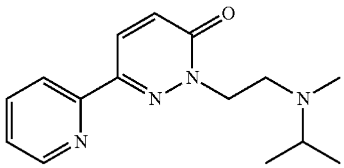 [SMILES: CC(C)N(C)CCn1nc(-c2ccccn2)ccc1=O] |
| 107 | 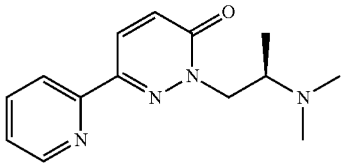 [SMILES: C[C@H](Cn1nc(-c2ccccn2)ccc1=O)N(C)C] |
-continued
| Compound | Structure |
|---|---|
| 108 | 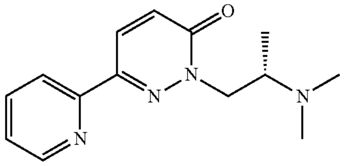 [SMILES: C[C@@H](Cn1nc(-c2ccccn2)ccc1=O)N(C)C] |
| 109 | 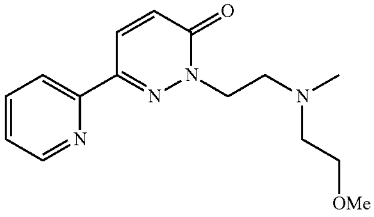 [SMILES: COCCN(C)CCn1nc(-c2ccccn2)ccc1=O] |
| 110 | 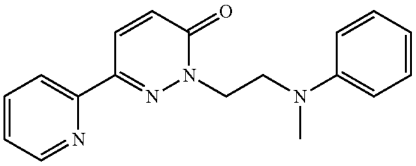 [SMILES: CN(CCn1nc(-c2ccccn2)ccc1=O)c1ccccc1] |
| 111 | 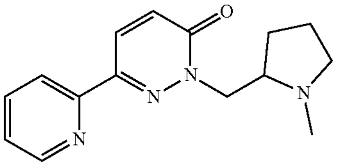 [SMILES: CN1CCCC1Cn1nc(-c2ccccn2)ccc1=O] |
| 112 | 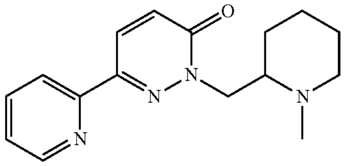 [SMILES: CN1CCCCC1Cn1nc(-c2ccccn2)ccc1=O] |
| 113 | 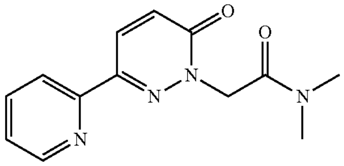 [SMILES: CN(C)C(=O)Cn1nc(-c2ccccn2)ccc1=O] |
| 114 | 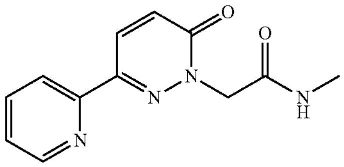 [SMILES: CNC(=O)Cn1nc(-c2ccccn2)ccc1=O] |
| 115 | 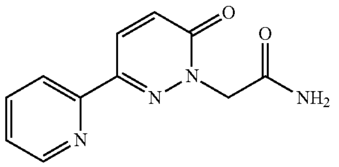 [SMILES: NC(=O)Cn1nc(-c2ccccn2)ccc1=O] |

-continued
| Compound | Structure |
|---|---|
| 116 | 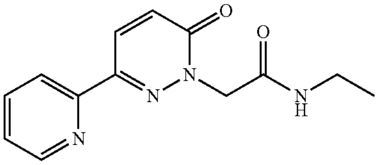 [SMILES: CCNC(=O)Cn1nc(-c2ccccn2)ccc1=O] |
| 117 | 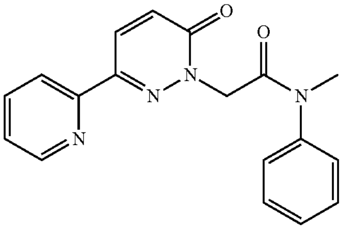 [SMILES: CN(C(=O)Cn1nc(-c2ccccn2)ccc1=O)c1ccccc1] |
| 118 | 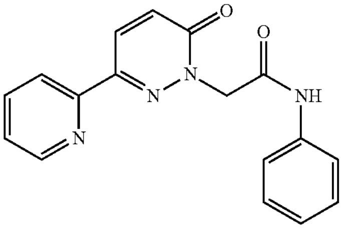 [SMILES: O=C(Cn1nc(-c2ccccn2)ccc1=O)Nc1ccccc1] |
| 119 | 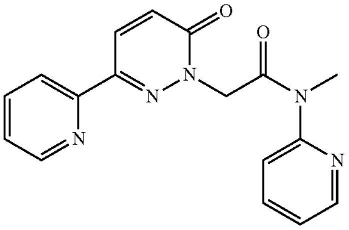 [SMILES: CN(C(=O)Cn1nc(-c2ccccn2)ccc1=O)c1ccccn1] |
| 120 | 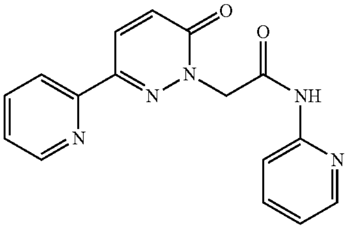 [SMILES: O=C(Cn1nc(-c2ccccn2)ccc1=O)Nc1ccccn1] |
| 121 | 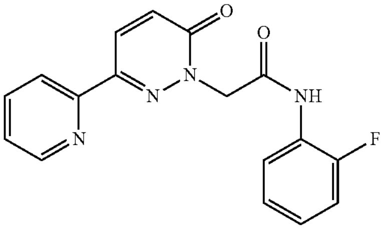 [SMILES: O=C(Cn1nc(-c2ccccn2)ccc1=O)Nc1ccccc1F] |
| 122 | 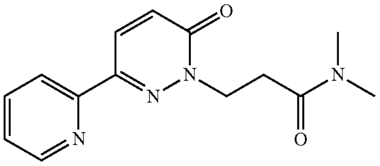 [SMILES: CN(C)C(=O)CCn1nc(-c2ccccn2)ccc1=O] |
-continued
| Compound | Structure |
|---|---|
| 123 | 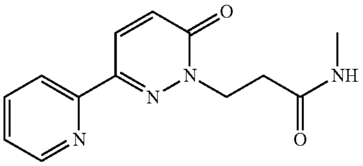 [SMILES: CNC(=O)CCn1nc(-c2ccccn2)ccc1=O] |
| 124 | 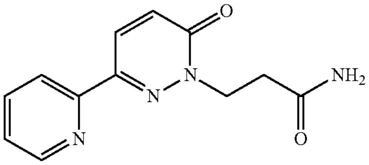 [SMILES: NC(=O)CCn1nc(-c2ccccn2)ccc1=O] |
| 125 | 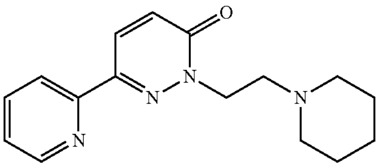 [SMILES: O=c1ccc(-c2ccccn2)nn1CCN1CCCCC1] |
| 126 | 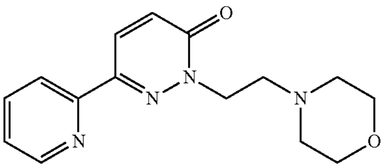 [SMILES: O=c1ccc(-c2ccccn2)nn1CCN1CCOCC1] |
| 127 | 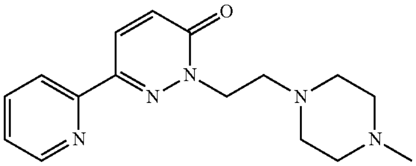 [SMILES: CN1CCN(CCn2nc(-c3ccccn3)ccc2=O)CC1] |
| 128 | 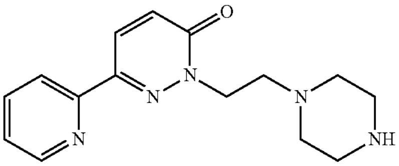 [SMILES: O=c1ccc(-c2ccccn2)nn1CCN1CCNCC1] |
| 129 | 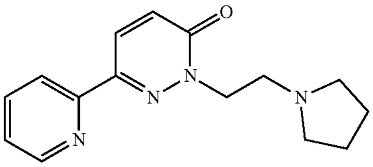 [SMILES: O=c1ccc(-c2ccccn2)nn1CCN1CCCC1] |
| 130 | 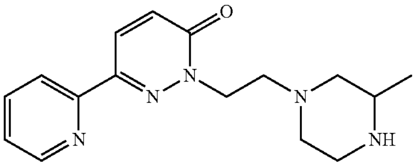 [SMILES: CC1CN(CCn2nc(-c3ccccn3)ccc2=O)CCN1] |
| 131 | 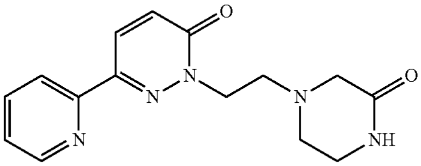 [SMILES: O=C1CN(CCn2nc(-c3ccccn3)ccc2=O)CCN1] |

-continued
| Compound | Structure |
|---|---|
| 132 | 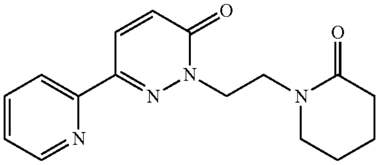 [SMILES: O=C1CCCCN1CCn1nc(-c2ccccn2)ccc1=O] |
| 133 | 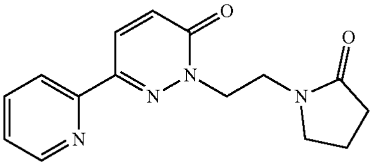 [SMILES: O=C1CCCN1CCn1nc(-c2ccccn2)ccc1=O] |
| 134 | 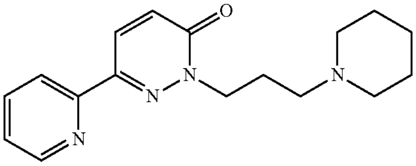 [SMILES: O=c1ccc(-c2ccccn2)nn1CCCN1CCCCC1] |
| 135 | 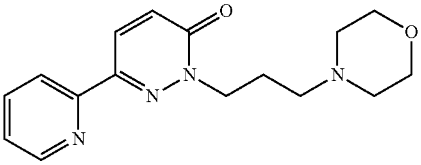 [SMILES: O=c1ccc(-c2ccccn2)nn1CCCN1CCOCC1] |
| 136 | 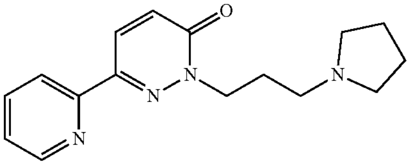 [SMILES: O=c1ccc(-c2ccccn2)nn1CCCN1CCCC1] |
| 137 | 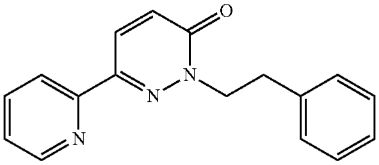 [SMILES: O=c1ccc(-c2ccccn2)nn1CCc1ccccc1] |
| 138 | 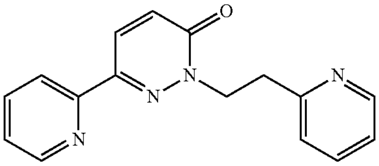 [SMILES: O=c1ccc(-c2ccccn2)nn1CCc1ccccn1] |
| 139 | 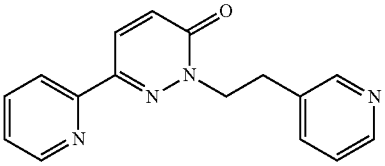 [SMILES: O=c1ccc(-c2ccccn2)nn1CCc1cccnc1] |
-continued
| Compound | Structure |
|---|---|
| 140 | 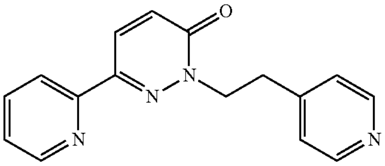 [SMILES: O=c1ccc(-c2ccccn2)nn1CCc1ccncc1] |
| 141 | 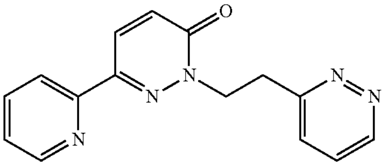 [SMILES: O=c1ccc(-c2ccccn2)nn1CCc1cccnn1] |
| 142 | 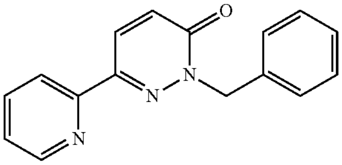 [SMILES: O=c1ccc(-c2ccccn2)nn1Cc1ccccc1] |
| 143 | 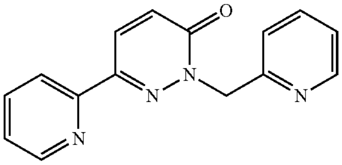 [SMILES: O=c1ccc(-c2ccccn2)nn1Cc1ccccn1] |
| 144 | 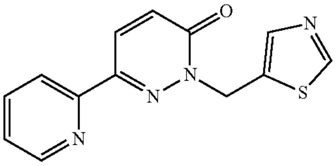 |
| 145 | 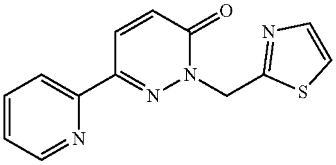 |
| 146 | 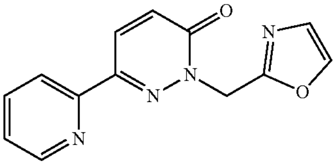 [SMILES: O=c1ccc(-c2ccccn2)nn1Cc1ncco1] |
| 147 | 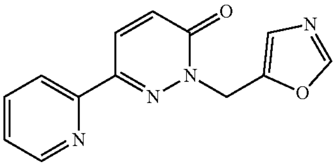 [SMILES: O=c1ccc(-c2ccccn2)nn1Cc1cnco1] |
| 148 | 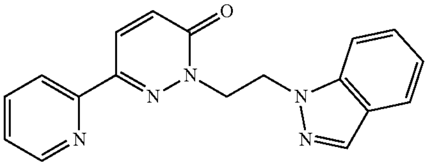 [SMILES: O=c1ccc(-c2ccccn2)nn1CCn1ncc2ccccc21] |

-continued
| Compound | Structure |
| --- | --- |
| 149 | 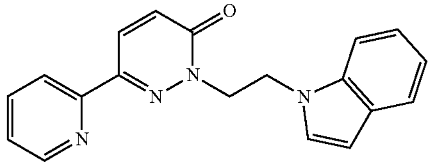 |
| 150 | 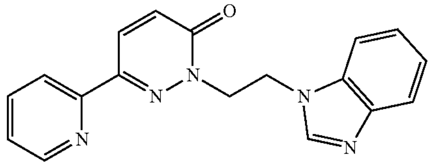 [SMILES: O=c1ccc(-c2ccccn2)nn1CCn1ccc2ccccc21] |
| 151 | 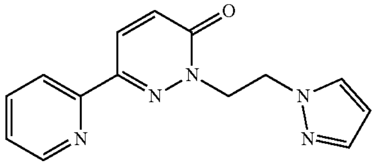 [SMILES: O=c1ccc(-c2ccccn2)nn1CCn1cccn1] |
| 152 | 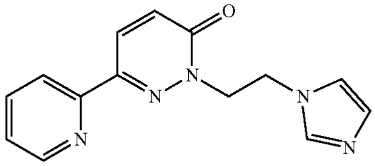 [SMILES: O=c1ccc(-c2ccccn2)nn1CCn1ccnc1] |
| 153 | 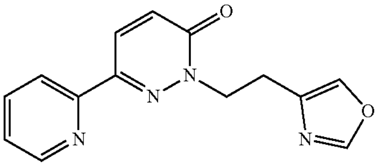 [SMILES: O=c1ccc(-c2ccccn2)nn1CCc1cocn1] |
| 154 | 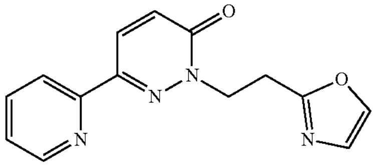 [SMILES: O=c1ccc(-c2ccccn2)nn1CCc1ncco1] |
| 155 | 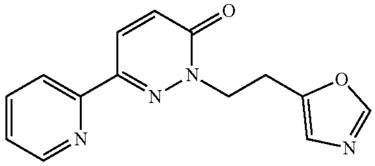 |
| 156 | 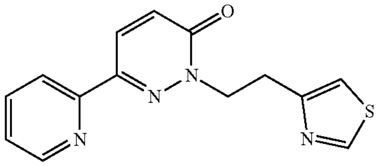 [SMILES: O=c1ccc(-c2ccccn2)nn1CCc1cscn1] |
-continued
| Compound | Structure |
| --- | --- |
| 157 | 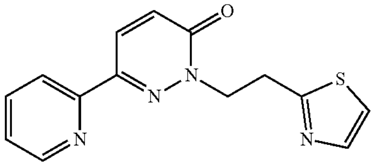 [SMILES: O=c1ccc(-c2ccccn2)nn1CCc1nccs1] |
| 158 | 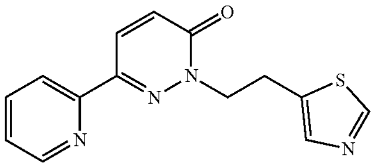 [SMILES: O=c1ccc(-c2ccccn2)nn1CCc1cncs1] |
| 159 | 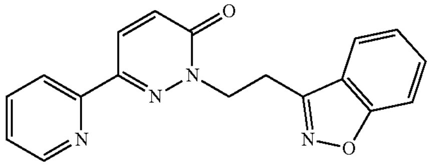 [SMILES: O=c1ccc(-c2ccccn2)nn1CCc1noc2ccccc12] |
| 160 | 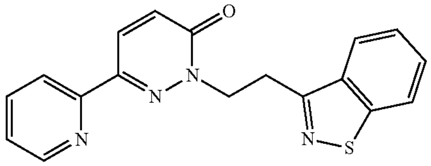 [SMILES: O=c1ccc(-c2ccccn2)nn1CCc1nsc2ccccc12] |
| 161 | 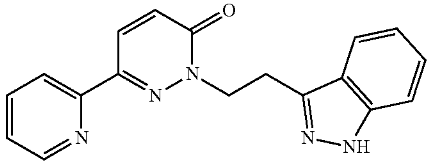 [SMILES: O=c1ccc(-c2ccccn2)nn1CCc1n[nH]c2ccccc12] |
| 162 | 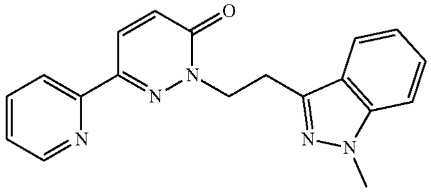 [SMILES: Cn1nc(CCn2nc(-c3ccccn3)ccc2=O)c2ccccc21] |
| 163 | 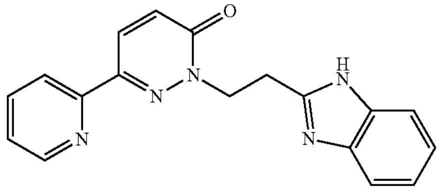 |
| 164 | 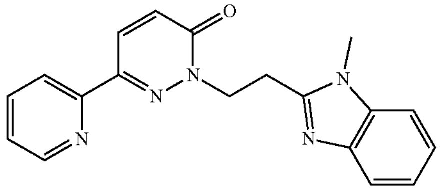 [SMILES: Cn1c(CCn2nc(-c3ccccn3)ccc2=O)nc2ccccc21] |

-continued
| Compound | Structure |
|---|---|
| 165 | 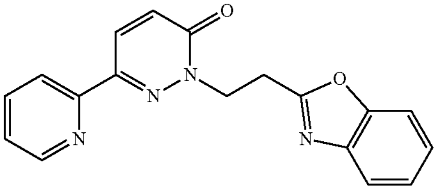 [SMILES: O=c1ccc(-c2ccccn2)nn1CCc1nc2ccccc2o1] |
| 166 | 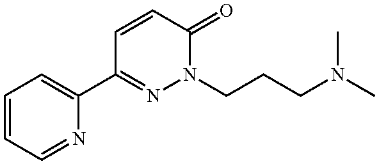 [SMILES: CN(C)CCCn1nc(-c2ccccn2)ccc1=O] |
| 167 | 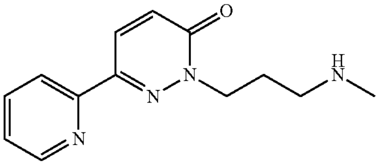 [SMILES: CNCCCn1nc(-c2ccccn2)ccc1=O] |
| 168 | 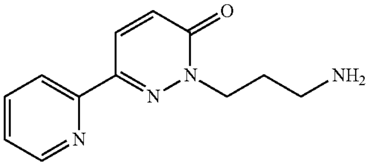 [SMILES: NCCCn1nc(-c2ccccn2)ccc1=O] |
| 169 | 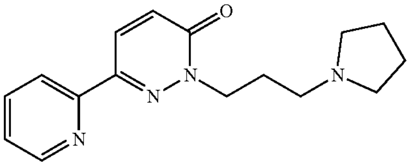 [SMILES: O=c1ccc(-c2ccccn2)nn1CCCN1CCCC1] |
| 170 | 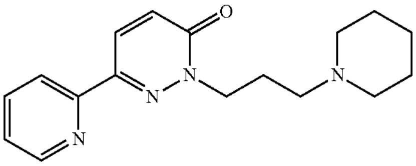 [SMILES: O=c1ccc(-c2ccccn2)nn1CCCN1CCCCC1] |
| 171 | 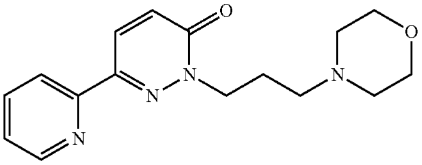 [SMILES: O=c1ccc(-c2ccccn2)nn1CCCN1CCOCC1] |
| 172 | 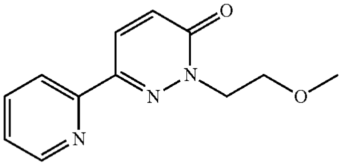 [SMILES: COCCn1nc(-c2ccccn2)ccc1=O] |
-continued
| Compound | Structure |
|---|---|
| 173 | 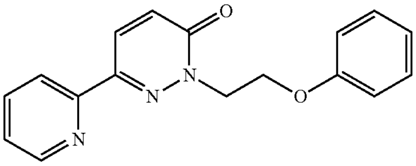 |
| 174 | 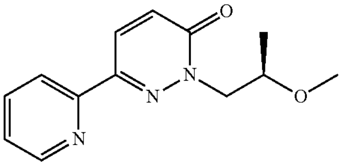 [SMILES: CO[C@H](C)Cn1nc(-c2ccccn2)ccc1=O] |
| 175 | 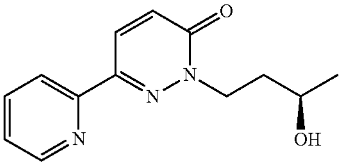 [SMILES: C[C@@H](O)CCn1nc(-c2ccccn2)ccc1=O] |
| 176 | 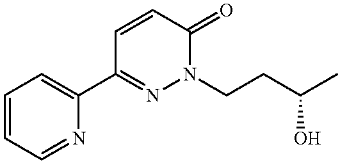 [SMILES: C[C@H](O)CCn1nc(-c2ccccn2)ccc1=O] |
| 177 | 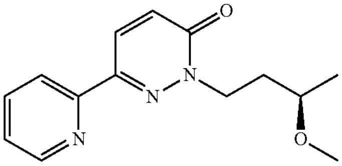 [SMILES: CO[C@H](C)CCn1nc(-c2ccccn2)ccc1=O] |
| 178 | 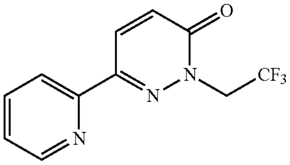 [SMILES: O=c1ccc(-c2ccccn2)nn1CC(F)(F)F] |
| 179 | 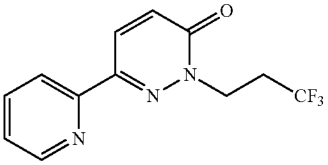 [SMILES: O=c1ccc(-c2ccccn2)nn1CCC(F)(F)F] |
| 180 | 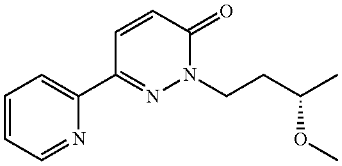 |
| 181 | 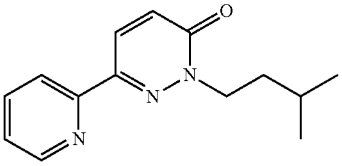 [SMILES: CC(C)CCn1nc(-c2ccccn2)ccc1=O] |

-continued
| Compound | Structure |
| --- | --- |
| 182 | 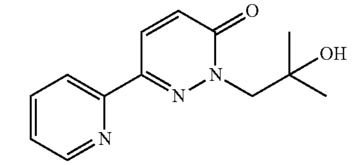 [SMILES: CC(C)(O)Cn1nc(-c2ccccn2)ccc1=O] |
| 183 | 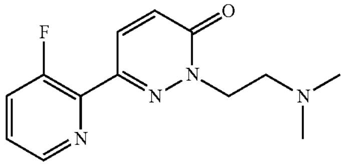 [SMILES: CN(C)CCn1nc(-c2ncccc2F)ccc1=O] |
| 184 | 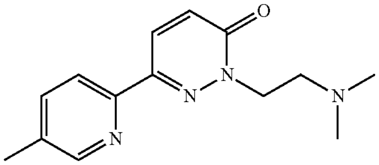 |
| 185 | 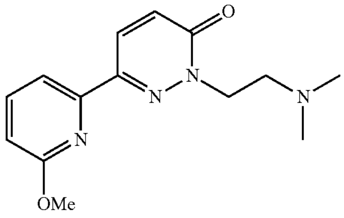 [SMILES: COc1cccc(-c2ccc(=O)n(CCN(C)C)n2)n1] |
| 186 | 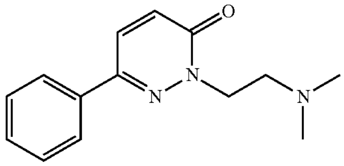 |
| 187 | 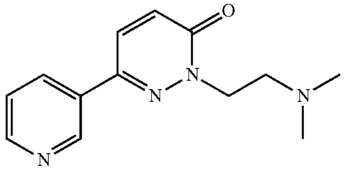 [SMILES: CN(C)CCn1nc(-c2cccnc2)ccc1=O] |
| 188 | 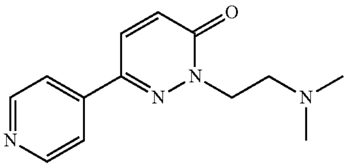 [SMILES: CN(C)CCn1nc(-c2ccncc2)ccc1=O] |
| 189 | 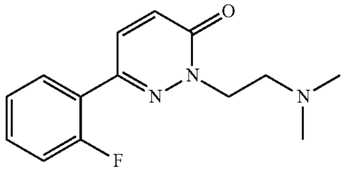 [SMILES: CN(C)CCn1nc(-c2ccccc2F)ccc1=O] |
| 190 | 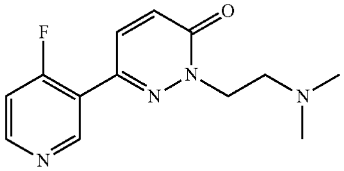 [SMILES: CN(C)CCn1nc(-c2cnccc2F)ccc1=O] |
| 191 | 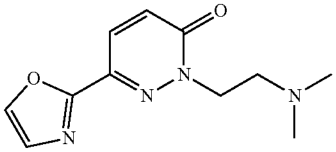 |
| 192 | 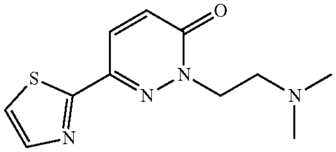 [SMILES: CN(C)CCn1nc(-c2nccs2)ccc1=O] |
| 193 | 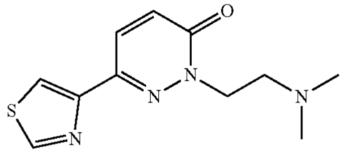 [SMILES: CN(C)CCn1nc(-c2cscn2)ccc1=O] |
| 194 | 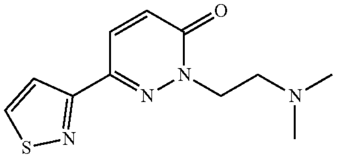 [SMILES: CN(C)CCn1nc(-c2ccsn2)ccc1=O] |
| 195 | 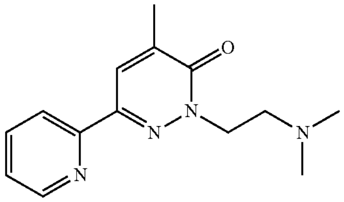 [SMILES: Cc1cc(-c2ccccn2)nn(CCN(C)C)c1=O] |
| 196 | 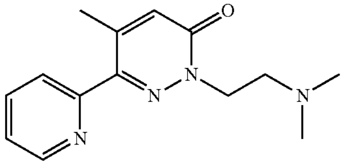 [SMILES: Cc1cc(=O)n(CCN(C)C)nc1-c1ccccn1] |
| 197 | 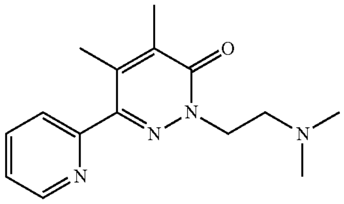 [SMILES: Cc1c(-c2ccccn2)nn(CCN(C)C)c(=O)c1C] |

-continued
| Compound | Structure |
|---|---|
| 198 | 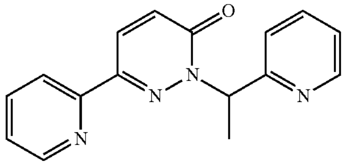 [SMILES: CC(c1ccccn1)n1nc(-c2ccccn2)ccc1=O] |
| 199 | 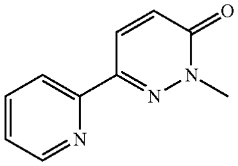 |
| 200 | 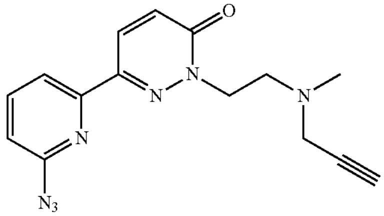 [SMILES: C#CCN(C)CCn1nc(-c2cccc(N=[N+]=[N-])n2)ccc1=O] |
| 201 | 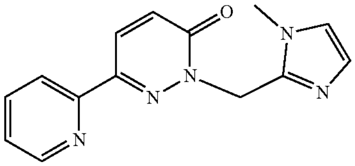 [SMILES: Cn1ccnc1Cn1nc(-c2ccccn2)ccc1=O] |
| 202 | 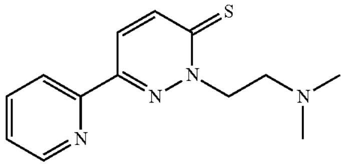 [SMILES: CN(C)CCn1nc(-c2ccccn2)ccc1=S] |
| 203 | 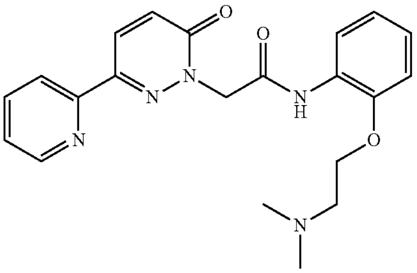 [SMILES: CN(C)CCOc1ccccc1NC(=O)Cn1nc(-c2ccccn2)ccc1=O] |
| 204 | 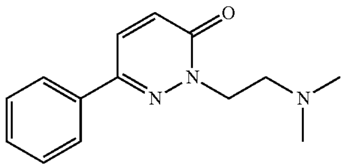 [SMILES: CN(C)CCn1nc(-c2ccccc2)ccc1=O] |
| 205 | 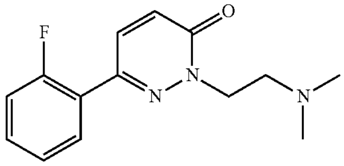 [SMILES: CN(C)CCn1nc(-c2ccccc2F)ccc1=O] |
-continued
| Compound | Structure |
|---|---|
| 206 | 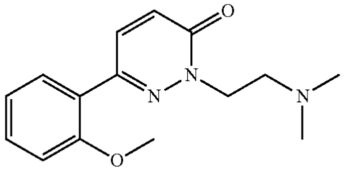 [SMILES: COc1ccccc1-c1ccc(=O)n(CCN(C)C)n1] |
| 207 | 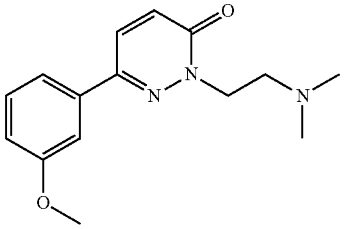 [SMILES: COc1cccc(-c2ccc(=O)n(CCN(C)C)n2)c1] |
| 208 | 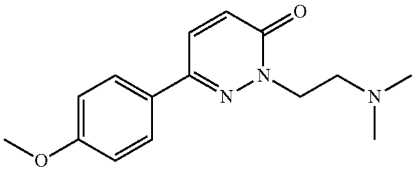 |
| 209 | 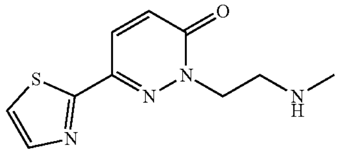 [SMILES: CNCCn1nc(-c2nccs2)ccc1=O] |
| 210 | 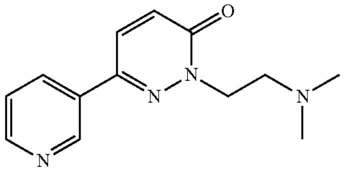 [SMILES: CN(C)CCn1nc(-c2cccnc2)ccc1=O] |
| 211 | 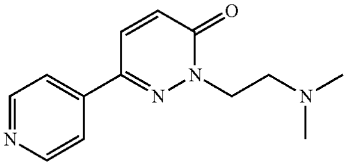 [SMILES: CN(C)CCn1nc(-c2ccncc2)ccc1=O] |
| 212 | 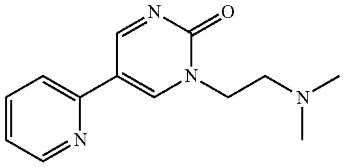 [SMILES: CN(C)CCn1cc(-c2ccccn2)cnc1=O] |
| 213 | 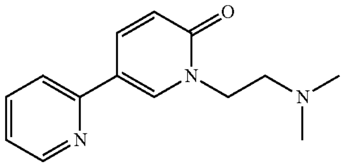 [SMILES: CN(C)CCn1cc(-c2ccccn2)ccc1=O] |

-continued

| Compound | Structure |
|---|---|
| 214 | 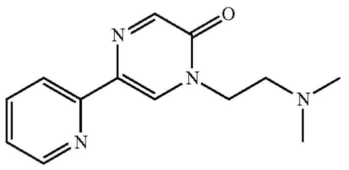 [SMILES: CN(C)CCn1cc(-c2ccccn2)ncc1=O] |

Synthesis

The compounds described herein can be prepared using synthetic methodologies known in the art. By way of example, representative EAAT2 activators described herein can be prepared using a Mitsunobu Reaction as shown in Scheme 1.

Scheme 1

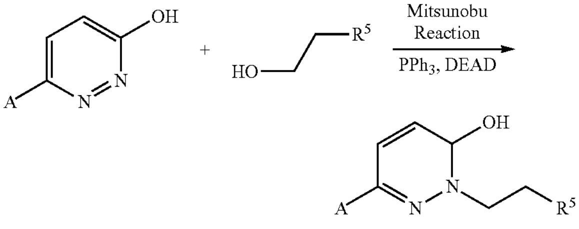

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (*Journal of* Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2nd Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6th Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

Also provided are methods for the treatment of disorders associated with glutamate excitotoxicity in a subject in need thereof. A number of such disorders are known in the art, and can be readily identified by one of skill in the art. In some embodiments, the methods include a method for treating or preventing glutamate excitotoxicity in a subject in need thereof, the method comprising administering to the subject a therapeutically effective amount of a compound provided herein, or a pharmaceutically acceptable salt thereof. As used herein, the term "subject," refers to any animal, including mammals. For example, the term "subject" includes, but is not limited to, mice, rats, other rodents, rabbits, dogs, cats, swine, cattle, sheep, horses, primates, and humans. In some embodiments, the subject is a human.

In some embodiments, the methods described herein can include in vitro methods, e.g., contacting a sample (e.g., a cell or tissue) with a compound provided herein, or a pharmaceutically acceptable salt thereof.

In some embodiments, the disorder is an acute neurological condition such as ischemic stroke, epilepsy, hypoglycemia, hypoxia, or trauma (see e.g., J. Neurosci. 2016 Oct. 12; 36(41):10529-10544; J. Clin. Invest. 2014 March; 124(3): 1255-67; and Neurochem. Int. 2006 April; 48(5):394-403).

In some embodiments, the disorder is a chronic neurodegenerative disorder such as Parkinson's disease, Alzheimer's disease, multiple sclerosis, mesial temporal sclerosis, Huntington's disease, AIDS dementia complex, or amyotrophic lateral sclerosis (ALS) (see, e.g., Hu et al., "Glutamate receptors in preclinical research on Alzheimer's disease: Update on recent advances." Pharmacol Biochem Behav. 2011 Apr. 22 [Epub ahead of print, doi:10.1016/j.pbb.2011.04.013]; Wang and Qin, Apoptosis. 15(11):1382-402 (2010); Kaul and Lipton, Curr HIV Res. 4(3):307-18 (2006); Kim et al., J Cell Physiol. 226(10):2484-93 (2011); Sheldon and Robinson, Neurochem Int. 51(6-7):333-55 (2007); Guo et al., Hum. Mol. Genet. 2003, 12, 2519; Tian et al., J. Biol. Chem. 282:1727 (2007); Hazell, Neurochem. Int. 50:941 (2007); Seifert et al., Brain. Res. Rev. 63:212 (2010); Tian et al., J. Neurochem. 113:978 (2010); Olney, "Neurotoxicity of excitatory amino acids." In: McGeer E, Olney J, McGeer P, eds. *Kainic Acid as a Tool in Neurobiology*. New York: Raven Press; 1978:95-121; Olney, APMIS Suppl 40:103-112 (2010); J. Exp. Med. 2015 Mar. 9; 212 (3):319-32; Neurobiol. Aging. 2015 July; 36(7):2260-71;

Neural. Plast. 2016; 2016:8941327; PLoS One. 2008 Sep. 5; 3(9):e3149; J. Clin. Invest. 2014 March; 124(3):1255-67; J. Neurochem. 2012 May; 121(4):629-38; and Curr. HIV Res. 2012 July; 10(5):392-406).

In some embodiments, the disorder is depression (see, e.g., Chen et al., Presynaptic glutamatergic dysfunction in bipolar disorder, Biol. Pshychiatry, 67(11): 1007-1009 (2010)).

In some embodiments, glutamate excitotoxicity can be a result of an environmental toxin, e.g., Tributyltin (Nakatsu et al., Toxicol. Sci. (January 2006) 89 (1): 235-242), lead, and domoic acid.

In some embodiments, excessive glutamate is associated with chronic pain disorders including migraine, fibromyalgia, temporomandibular disorders, neuropathic pain, visceral pain, or complex regional pain syndrome (see, e.g., Chizh et al., Amino Acids, 23(1-3):169-76 (2002); Descalzi et al., Mol Neurobiol. 40(3):253-9. Epub 2009 October 11 (2009); Larsson, Mol Neurobiol. 40(3):260-88 (2009); Yogeswaari et al., Expert Opin Ther Targets. 13(8):925-43 (2009); Vargas, Curr Pain Headache Rep. 13(1):64-6 (2009); Adv. Pharmacol. 2016; 75:245-71; J. Neurochem. 2014 December; 131(6):712-30; Eurasian J Med. 2011 December; 43(3):182-5; and J. Pharmacol. Sci. 2010; 114(4):347-53).

Disruptions in glutamate homeostasis are associated with addictive disorders. As substance abuse develops into addiction, neurochemistry shifts from dopamine-based to predominantly glutamate-based. Thus, subjects suffering from drug addiction and dependence, including alcohol and cocaine addiction, can also be treated using the methods described herein. See, e.g., Tzschentke, Amino Acids 23(1-3):147-52 (2002); Reissner and Kalivas, Behav Pharmacol. 2010 September; 21(5-6):514-22 (2010); Myers et al., Neuropsychopharmacology. 36(1):274-93 (2011); World J. Psychiatry. 2016 Mar. 22; 6(1):31-42; CNS Neurol. Disord. Drug. Targets. 2015; 14(6):745-56; Neuroscientist. 2014 December; 20(6):610-22; and Behav. Pharmacol. 2010 September; 21(5-6):514-22.

Glutamate has also been shown to play a role in some psychotic disorders, including schizophrenia, bipolar disorder, and autism (see e.g., Curr Mol Pharmacol. 2013 July; 6(2):66-73; Eur J Pharmacol. 2012 May 5; 682(1-3):1-11; Iran J Child Neurol. 2015 Winter; 9(1):99-102; J Biomed Sci. 2005 December; 12(6):975-84. The methods and compounds described herein can be used to treat subjects with psychotic disorders such as schizophrenia, bipolar disorder, and autism.

Glutamate has also been shown to play a role in some cancers, including necrosis in glioblastoma, which is associated with poor prognosis. See, e.g., Noch and Khalili, Cancer Biol Ther. 8(19):1791-7 (2009). Thus, the compounds and compositions described herein can be used to treat subjects with cancers, e.g., brain cancers such as glioblastoma and glioma.

Glutamate has been shown to play a role in modulating various mood disorders, for example, major depressive disorder (Owen, Drugs today, 2012, 48(7):469-78), anxiety disorders (see e.g., Neuropsychiatr Dis Treat. 2013; 9:1101-12), depressive disorders (see e.g., Expert Rev Clin Pharmacol. 2016 Oct. 26; Biol Psychiatry. 2007 Jan. 15; 61(2): 250-2; and Biol Psychiatry. 2007 Jan. 15; 61(2):137-8), borderline personality disorder (see e.g., Neuropsychopharmacology. 2016 January; 41(2):410-8), attention-deficit-hyperactivity disorder (see e.g., Neuropsychopharmacology. 2016 January; 41(2):410-8; and World J. Biol. Psychiatry. 2016 December 15:1-9), suicidal behavior (see e.g., Prog. Neuropsychopharmacol Biol. Psychiatry. 2016 Oct. 27), eating disorders (see e.g., Curr. Pharm. Des. 2011; 17(14): 1396-409), posttraumatic stress disorder (see e.g., Neurosci. Lett. 2016 Dec. 1), gulf war illness (see e.g., J. Neurochem. 2011 October; 119(2):303-13), and obsessive-Compulsive Disorder (see e.g., Pharmacol. Ther. 2011 December; 132 (3): 314-332).

The presence of a disorder associated with glutamate excitotoxicity can be diagnosed or determined using methods known in the art, including spectroscopy at 0.5 T to observe the combined glutamate and glutamine (glx) peak (see, e.g., Prost et al., Magn Reson Med 1997; 37:615-618; Mark et al., American *Journal of* Neuroradiology 22:1813-1824 (2001)). Other known clinical diagnostic methods can also be used to diagnose the presence of a disorder known to be associated with glutamate excitotoxicity, e.g., as described herein.

In some embodiments, glutamate excitotoxicity (and subsequent neurological damage) can be a result of an environmental toxin, e.g., Tributyltin (Nakatsu et al., Toxicol. Sci. (January 2006) 89 (1): 235-242), lead, and domoic acid. Subjects who have been or will be exposed to such toxins can be considered to have a disorder associated with glutamate excitotoxicity and can be treated using the methods described herein. In some embodiments subjects who have been exposed to an environmental toxin known to cause or contribute to glutamate excitotoxicity can be treated using the methods described herein before the onset of clinical (e.g., neurological) symptoms, to prevent or reduce the risk of a disorder associated with glutamate excitotoxicity.

In some embodiments, also provided are methods for treating a disease or disorder selected from the group consisting of ischemic stroke, epilepsy, trauma, a chronic neurodegenerative disorder, a psychotic disorder, a pain disorder, an addiction, a cancer, a mood disorder, or depression in a subject in need thereof, the method comprising administering to the subject an effective amount of a compound provided herein.

In some embodiments, also provided are methods for treating a disease or disorder selected from the group consisting of ischemic stroke, epilepsy, trauma, a chronic neurodegenerative disorder, a psychotic disorder, a pain disorder, an addiction, a cancer, or depression in a subject in need thereof, the method comprising administering to the subject an effective amount of a compound provided herein.

Example traumas include, but are not limited to, blunt trauma, an abrasion, an avulsion, an incision, a laceration, a puncture, a penetration, a surgical trauma, iatrogenic trauma, a spinal cord injury, a traumatic brain injury, or any combination thereof.

In some embodiments, the chronic neurodegenerative disorder is selected from the group consisting of mild cognitive impairment, Parkinson's disease, Alzheimer's disease, multiple sclerosis, mesial temporal sclerosis, Huntington's disease, AIDS dementia complex, essential tremor, and amyotrophic lateral sclerosis (ALS).

In some embodiments, the psychotic disorder is selected from the group consisting of schizophrenia, bipolar disorder, and autism.

In some embodiments, the pain disorder is selected from the group consisting of migraine, a temporomandibular disorder, neuropathic pain, visceral pain, or complex regional pain syndrome.

In some embodiments, the addiction is selected from the group consisting of alcohol addition, cocaine addiction, heroin addiction, methamphetamine addiction, and nicotine addiction. In some embodiments, the addiction is selected from the group consisting of alcohol addiction and cocaine addiction.

In some embodiments, the cancer is selected from the group consisting of brain cancer, glioblastoma, and glioma. In some embodiments, the cancer is glioblastoma. In some embodiments, the cancer is glioma.

In some embodiments, the mood disorder is selected from the group consisting of an anxiety disorder, a depressive disorder, borderline personality disorder, attention-deficit-hyperactivity disorder, suicidal behavior, an eating disorder, posttraumatic stress disorder, gulf war illness, and obsessive-Compulsive Disorder.

In some embodiments, the depression comprises major depressive disorder. In some embodiments, the depression is major depressive disorder.

In some embodiments, also provided are methods for treating a disease or disorder selected from the group consisting of ischemic stroke, epilepsy, trauma, or a chronic neurodegenerative disorder, including mild cognitive impairment, Parkinson's disease, Alzheimer's disease, multiple sclerosis, mesial temporal sclerosis, Huntington's disease, AIDS dementia complex, essential tremor, or amyotrophic lateral sclerosis (ALS); a psychotic disorder including schizophrenia, bipolar disorder, and autism, a pain disorder including migraine, temporomandibular disorders, neuropathic pain, visceral pain, or complex regional pain syndrome; an addiction including alcohol addiction, cocaine addiction, heroin addiction, methamphetamine addiction, and nicotine addiction; or a cancer, including glioblastoma; or depression in a subject in need thereof, the method comprising administering to the subject an effective amount of a compound provided herein.

Also provided are methods for increasing EAAT2 protein expression in a cell or a subject in need thereof, the method comprising contacting the cell or administering to the subject an effective amount of a compound provided herein.

Also provided are methods for activating the NRF2 pathway in a cell or a subject in need thereof, the method comprising contacting the cell or administering to the subject an effective amount of a compound provided herein.

As used herein, the phrase "effective amount" refers to the amount of active compound or pharmaceutical agent that elicits the biological or medicinal response that is being sought in a tissue, system, animal, individual or human by a researcher, veterinarian, medical doctor or other clinician. An effective amount of a compound provided herein can range, for example, from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

As used herein, to "treat" means to ameliorate at least one symptom of the disorder associated with glutamate excitotoxicity. Often, glutamate excitotoxicity results in neuronal cell death; thus, a treatment can result in a reduction in the rate or amount of neuronal cell death.

Combination Therapies

In some embodiments, the methods provided herein further comprise administering one or more additional therapeutic agents to the subject. In some embodiments, each of the one or more additional therapeutic agents is independently selected from the group consisting of a steroid, an anti-allergic agent, an anesthetic (e.g., for use in combination with a surgical procedure), an immunosuppressant, an anti-microbial agent, an anti-inflammatory agent, and a chemotherapeutic agent.

Example steroids include, but are not limited to, corticosteroids such as cortisone, dexamethasone, hydrocortisone, methylprednisolone, prednisolone, and prednisone.

Example anesthetics include, but are not limited to local anesthetics such as lidocaine, procain, and ropivacaine.

Example immunosuppressants include, but are not limited to, azathioprine, chlorambucil, cyclophosphamide, cyclosporine, daclizumab, infliximab, methotrexate, and tacrolimus.

Example anti-microbial agents include, but are not limited to, aminoglycosides (e.g., gentamicin, neomycin, and streptomycin), penicillins (e.g., amoxicillin and ampicillin), and macrolides (e.g., erythromycin).

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example chemotherapeutics include, but are not limited to, proteosome inhibitors (e.g., bortezomib), thalidomide, revlimid, and DNA-damaging agents such as melphalan, doxorubicin, cyclophosphamide, vincristine, etoposide, carmustine, and the like. For example, one or more of the following agents may be used in combination with the compounds provided herein and are presented as a non-limiting list: a cytostatic agent, cisplatin, taxol, etoposide, irinotecan, topotecan, paclitaxel, docetaxel, epothilones, tamoxifen, 5-fluorouracil, temozolomide, cyclophosphamide, gefitinib, erlotinib hydrochloride, imatinib mesylate, gemcitabine, uracil mustard, chlormethine, ifosfamide, chlorambucil, pipobroman, triethylenemelamine, triethylenethiophosphoramine, busulfan, lomustine, streptozocin, dacarbazine, floxuridine, cytarabine, 6-mercaptopurine, 6-thioguanine, fludarabine phosphate, oxaliplatin, folinic acid, pentostatin, vinblastine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methyltestosterone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, porfimer, erbitux, thiotepa, altretamine, trastuzumab, fulvestrant, exemestane, ifosfamide, rituximab, alemtuzumab, clofarabine, cladribine, aphidicolin, sunitinib, dasatinib, tezacitabine, triapine, trimidox, amidox, bendamustine, and ofatumumab.

Pharmaceutical Compositions

When employed as pharmaceuticals, the compounds provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral.

Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds provided herein, or a pharmaceutically acceptable salt thereof, are suitable for parenteral administration. In some embodiments, the compounds provided herein are suitable for intravenous administration. In some embodiments, the compounds provided herein are suitable for oral administration. In some embodiments, the compounds provided herein are suitable for topical administration.

Pharmaceutical compositions and formulations for topical administration may include, but are not limited to, transdermal patches, ointments, lotions, creams, gels, drops, suppositories, sprays, liquids and powders. Conventional pharmaceutical carriers, aqueous, powder or oily bases, thickeners and the like may be necessary or desirable. In some embodiments, the pharmaceutical compositions provided herein are suitable for parenteral administration. In some embodiments, the pharmaceutical compositions provided herein are suitable for intravenous administration. In some embodiments, the pharmaceutical compositions provided herein are suitable for oral administration. In some embodiments, the pharmaceutical compositions provided herein are suitable for topical administration.

Also provided are pharmaceutical compositions which contain, as the active ingredient, a compound provided herein in combination with one or more pharmaceutically acceptable carriers (e.g. excipients). In making the pharmaceutical compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be, for example, in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in an effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

The compositions provided herein can be administered one from one or more times per day to one or more times per week; including once every other day. The skilled artisan will appreciate that certain factors can influence the dosage and timing required to effectively treat a subject, including, but not limited to, the severity of the disease or disorder, previous treatments, the general health and/or age of the subject, and other diseases present. Moreover, treatment of a subject with a therapeutically effective amount of a compound described herein can include a single treatment or a series of treatments.

Dosage, toxicity and therapeutic efficacy of the compounds provided herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

Compounds exhibiting high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Preparation of Compounds

Synthesis of Compound 100: 2-(2-(dimethylamino)ethyl)-6-(pyridin-2-yl)pyridazin-3(2H)-one

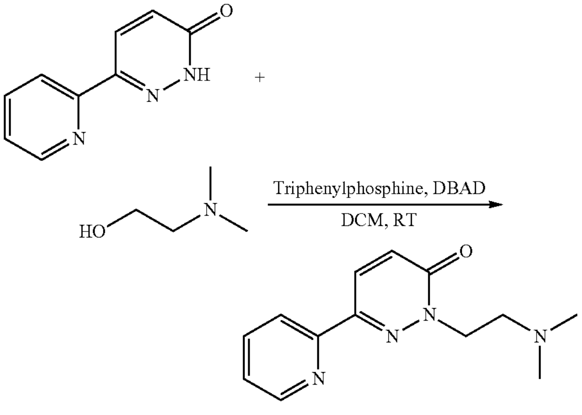

100

A flask was charged with triphenylphosphine (1.83 g, 7 mmol) and di-tert-butylazadicarboylate (1.21 g, 5.25 mmol). The flask was degassed with argon, then the solids dissolved in DCM (20 mL) at 0° C. A separate flask was charged with 6-(pyridin-2-yl)pyridazin-3(2H)-one (600 mg, 3.5 mmol). To the solid was added DCM (15 mL) and N,N-dimethylethanolamine (0.42 mL, 4.2 mmol). After 20 minutes the triphenylphosphine and di-tert-butyl-butylazadicarboylate solution was added dropwise to the slurry of 6-(pyridin-2-yl)pyridazin-3(2H)-one and N,N-dimethylethanolamine. After 3 hours at room temperature the reaction was concentrated, reconstituted in toluene (35 mL), then concentrated again. The crude was reconstituted in ethyl acetate (35 mL), filtered, and then 1.7 mL of 2M HCl in diethyl ether was added at once to the filtrate. The slurry was stirred at 0° C. for 15 minutes, briefly chilled at −78° C., then the solid was collected by vacuum filtration. The solid was recrystallized with an ethanol:ethyl acetate solution and then filtered to give the mono-hydrochloride salt of 2-(2-(dimethylamino) ethyl)-6-(pyridin-2-yl)pyridazin-3(2H)-one (330 mg, 34%) as a white solid.

$^1$H NMR (400 MHz, DMSO): 10.78 (s, 1H), 8.67 (m, 1H), 8.27 (d, J=4 Hz 1H), 8.13 (d, J=8 Hz 1H), 7.94 (td, J=7.8, 1.2 Hz 1H), 7.48 (m, 1H), 7.12 (d, J=10 Hz 1H), 4.59 (m, 2H), 3.56 (m, 2H), 2.82 (s, 6H). $[M+1]^+$=245.1

A sample of the mono-hydrochloride salt of 2-(2-(dimethylamino)ethyl)-6-(pyridin-2-yl)pyridazin-3(2H)-one was recrystallized ethanol:ethyl acetate and X-ray analysis confirmed the structure as shown in FIG. 1A.

Synthesis of Compound 101: 2-(2-(Methylamino)ethyl)-6-(pyridin-2-yl)pyridazin-3(2H)-one hydrochloride

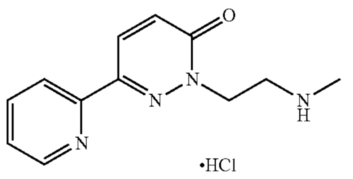 [SMILES: CNCCn1nc(-c2ccccn2)ccc1=O ; Cl]

6-(Pyridin-2-yl)pyridazin-3(2H)-one (5 g, 29 mmol), triphenylphosphine (15.1 g, 57 mmol), and di-tert-butyl azodicarboxylate (10.01 g, 43 mmol) were placed into a 500 mL flask and dissolved in DCM (250 mL). To the stirred solution was added dropwise 2-methylaminoethanol (2.79 mL). After 4 hours stirring at room temperature, LCMS indicated the reaction was complete and the mixture concentrated under reduced pressure. The residue was purified by chromatography DCM/methanol/$NH_3$ (95/4/1) solvent system to give a light orange oil (4.9 g). The oil was dissolved in ethyl acetate (~250 mL) and then the salt was generated with 2M HCl in ether (12.5 mL). The solid was collected by vacuum filtration to give the product as a white powder (4.6 g).

$^1$H NMR (400 MHz, DMSO): 9.25 (s, 2H), 8.67 (m, 1H), 8.30 (d, J=4 Hz 1H), 8.20 (d, J=8 Hz 1H), 7.99 (td, J=8, 1 Hz 1H), 7.49 (m, 1H), 7.10 (d, J=10 Hz 1H), 4.47 (m, 2H), 3.35 (m, 2H), 2.56 (s, 3H). $[M+1]^+$=231

Figure 1B:
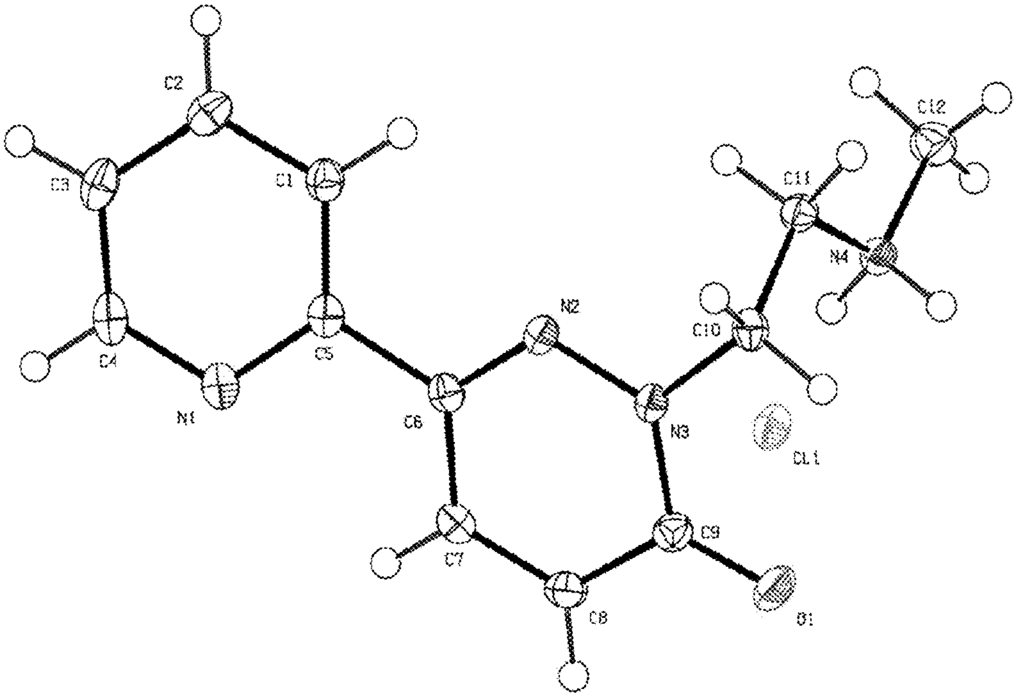
FIG. 1B shows the crystal structure of Compound 101.

A sample of the mono-hydrochloride salt of 2-(2-(methylamino)ethyl)-6-(pyridin-2-yl)pyridazin-3(2H)-one was recrystallized ethyl acetate:hexane and X-ray analysis confirmed the structure as shown in FIG. 1B.

The following compounds were prepared in a similar manner as Compound 100 (2-(2-(dimethylamino)ethyl)-6-(pyridin-2-yl)pyridazin-3(2H)-one).

Compound 181: 2-Isopentyl-6-(pyridin-2-yl) pyridazin-3(2H)-one

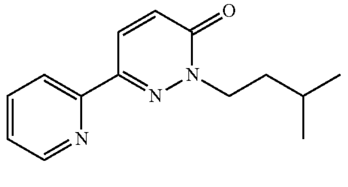 [SMILES: CC(C)CCn1nc(-c2ccccn2)ccc1=O]

$^1$H NMR 400 Hz (CDCl3): δ 8.50 (d, 1H, J=3.6 Hz), 8.32 (d, 1H, J=9.6 Hz), 8.14 (d, 1H, J=8 Hz), 7.79 (td, 1H, J=2 and 8 Hz), 7.32-7.30 (m, 1H), 7.01 (d, 1H, J=7.6 Hz), 4.30-4.27 (m, 2H), 1.80-1.75 (m, 2H), 1.72-1.67 (m, 1H), 1.00 (d, 6H, J=5.2 Hz). $[M+1]^+$=244

Compound 126: 2-(2-Morpholinoethyl)-6-(pyridin-2-yl)pyridazin-3(2H)-one hydrochloride

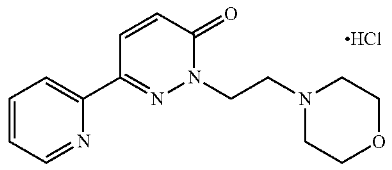 [SMILES: O=c1ccc(-c2ccccn2)nn1CCN1CCOCC1 ; Cl]

$^1$H NMR 400 Hz (DMSO): δ 11.47 (s, 1H) 8.70 (d, 1H, J=3.6 Hz), 8.31 (d, 1H, J=10 Hz), 8.17 (d, 1H, J=6.8 Hz), 8.01 (td, 1H, J 1.2 and 6.2 Hz), 7.54-7.51 (m, 1H), 7.13 (d, 1H, J=8 Hz), 4.61 (t, 2H, 5.2 Hz), 3.96 (d, 2H, 9.2 Hz), 3.81 (t, 2H, J=9.6 Hz), 3.63 (s, 2H), 3.56 (d, 2H, J=9.6 Hz), 3.17-3.16 (m, 2H), 2.50 (m, 1H). $[M+1]^+$=287

Compound 198: 6-(Pyridin-2-yl)-2-(1-(pyridin-2-yl) ethyl)pyridazin-3(2H)-one

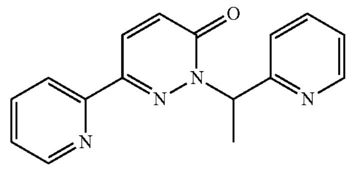

$^1$H NMR 400 Hz (CDCl3): δ 8.60-8.57 (m, 2H), 8.33 (d, 1H, J=9.6 Hz), 8.04 (d, 1H, J=8 Hz), 7.72 (td, 1H, J1=1.6 and 7.8 Hz), 7.62 (td, 1H, J1=2 and 7.6 Hz) 7.29-7.25 (m, 2H), 7.16 (dd, 1H, J=1.2 and 5 Hz), 7.10 (d, 1H, J=9.6 Hz), 6.43 (q, 1H, J=7.2 Hz), 1.93 (d, 3H, J=6.8 Hz). $[M+1]^+$=279

Compound 145: 6-(pyridin-2-yl)-2-(thiazol-2-ylmethyl)pyridazin-3(2H)-one

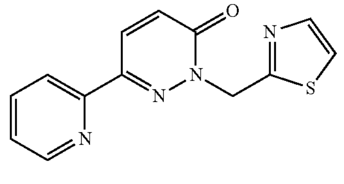 [SMILES: O=c1ccc(-c2ccccn2)nn1Cc1nccs1]

$^1$H NMR 400 Hz (CDCl3): δ 8.61 (d, 1H J=4.8 Hz), 8.38 (d, 1H, J=9.6 Hz), 8.15 (d, 1H, J=8 Hz), 7.76 (Td, 1H, J=2 and 9.4 Hz), 7.76 (s, 1H), 7.32 (d, 1H, J=3.6 Hz), 7.30 (Dd, 1H, J=1.2 and 2.6 Hz), 7.07 (d, 1H, J=9.6 Hz), 5.74 (s, 2H). $[M+1]^+$=271

Compound 199: 2-Methyl-6-(pyridin-2-yl)pyridazin-3(2H)-one

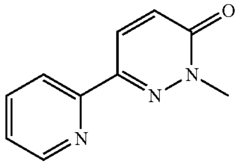

$^1H$ NMR 400 Hz (CDCl3): δ 8.62 (d, 1H, J=4.8 Hz), 8.33 (d, 1H, J=10 Hz), 8.12 (d, 1H, J=8.4 Hz), 7.77 (td, 1H, J1=1.6 and 7.8 Hz), 7.32-7.28 (m, 1H), 7.02 (d, 1H, J=9.6 Hz), 3.88 (s, 3H).

Compound 166: 2-(3-(Dimethylamino)propyl)-6-(pyridin-2-yl)pyridazin-3(2H)-one hydrochloride

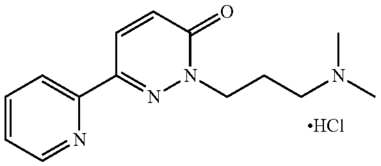 [SMILES: CN(C)CCCn1nc(-c2ccccn2)ccc1=O ; Cl]

$^1H$ NMR 400 Hz (DMSO): δ 10.71 (s, 1H) 8.67 (d, 1H, J=4.4 Hz), 8.29 (d, 1H, J=10 Hz), 8.15 (d, 1H, J=8 Hz), 7.97 (td, 1H, J 1.2 and 6.2 Hz), 7.51-7.51 (m, 1H), 7.09 (d, 1H, J=9.6 Hz), 4.22 (t, 2H, J=6.8 Hz), 3.14-3.08 (m, 2H), 2.70 (d, 6H, J=5.2 Hz), 2.25-2.17 (m, 2H). $[M+1]^+$=259

Compound 146: 2-(Oxazol-2-ylmethyl)-6-(pyridin-2-yl)pyridazin-3(2H)-one

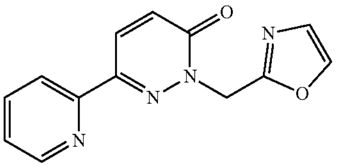 [SMILES: O=c1ccc(-c2ccccn2)nn1Cc1ncco1]

$^1H$ NMR 400 Hz (CDCl3): δ 8.61 (d, 1H J=4.8 Hz), 8.39 (d, 1H, J=9.6 Hz), 8.06 (d, 1H, J=8 Hz), 7.74 (td, 1H, J=2 and 9.4 Hz), 7.64 (s, 1H), 7.31-7.28 (m, 1H), 7.11 (s, 1H) 7.07 (d, 1H, J=9.6 Hz), 5.55 (s, 2H). $[M+1]^+$=232

Compound 172: 2-(2-Methoxyethyl)-6-(pyridin-2-yl)pyridazin-3(2H)-one

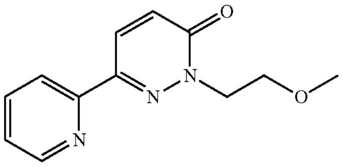 [SMILES: COCCn1nc(-c2ccccn2)ccc1=O]

$^1H$ NMR 400 Hz (CDCl3): δ8.72 (d, 1H, J=3.6 Hz), 8.31 (d, 1H, J=9.6 Hz), 8.10 (d, 1H, J=8 Hz), 7.89 (td, 1H, J=2 and 8 Hz), 7.43-7.40 (m, 1H), 7.14 (d, 1H, J=9.6 Hz), 4.49 (t, 2H, J=5.6 Hz), 3.89 (t, 2H, J=5.6 Hz), 3.38 (s, 3H). $[M+1]^+$=232

Compound 105: 2-(2-(Diethylamino)ethyl)-6-(pyridin-2-yl)pyridazin-3(2H)-one hydrochloride

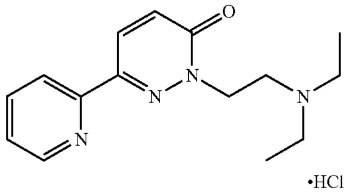 [SMILES: CCN(CC)CCn1nc(-c2ccccn2)ccc1=O ; Cl]

$^1H$ NMR 400 Hz (DMSO): δ 10.37 (s, 1H) 8.68 (d, 1H, J=4.4 Hz), 8.31 (d, 1H, J=10 Hz), 8.15 (d, 1H, J=8 Hz), 7.98 (td, 1H, J=1.2 and 6.2 Hz), 7.51-7.48 (m, 1H), 7.13 (d, 1H, J=9.6 Hz), 4.54 (t, 2H, J=6.4 Hz), 3.55-3.50 (m, 2H), 3.23-3.19 (m, 4H).

Compound 110: 2-(2-(Methyl(phenyl)amino)ethyl)-6-(pyridin-2-yl)pyridazin-3(2H)-one

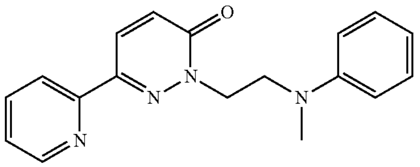 [SMILES: CN(CCn1nc(-c2ccccn2)ccc1=O)c1ccccc1]

$^1H$ NMR 400 Hz (DMSO): δ 8.65 (d, 1H, J=4.8 Hz), 8.18 (d, 1H, J=9.6 Hz), 8.04 (d, 1H, J=8 Hz), 7.97 (t, 1H, J=8 Hz), 7.49 (t, 1H, J=6.4 Hz), 7.14-7.11 (m, 2H), 6.98 (d, 1H, J=9.6 Hz), 6.92 (s, 2H), 6.70 (s, 1H), 4.35 (t, 2H, J=6.4 Hz), 3.86 (t, 2H, J=6.4 Hz), 2.93 (s, 3H). $[M+1]^+$=307

Compound 102: 2-(2-Aminoethyl)-6-(pyridin-2-yl)pyridazin-3(2H)-one hydrochloride

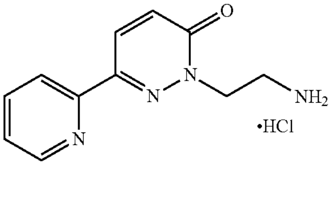 [SMILES: NCCn1nc(-c2ccccn2)ccc1=O ; Cl]

$^1H$ NMR 400 Hz (DMSO): δ 8.69-8.68 (m, 1H), 8.31 (d, 1H, J=10 Hz), 8.17-8.15 (m, 1H), 7.96 (td, 1H, J=2 and 8 Hz), 7.50-7.47 (m, 1H), 7.12 (d, 1H, J=9.6 Hz), 4.41 (t, 2H, J=7.2 Hz), 3.28 (t, 3H, J=6 Hz). $[M+1]^+$=217

Compound 200: 6-(6-Azidopyridin-2-yl)-2-(2-(Methyl(Prop-2-Yn-1-yl)amino)ethyl)pyridazin-3(2H)-one

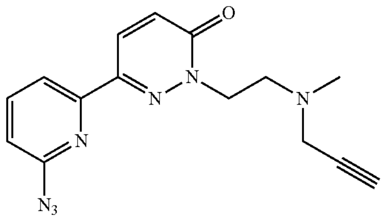

$^1$H NMR 400 Hz (MeOD): δ 8.44 (d, 1H, J=10 Hz), 8.20 (d, 1H, J=8.8 Hz), (m, 1H), 7.97 (dd, 1H, J=7.2 and 9.2 Hz), 7.87-7.82 (m, 1H), 7.17 (d, 1H, J=9.6 Hz), 3.47-4.35 (m, 2H), 3.05-2.99 (m, 2H), 2.64-2.61 (m, 1H), 2.401 (s, 6H).

Compound 133: 2-(2-(2-Oxopyrrolidin-1-yl)ethyl)-6-(pyridin-2-yl)pyridazin-3(2H)-one

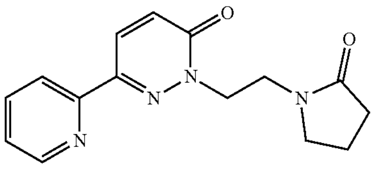 [SMILES: O=C1CCCN1CCn1nc(-c2ccccn2)ccc1=O]

$^1$H NMR 400 Hz (DMSO): δ 8.65 (d, 1H, J=4.4 Hz), 8.24 (d, 1H, J=10 Hz), 8.07 (d, 1H, J=8 Hz), 7.94 (td, 1H, J=1.2 and 8 Hz), 7.46-7.43 (m, 1H), 7.01 (d, 1H, J=10 Hz), 4.28 (t, 2H, J=5.6 Hz), 3.61 (t, 2H, J=5.2 Hz), 3.40 (t, 2H, J=6.8 Hz), 1.99-1.95 (m, 2H), 1.86-1.78 (m, 2H). $[M+1]^+$=285

Compound 201: 2-(2-(1-Methyl-1H-imidazol-2-yl)ethyl)-6-(pyridin-2-yl)pyridazin-3(2H)-one

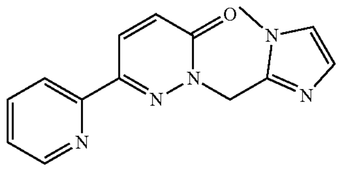 [SMILES: Cn1ccnc1Cn1nc(-c2ccccn2)ccc1=O]

$^1$H NMR 400 Hz (DMSO): δ 8.64 (d, 1H, J=4.4 Hz), 8.28 (d, 1H, J=9.6 Hz), 7.92-7.90 (m, 2H), 7.45-7.42 (m, 1H), 7.10 (s, 1H), 7.08 (d, 1H, J=9.6 Hz), 6.77 (s, 1H), 5.38 (s, 2H), 3.72 (s, 3H). $[M+1]^+$=268

Synthesis of Compound 202: 2-(2-(Dimethylamino)ethyl)-6-(pyridin-2-yl)pyridazine-3(2H)-thione

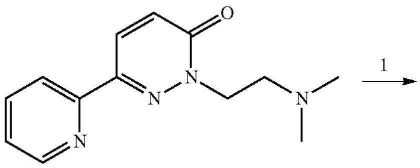

-continued

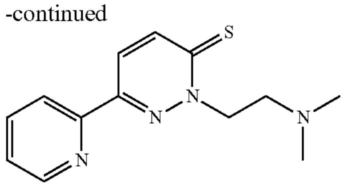

Step 1: To 2-(2-(dimethylamino)ethyl)-6-(pyridin-2-yl)pyridazin-3(2H)-one (100 mg, 0.4 mmol) in pyridine (3 mL) was added phosphorus pentasulfide (182 mg, 0.41 mmol). The mixture was heated at 100° C. for 18 hours. The mixture was evaporated and partitioned between 1M sodium hydroxide (5 mL) and extracted with 20% IPA in dichloromethane (3×10 mL). The combined extracts were dried ($MgSO_4$) and evaporated to give the title compound, 2-(2-(dimethylamino)ethyl)-6-(pyridin-2-yl)pyridazine-3(2H)-thione as a yellow solid (87 mg).

$^1$H NMR 400 Hz (CDCl3): δ 8.66 (d, 1H, J=3.2 Hz), 8.17 (d, 1H, J=8 Hz), 8.06 (d, 1H, J=9.2 Hz), 7.89 (d, 1H, J=8.4 Hz), 7.81 (td, 1H, J=2 and 8 Hz), 7.37-7.34 (m, 1H), 4.93 (t, 2H, J=7.2 Hz), 2.95 (t, 2H, J=7.2 Hz), 2.37 (s, 6H).

Synthesis of Compound 195: 2-(2-(Dimethylamino)ethyl)-4-Methyl-6-(pyridin-2-yl)pyridazin-3(2H)-one hydrochloride

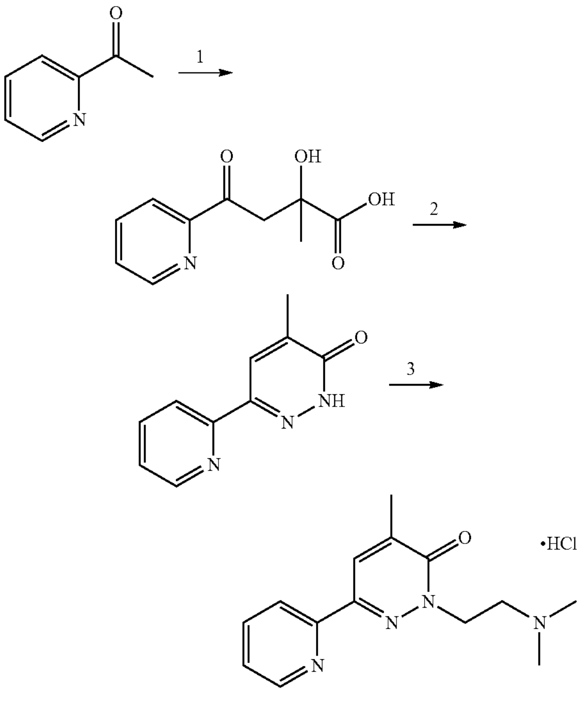

Step 1.

A flask was charged with potassium hydroxide (0.074 mol). The solid was dissolved in water, then acetylpyridine (0.0166 mol) was added at once. The solution was stirred for 30 minutes, and then pyruvic acid was added at once (0.02475 mol). After 3 hours of stirring, additional pyruvic acid was added (0.02475 mol). After 3 hours the pH was adjusted to 2 with 12 M HCl. The aqueous was extracted 10× with 10 mL of a 20% isopropanol in dichloromethane solution (total 100 mL), dried over anhydrous sodium sulfate, then concentrated under reduced pressure. The oil was treated with 2M ammonia in methanol, concentrated, then triturated with ethyl acetate to give an oily solid. The solid was dried under reduced pressure to give 2-hydroxy-2-methyl-4-oxo-4-(pyridin-2-yl)butanoate as an orange powder (2.2 g, 63%) which was used in the next step.

Step 2.

A flask was charged with the crude solid 2-hydroxy-2-methyl-4-oxo-4-(pyridin-2-yl)butanoate (0.0105 mol). The powder was dissolved in water, and then acetic acid (0.05 mol) and hydrazine monohydrate (0.021 mol) were added at once. After 2 days of stirring at 80° C., the reaction was chilled to 0° C. and the product was collected by vacuum filtration to give 4-methyl-6-(pyridin-2-yl)pyridazin-3(2H)-one as a tan solid (800 mg, 26%) which was used in the next step.

Step 3.

A vial was charged with triphenylphosphine (0.75 mmol) and di-tert-butyl azodicarboxylate (0.56 mmol). The solids were added to a solution of 4-methyl-6-(pyridin-2-yl) pyridazin-3(2H)-one (0.37 mmol) in dichloromethane (3.5 mL), and then N,N-dimethylethanoloamine (0.45 mol) was added at once. After an hour of stirring the reaction was concentrated under reduced pressure and purified on a 20 g silica gel column with a dichloromethane:methanol (1% $NH_3$) solvent system. The desired product eluted from 5-9% methanol. Fractions were concentrated to give a yellow oil. The oil was dissolved in ethyl acetate, and then acidified with 2M HCl in diethyl ether (0.6 mL). The resulting salt was collected by vacuum filtration to give the title compound as a white solid (168 mg, 53%).

$^1H$ NMR 400 Hz (DMSO): δ 10.48 (s, 1H) 8.66 (d, 1H, J=4.8 Hz), 8.21 (d, 1H, J=1.2 Hz), 8.14 (d, 1H, J=8 Hz), 7.96 (td, 1H, J=1.2 and 6.2 Hz), 7.49-7.47 (m, 1H), 4.54 (t, 2H, J=6.4 Hz), 3.57-3.56 (m, 2H), 2.83 (d, 6H, J=4.4 Hz), 2.19 (s, 3H). $[M+1]^+$=259

Synthesis of Compound 196: N,N-2-(2-(dimethylamino)ethyl)-5-methyl-6-(pyridin-2-yl)pyridazin-3(2H)-one hydrochloride

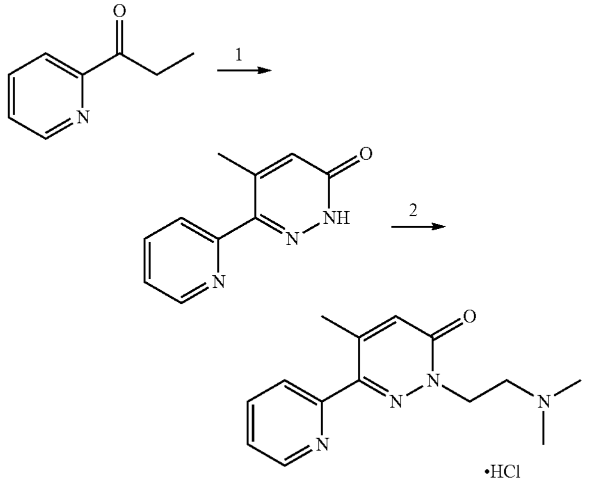

Step 1.

A flask was charged with potassium carbonate (8.8 mmol). The solid was dissolved in water, then 1-(pyridin-2-yl)propan-1-one (4.4 mmol) was added at once. The solution was stirred for 30 minutes, and then glyoxylic acid was added at once (4.4 mmol). After stirring overnight, the reaction was acidified with acetic acid (17.6 mmol), then hydrazine monohydrate was added in one portion (8.8 mmol). The reaction was stirred for 6 days, with an additional 2 mL of acetic acid added every 2 days. The reaction was partially concentrated under reduced pressure, then extracted with 20% isopropanol in dichloromethane, dried over anhydrous sodium sulfate, then concentrated under reduced pressure to give 5-methyl-6-(pyridin-2-yl) pyridazin-3(2H)-one as a solid (800 mg).

Step 2.

A flask was charged with triphenylphosphine (8.6 mmol), di-tert-butyl azodicarboxylate (6.5 mmol), and 5-methyl-6-(pyridin-2-yl)pyridazin-3(2H)-one (4.3 mmol). The solids were dissolved in dichloromethane, and then N,N-dimethylethanoloamine (5.2 mmol) was added at once. After 4 hours, the reaction was concentrated under reduced pressure, reconstituted in ethyl acetate, and then acidified with 1 eq 2M HCL in diethyl ether. The resulting salt was collected by vacuum filtration. The salt was dissolved in 3M HCl (8.2 mmol) and stirred at 90° C. overnight. After a night of stirring the solution was cooled to 0° C., then solid NaOH was added (13.7 mmol). The aqueous was extracted a solution of 20% isopropanol in DCM, dried over anhydrous sodium sulfate and concentrated. The residue was purified by ISCO silica flash chromatography using a dichloromethane:methanol solvent system. The desired product eluted at 10% methanol. Fractions containing the desired product were concentrated, reconstituted in ethyl acetate, and then the hydrochloride salt was generated using 1 eq of 2M HCl in diethyl ether. The salt was collected by vacuum filtration to give a tan solid (70 mg).

$^1H$ NMR 400 Hz (DMSO): δ 10.21 (s, 1H) 8.67 (d, 1H, J=5.2 Hz), 7.99 (t, 1H, J=7.6 Hz), 7.81 (d, 1H, J=8 Hz), 7.52-7.49 (m, 1H), 4.46 (t, 2H, J=6.4 Hz), 3.53-3.49 (m, 2H), 2.82 (d, 6H, J=4.8 Hz), 2.30 (s, 3H). $[M+1]^+$=259

Synthesis of Compound 118: 2-(6-Oxo-3-(pyridin-2-yl)pyridazin-1(6H)-yl)-N-phenylacetamide

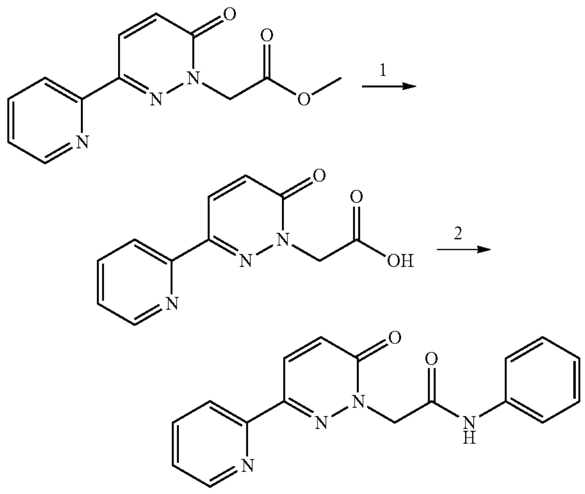

Step 1.

Methyl 2-(6-oxo-3-(pyridin-2-yl)pyridazin-1(6H)-yl)acetate (prepared by the representative procedure described above and using methyl glycolate) (5.8 mmol) was dissolved in a 1:1 solution of water and THF. Then, 15 mL of 3M NaOH was added to the cloudy suspension and stirred at room temperature. After 1.5 hours the tan slurry was partially concentrated, then washed 3× with ethyl acetate and once with DCM. The aqueous layer was adjusted to pH 1, then extracted with a 20% solution of isopropanol in dichloromethane. The organics were dried over anhydrous sodium sulfate, then concentrated under reduced pressure to give 2-(6-oxo-3-(pyridin-2-yl)pyridazin-1(6H)-yl)acetic acid as an orange-white solid (400 mg, 30%).

Step 2.

2-(6-Oxo-3-(pyridin-2-yl)pyridazin-1(6H)-yl)acetic acid (0.87 mmol), EDC HCl (1.30 mmol), and HATU (1.3 mmol) were placed into a vial and dissolved in DMF. Aniline (1.3 mmol) was added at once. The reaction was stirred for 2 days, then quenched with water. The resulting slurry was filtered to give the title compound as a white solid (83 mg, 31%).M+1=307.3.

The following compounds were prepared in a similar manner as Compound 118 (2-(6-oxo-3-(pyridin-2-yl) pyridazin-1(6H)-yl)-N-phenylacetamide).

Compound 120: 2-(6-Oxo-3-(pyridin-2-yl) pyridazin-1(6H)-yl)-N-(pyridin-2-yl)Acetamide

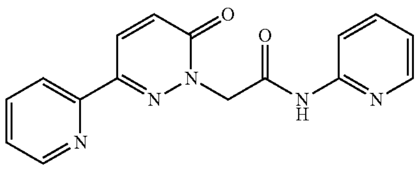 [SMILES: O=C(Cn1nc(-c2ccccn2)ccc1=O)Nc1ccccn1]

$^1$H NMR 400 Hz (DMSO): δ 10.90 (s, 1H) 8.67 (d, 1H, J=4.8 Hz), 8.35-8.32 (m, 2H), 8.06 (d, 1H, J=8 Hz), 7.99-7.90 (m, 2H), 7.78-7.74 (m, 1H), 7.47-7.45 (m, 1H), 7.13-7.09 (m, 2H), 5.07 (s, 2H).

Compound 203: N-(2-(2-(Dimethylamino)ethoxy) phenyl)-2-(6-Oxo-3-(pyridin-2-yl)pyridazin-1(6H)-yl)Acetamide

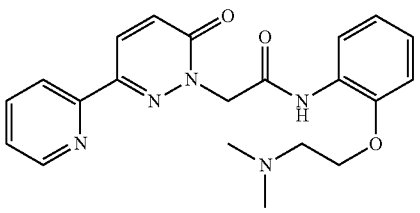 [SMILES: CN(C)CCOc1ccccc1NC(=O)Cn1nc(-c2ccccn2)ccc1=O]

$^1$H NMR 400 Hz (DMSO): δ10.46 (s, 1H), 9.76 (s, 1H), 8.68 (d, 1H, J=4 Hz), 8.34 (d, 1H, J=9 Hz), 8.07 (d, 1H, J=8 Hz) 7.94 (td, 1H, J=1.6 and 8 Hz), 7.49-7.46 (m, 2H), 7.25 (t, 1H, d=8 Hz), 7.12 (d, 1H, J=9.6 Hz), 7.07-7.05 (m, 1H), 6.71 (dd, 1H, J=2 and 8.2 Hz), 5.00 (s, 2H), 4.26 (t, 2H, J=5.2 Hz), 3.49-3.45 (m, 2H), 2.81 (d, 6H, J=4.8 Hz). $[M+1]^+$=394

Compound 121: N-(2-Fluorophenyl)-2-(6-Oxo-3-(pyridin-2-yl)pyridazin-1(6H)-yl)Acetamide

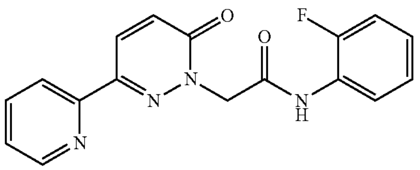 [SMILES: O=C(Cn1nc(-c2ccccn2)ccc1=O)Nc1ccccc1F]

$^1$H NMR 400 Hz (DMSO): δ 10.18 (s, 1H), 8.67 (d, 1H, J=4 Hz), 8.33 (d, 1H, J=9.6 Hz), 8.07 (d, 1H, J=8 Hz), 7.95-7.87 (m, 2H), 7.46 (dd, 1H, J1=1.2 and 5 Hz), 7.29-7.23 (m, 1H), 7.15-7.10 (m, 3H), 5.07 (s, 2H).

Compound 114: N-Methyl-2-(6-Oxo-3-(pyridin-2-yl)pyridazin-1(6H)-yl)Acetamide

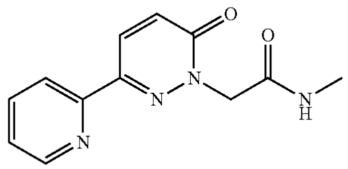 [SMILES: CNC(=O)Cn1nc(-c2ccccn2)ccc1=O]

$^1$H NMR 400 Hz (CDCl3): δ8.64-8.63 (m, 1H), 8.44 (d, 1H, J=9.6 Hz), 8.16 (d, 1H, J=8 Hz), 7.78 (td, 1H, J=2 and 8 Hz), 7.34-7.31 (m, 1H), 7.10 (d, 1H, J=9.6 Hz), 4.94 (s, 2H), 2.82 (d, 3H, J=4.8 Hz).

Compound 115: 2-(6-Oxo-3-(pyridin-2-yl) pyridazin-1(6H)-yl)Acetamide

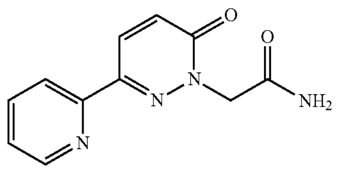 [SMILES: NC(=O)Cn1nc(-c2ccccn2)ccc1=O]

$^1$H NMR 400 Hz (CDCl3): δ8.64-8.63 (m, 1H), 8.44 (d, 1H, J=9.6 Hz), 8.16 (d, 1H, J=8 Hz), 7.78 (td, 1H, J=2 and 8 Hz), 7.34-7.31 (m, 1H), 7.10 (d, 1H, J=9.6 Hz), 4.94 (s, 2H).

Compound 123: N-Methyl-3-(6-Oxo-3-(pyridin-2-yl)pyridazin-1(6H)-yl)Propanamide

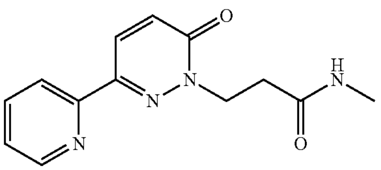 [SMILES: CNC(=O)CCn1nc(-c2ccccn2)ccc1=O]

$^1$H NMR 400 Hz (CDCl3): δ8.63-8.61 (m, 1H), 8.3 (d, 1H, J=9.6 Hz), 8.12 (d, 1H, J=8 Hz), 7.78 (td, 1H, J=2 and 8 Hz), 7.33-7.25 (m, 1H), 7.03 (d, 1H, J=9.6 Hz), 4.57 (t, 2H, J=7.2 Hz), 2.82-2.78 (m, 5H). $[M+1]^+$=259

Compound 124: 3-(6-Oxo-3-(pyridin-2-yl) pyridazin-1(6H)-yl)propanamide

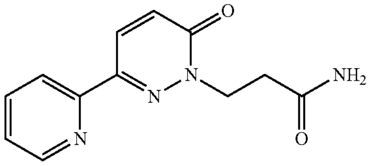 [SMILES: NC(=O)CCn1nc(-c2ccccn2)ccc1=O]

$^1$H NMR 400 Hz (CDCl3): δ8.65-8.64 (m, 1H), 8.26 (d, 1H, J=9.6 Hz), 8.11 (d, 1H, J=8 Hz), 7.91 (td, 1H, J=2 and 8 Hz), 7.46-7.43 (m, 1H), 7.04 (d, 1H), 4.33-4.29 (m, 1H), 2.63-2.60 (m, 2H).

Synthesis of Compound 204: 2-(2-(Dimethylamino) ethyl)-6-Phenylpyridazin-3(2H)-one hydrochloride

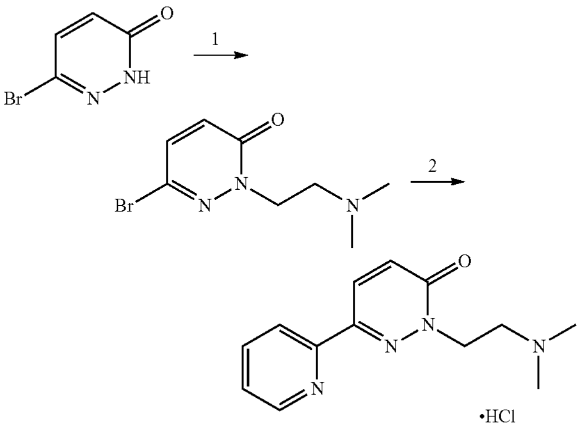

Step 1.

6-Bromopyridazin-3(2h)-one (0.57 mmol), triphenylphosphine (1.14 mmol), and di-tert-butyl azodicarboxylate (0.855 mmol) were placed in a vial and dissolved in dichloromethane. N,N-dimethylethanolamine (0.684 mmol) was added at once. After stirring overnight, the reaction was concentrated. The residue was purified by ISCO silica flash chromatography using a dichloromethane:methanol solvent system. The desired product eluted at 8% methanol. Fractions containing the desired product were concentrated to give 6-bromo-2-(2-(dimethylamino)ethyl)pyridazin-3(2H)-one as a white solid (60 mg, 42%).

Step 2.

6-Bromo-2-(2-(dimethylamino)ethyl)pyridazin-3(2H)-one (0.244 mmol), phenyl boronic acid pinacol ester (0.41 mmol), and sodium carbonate (1 mmol) were placed in a vial and degassed with argon. Tetrakis(triphenylphosphine)palladium(0) (5 mol %) was then added, and the vial was degassed with argon once again. The solid were dissolved in acetonitrile/water (15% water). The reaction was heated to 60° C. and stirred overnight. The reaction was quenched with brine, extracted with ethyl acetate, dried over anhydrous sodium sulfate, and then concentrated under reduced pressure. The crude was purified by ISCO silica flash chromatography using a dichloromethane:methanol solvent system. The desired product eluted at 1% methanol. Fractions were concentrated to give a clear oil. The oil was reconstituted in ethyl acetate, then the salt was generated using 1 eq of 2M HCl in diethyl ether. The salt was collected by filtration to give the title a white powder (21 mg, 35%).

$^1$H NMR 400 Hz (DMSO): δ10.08 (s, 1H) 8.08 (d, 1H, J=9.6 Hz), 7.92-7.89 (m, 2H), 7.52-7.46 (m, 3H), 7.10 (d, 1H, J=10 Hz), 4.51-4.48 (m, 2H), 3.54 (m, 2H), 2.84 (s, 6H). $[M+1]^+$=244

The following compounds were prepared in a similar manner as Compound 204 (2-(2-(dimethylamino)ethyl)-6-phenylpyridazin-3(2H)-one hydrochloride):

Compound 205: 2-(2-(Dimethylamino)ethyl)-6-(2-Fluorophenyl)pyridazin-3(2H)-one hydrochloride

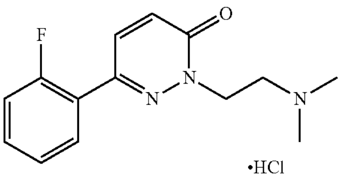 [SMILES: CN(C)CCn1nc(-c2ccccc2F)ccc1=O ; Cl]

$^1$H NMR 400 Hz (MeOD): δ7.89-7.86 (m, 1H), 7.79 (dt, 1H, J=2 and 7.8 Hz), 7.54-7.49 (m, 1H), 7.34-7.23 (m, 2H), 7.12 (d, 1H, J=10 Hz), 7.12 (d, 1H, J=9.6 Hz), 4.67-4.64 (m, 2H), 3.71-3.68 (m, 2H), 3.02 (s, 6H).

Compound 206: 2-(2-(Dimethylamino)ethyl)-6-(2-methoxyphenyl)pyridazin-3(2H)-one hydrochloride

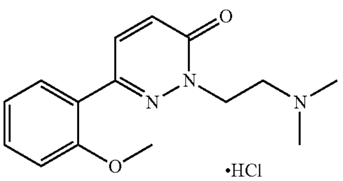 [SMILES: COc1ccccc1-c1ccc(=O)n(CCN(C)C)n1 ; Cl]

$^1$H NMR 400 Hz (DMSO): δ 10.13 (s, 1H), 7.75 (d, 1H, J=9.6 Hz), 7.54 (dd, 1H, J=1.6 and 7.6 Hz), 7.45 (td, 1H, J=1.6 and 7.6 Hz), 7.15 (d, 1H, J=8 Hz), 7.04 (t, 1H, J=7.6 Hz), 6.98 (d, 1H, J=9.6 Hz), 4.46 (t, 2H, J=6 Hz), 3.81 (s, 3H), 3.51 (q, 2H, J=5.6 Hz), 2.83 (d, 6H, J=4.8 Hz). $[M+1]^+$=274

Compound 207: 2-(2-(Dimethylamino)ethyl)-6-(3-methoxyphenyl)pyridazin-3(2H)-one hydrochloride

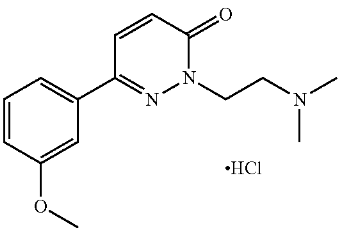 [SMILES: COc1cccc(-c2ccc(=O)n(CCN(C)C)n2)c1 ; Cl]

$^1$H NMR 400 Hz (DMSO): δ 10.67 (s, 1H), 8.07 (d, 1H, J=10 Hz), 7.48-7.38 (m, 3H), 7.06 (d, 1H, J=9.6 Hz), 7.03 (dd, 1H, J=2.4 and 7.6 Hz), 4.51 (t, 2H, J=6 Hz), 3.81 (s, 3H), 3.52 (q, 2H, J=5.6 Hz), 2.82 (d, 6H, J=5.2 Hz). $[M+1]^+$=274

Compound 208: 2-(2-(Dimethylamino)ethyl)-6-(4-methoxyphenyl)pyridazin-3(2H)-one hydrochloride

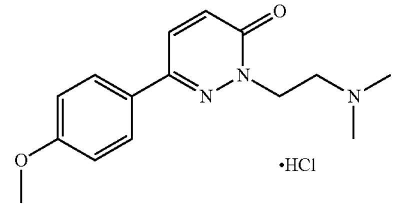 [SMILES: COc1ccc(-c2ccc(=O)n(CCN(C)C)n2)cc1 ; Cl]

$^1$H NMR 400 Hz (DMSO): δ 10.70 (s, 1H), 8.02 (d, 1H, J=10 Hz), 7.85 (d, 2H, J=8.8 Hz), 7.05-7.01 (m, 3H), 4.50 (m, 2H), 3.79 (s, 3H), 3.51 (q, 2H, J=6 Hz), 2.81 (d, 6H, J=5.2 Hz). $[M+1]^+$=274

Synthesis of Compound 209: 2-(2-(Methylamino)ethyl)-6-(thiazol-2-yl)pyridazin-3(2H)-one hydrochloride

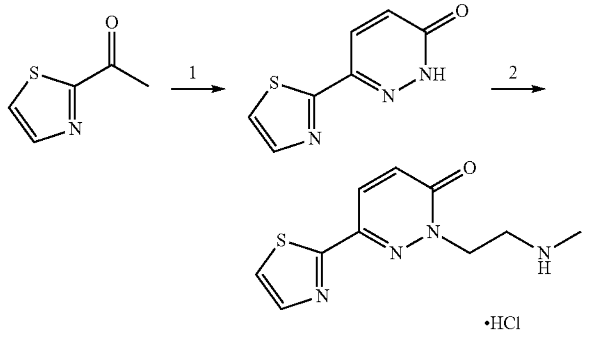

Step 1.

A flask was charged with potassium carbonate (1.04 g, 7.8 mmol). The solid was dissolved in water, then 2-acetylthiazole (0.5 g, 4 mmol) was added at once. The solution was stirred for 30 minutes, and then glyoxylic acid (363 mg, 4.0 mmol) was added at once. After stirring overnight, the reaction was acidified with acetic acid (1 mL), then hydrazine monohydrate (0.25 mL) was added in one portion. The reaction was heated at 85° C. for 6 hr, cooled and the solid was collected by filtration. The solid was washed with water and the 6-(thiazol-2-yl)pyridazin-3(2H)-one used in the next step (400 mg).

Step 2.

A flask was charged with triphenylphosphine (293 mg, 1.1 mmol), di-tert-butyl azodicarboxylate (194 mg, 0.85 mmol), and 6-(thiazol-2-yl)pyridazin-3(2H)-one (100 mg, 0.56 mmol). The solids were dissolved in dichloromethane, and then 2-methylaminoethanol (0.054 mL, 0.67 mmol) was added at once. After 4 hours, the reaction was concentrated under reduced pressure and the residue was purified by ISCO silica flash chromatography using a dichloromethane: methanol solvent system. The hydrochloride salt of 2-(2-(methylamino)ethyl)-6-(thiazol-2-yl)pyridazin-3(2H)-one was generated using 1 eq of 2M HCl in diethyl ether.

$^1$H NMR 400 Hz (DMSO): δ8.98 (s, 2H), 8.09 (d, 1H, J=9.6 Hz), 7.98 (d, 1H, J=3.2 Hz), 7.90 (d, 1H, J=3.2 Hz), 4.41 (t, 2H, J=6 Hz), 3.32 (m, 2H), 2.57 (s, 3H).

Synthesis of Compound 210: 2-(2-(Dimethylamino)ethyl)-6-(pyridin-3-yl)pyridazin-3(2H)-one

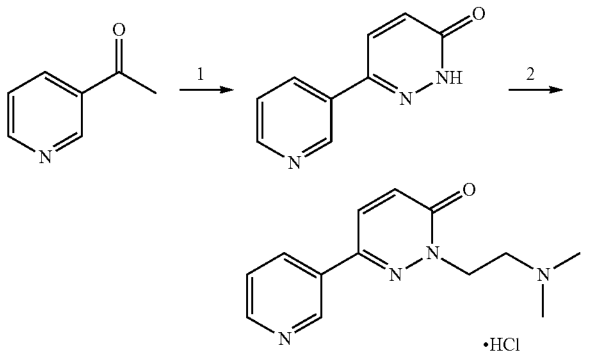

Step 1.

A flask was charged with potassium carbonate (1.2 g). The solid was dissolved in water, then 3-acetylpyridine (0.5 g, 4.1 mmol) was added at once. The solution was stirred for 30 minutes, and then glyoxylic acid (380 mg, 4.1 mmol) was added at once. After stirring overnight, the reaction was acidified with acetic acid (1 mL), then hydrazine monohydrate (0.25 mL) was added in one portion. The reaction was heated at 85° C. for 6 hr, cooled and the solid was collected by filtration. The solid was washed with water and the 6-(pyridin-3-yl)pyridazin-3(2H)-one used in the next step.

Step 2.

A flask was charged with triphenylphosphine (760 mg, 3 mmol), di-tert-butyl azodicarboxylate (501 mg, 2.2 mmol), and 6-(pyridin-3-yl)pyridazin-3(2H)-one (250 mg, 1.45 mmol). The solids were dissolved in dichloromethane, and then dimethylethanolamine (0.174 mL, 1.74 mmol) was added at once. After 3 hours, the reaction was concentrated under reduced pressure and the residue was purified by ISCO silica flash chromatography using a dichloromethane: methanol solvent system. The hydrochloride salt of 2-(2-(dimethylamino)ethyl)-6-(pyridin-3-yl)pyridazin-3(2H)-one was generated using 1 eq of 2M HCl in diethyl ether.

$^1$H NMR 400 Hz (DMSO): δ10.32 (s, 1H), 9.24 (d, 1H, J=2 Hz), 8.77 (dd, 1H, J=1.2 and 5.2 Hz), 8.57 (d, 1H, J=8.4 Hz), 8.17 (d, 1H, J=9.6 Hz), 7.77 (dd, 1H, J1=5.2 Hz, J2=8 Hz), 7.17 (d, 1H, 10 Hz), 4.52 (t, 2H, J=6 Hz), 3.57 (q, 2H, J=5.6 Hz), 2.83 (d, 6H, J=4.8 Hz).

Synthesis of Compound 211: 2-(2-(Dimethylamino)ethyl)-6-(pyridin-4-yl)pyridazin-3(2H)-one hydrochloride 2-(2-(dimethylamino)ethyl)-6-(pyridin-4-yl)pyridazin-3(2H)-one hydrochloride was prepared using the same procedures as above but using 4-acetylpyridine.

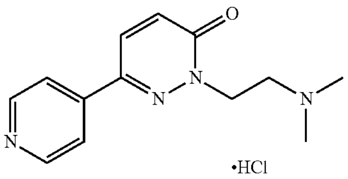 [SMILES: CN(C)CCn1nc(-c2ccncc2)ccc1=O ; Cl]

$^1$H NMR 400 Hz (DMSO): δ10.74 (s, 1H), 8.94 (d, 2H, J=6.4 Hz), 8.37 (d, 2H, J=6.4 Hz), 8.28 (d, 1H, J=9.6 Hz), 7.20 (d, 1H, J=10 Hz), 4.57 (t, 2H, J=6 Hz), 3.56 (q, 2H, J=5.2 Hz), 2.81 (d, 6H, J=3.6 Hz).

Synthesis of Compound 212: 1-(2-(Dimethylamino) ethyl)-5-(pyridin-2-yl)pyrimidin-2(1H)-one

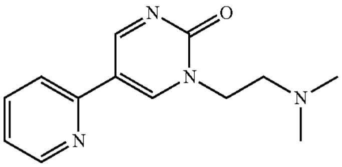 [SMILES: CN(C)CCn1cc(-c2ccccn2)cnc1=O]

Compound 212 was prepared from commercially available 5-(pyridin-2-yl) pyrimidin-2-ol and N,N-dimethylethanolamine using the same procedure as for Compound 100.

$^1$H NMR 400 Hz (CDCl3): δ 9.15 (d, 1H, J=3.1 Hz), 8.61 (s, 1H), 8.48 (s, 1H), 7.77-7.73 (m, 1H), 7.56-7.54 (m, 1H), 7.24-7.21 (m, 1H), 4.07 (t, 2H, J=5.84 Hz), 2.72 (t, 2H, J=5.88 Hz), 2.27 (s, 6H).

Synthesis of Compound 213: 1'-(2-(Dimethylamino)ethyl)-[2,3'-bipyridin]-6'(1'H)-one hydrochloride

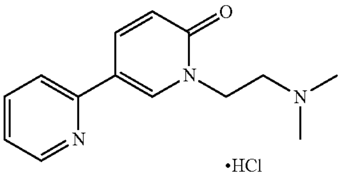 [SMILES: CN(C)CCn1cc(-c2ccccn2)ccc1=O ; Cl]

Compound 213 was prepared from commercially available 5-(pyridin-2-yl)pyridin-2(1H)-one and N,N-dimethylethanolamine using the same procedure as for Compound 100.

$^1$H NMR 400 Hz (DMSO): δ 8.72-8.54 (m, 1H), 8.20 (d, 1H, J=9.6 Hz), 8.13-7.80 (m, 2H), 7.60-7.28 (m, 1H), 6.57 (d, 1H, J=9.6 Hz), 4.39 (s, 2H), 3.48 (s, 2H), 2.83 (s, 6H). $[M+1]^+$=244

Synthesis of Compound 214: 1-(2-(Dimethylamino) ethyl)-5-(pyridin-2-yl)pyrazin-2(1H)-one hydrochloride

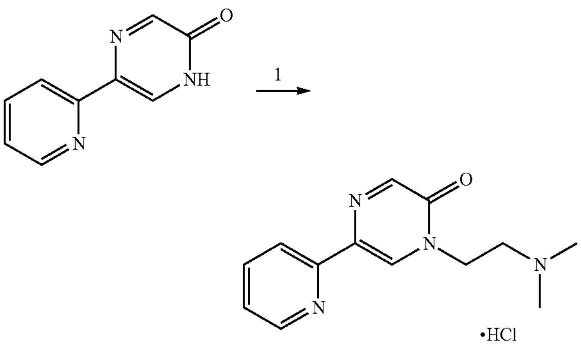

To a solution of commercially available 5-(pyridin-2-yl) pyrazin-2-ol (50 mg, 0.29 mmol) in DMF was added sodium hydride (0.58 mmol) and 2-bromo-N,N-dimethylethanamine (0.4 mmol). The mixture was heated at 90° C. for 48 hrs, cooled to RT and partitioned between ethyl acetate and sodium bicarbonate solution. The mixture was further extracted with ethyl acetate and the combined extracts washed with brine. The extracts were dried, evaporated and purified by ISCO silica flash chromatography using a dichloromethane:methanol solvent system. The hydrochloride salt of 2-(2-(dimethylamino)ethyl)-6-(pyridin-3-yl)pyridazin-3(2H)-one was generated using 1 eq of 2M HCl in diethyl ether.

$^1$H NMR 400 Hz (MeOD): δ7.05 (d, 1H, J=4.8 Hz), 8.47 (s, 1H), (m, 1H), 8.17 (s, 1H) 8.12 (d, 1H, J=8 Hz), 7.87 (td, 1H, J=7.8 and 6 Hz), 7.34-7.30 (m, 1H), 4.34 (t, 2H, J=6 Hz), 3.20 (t, 1H, J=6 Hz), 2.68 (s, 6H). [M+1]*=245

Evaluation of the Biological Activity of Example Compounds

Compounds were evaluated in PA-EAAT2 cells, a primary astrocyte stably expressing human EAAT2 mRNAs (Kong et al., *J Clin Invest.* 2014:1255-67). Cells were treated with compound at 0.0375, 0.075, 0.15, 0.3, 0.6, 1.25, 2.5, 5, 10 μM for 24 hr and then harvested for measuring EAAT2 protein levels by Western blot analysis. The table below shows the fold increases in EAAT2 protein levels relative to DMSO at indicated concentration that reaches maximum activity.

| Compound | Structure | Fold increase for EAAT2 at indicated concentration (maximum activity) |
|---|---|---|
| 100 | 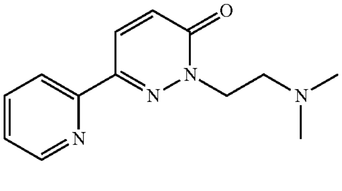 [SMILES: CN(C)CCn1nc(-c2ccccn2)ccc1=O] | 2.3 ± 0.3 (0.6 μM) |

-continued
| Compound | Structure | Fold increase for EAAT2 at indicated concentration (maximum activity) |
| --- | --- | --- |
| 101 | 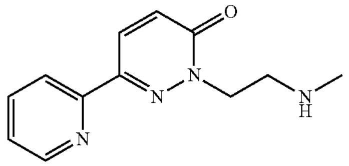 | 2.6 ± 0.2 (0.3 μM) |
| 126 | 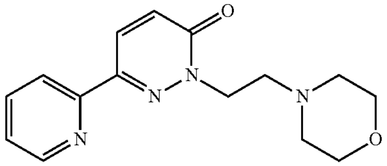 [SMILES: O=c1ccc(-c2ccccn2)nn1CCN1CCOCC1] | 2.2 ± 0.5 (0.3 μM) |
| 198 | 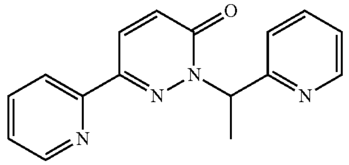 [SMILES: CC(c1ccccn1)n1nc(-c2ccccn2)ccc1=O] | 2.0 ± 0.3 (0.15 μM) |
| 166 | 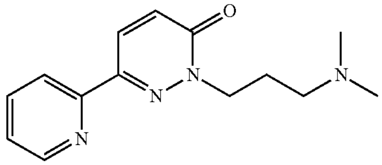 [SMILES: CN(C)CCCn1nc(-c2ccccn2)ccc1=O] | 2.0 ± 0.2 (0.3 μM) |
| 146 | 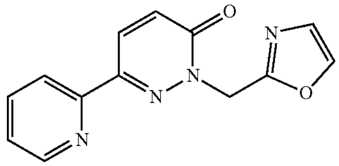 [SMILES: O=c1ccc(-c2ccccn2)nn1Cc1ncco1] | 2.6 ± 0.2 (2.5 μM) |
| 172 | 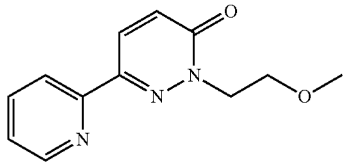 [SMILES: COCCn1nc(-c2ccccn2)ccc1=O] | 2.9 ± 0.1 (0.3 μM) |
| 195 | 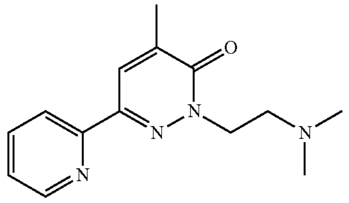 [SMILES: Cc1cc(-c2ccccn2)nn(CCN(C)C)c1=O] | 2.5 ± 0.2 (0.3 μM) |
| 196 | 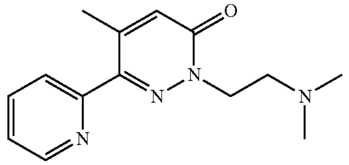 [SMILES: Cc1cc(=O)n(CCN(C)C)nc1-c1ccccn1] | 4.2 ± 0.2 (0.6 μM) |

-continued
| Compound | Structure | Fold increase for EAAT2 at indicated concentration (maximum activity) |
| --- | --- | --- |
| 214 | 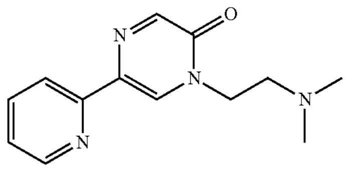 [SMILES: CN(C)CCn1cc(-c2ccccn2)ncc1=O] | 1.5 ± 0.1 (2.5 μM) |
| 213 | 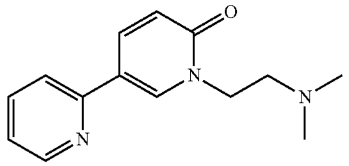 [SMILES: CN(C)CCn1cc(-c2ccccn2)ccc1=O] | 2.3 ± 0.1 (0.6 μM) |
| 203 | 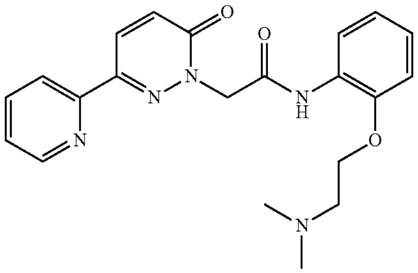 [SMILES: CN(C)CCOc1ccccc1NC(=O)Cn1nc(-c2ccccn2)ccc1=O] | 2.0 ± 0.2 (0.6 μM) |
| 110 | 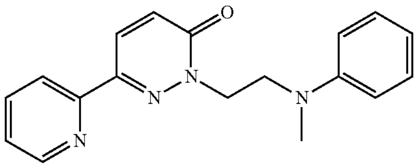 [SMILES: CN(CCn1nc(-c2ccccn2)ccc1=O)c1ccccc1] | 2.3 ± 0.3 (0.6 μM) |
| 123 | 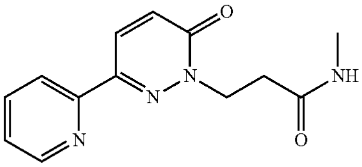 [SMILES: CNC(=O)CCn1nc(-c2ccccn2)ccc1=O] | 2.5 ± 0.2 (0.3 μM) |
| 102 | 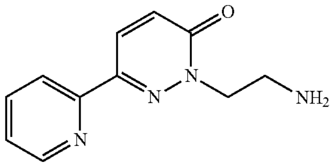 [SMILES: NCCn1nc(-c2ccccn2)ccc1=O] | 2.8 ± 0.3 (1.25 μM) |
| 133 | 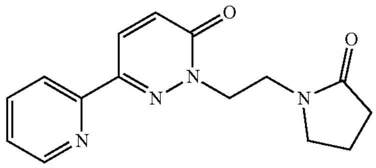 [SMILES: O=C1CCCN1CCn1nc(-c2ccccn2)ccc1=O] | 1.9 ± 0.3 (2.5 μM) |
| 201 | 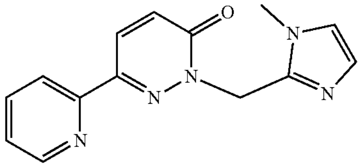 [SMILES: Cn1ccnc1Cn1nc(-c2ccccn2)ccc1=O] | 2.5 ± 0.4 (0.6 μM) |

-continued

| Compound | Structure | Fold increase for EAAT2 at indicated concentration (maximum activity) |
|---|---|---|
| 206 | 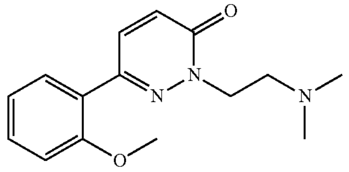 [SMILES: COc1ccccc1-c1ccc(=O)n(CCN(C)C)n1] | 2.4 ± 0.1 (0.15 μM) |
| 207 | 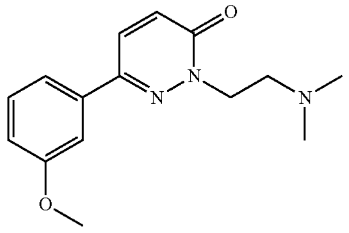 [SMILES: COc1cccc(-c2ccc(=O)n(CCN(C)C)n2)c1] | 3.5 ± 0.3 (0.15 μM) |
| 208 | 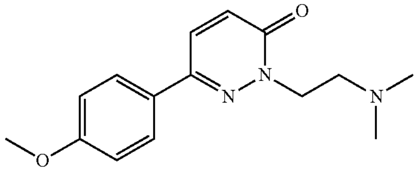 | 1.7 ± 0.2 (0.3 μM) |

For EAAT2 induction in vivo studies, 2-3-month-old wild-type C57BL/6 mice were treated orally with compound 100 at 10 mg/kg/day (voluntary ingestion of compound in honey) for indicated days. Mice then were euthanized and brains were harvested for examining EAAT2 protein levels by Western blot analysis. Data obtained for Compound 100 is included in Table 1 below.

TABLE 1

Summary of the EAAT2 induction activity of Compound 100. EAAT2 induction in vitro and in vivo

| | |
|---|---|
| In vitro - primary astrocytes ($EC_{50}$) | 250 nM |
| In vivo in wild-type mice - single dose by p.o. | 1.56-fold @ 10 mpk |
| In vivo in wild-type mice - 7-day dosing by p.o. | 1.63-fold @ 10 mpk |
| In vivo in wild-type mice - 28-day dosing by p.o. | 2.37-fold @ 10 mpk |

Figure 2A:
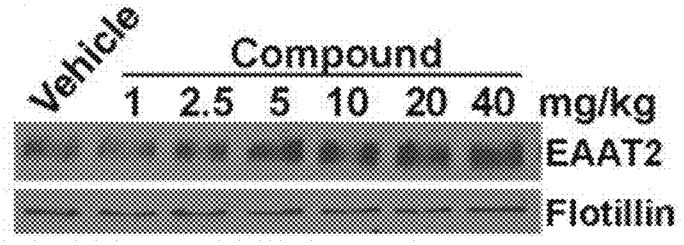
FIGS. 2A-2C show that compound 100 increases EAAT2 expression and enhances synaptic plasticity in wild-type mice. Mice were treated with compound at 40 mg/kg (or as depicted) and forebrains were harvested for the gliosome preparation 24 hr (or as described) post-treatment.
Figure 2B:
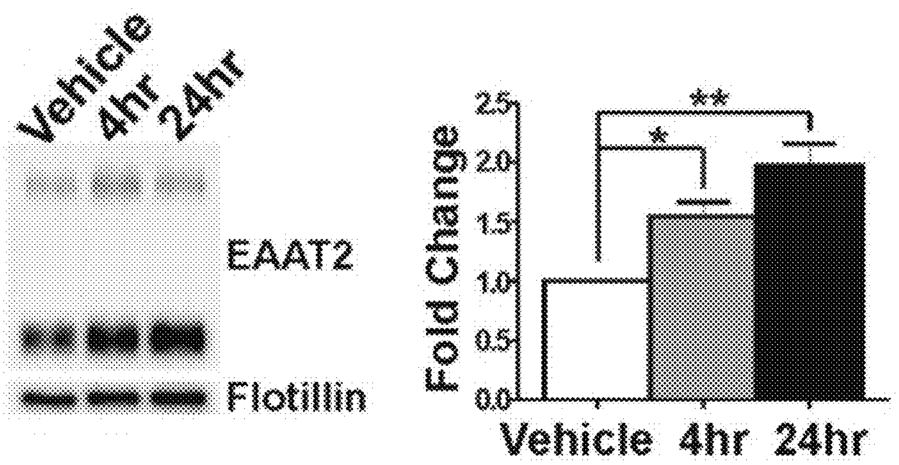
Figure 2C:
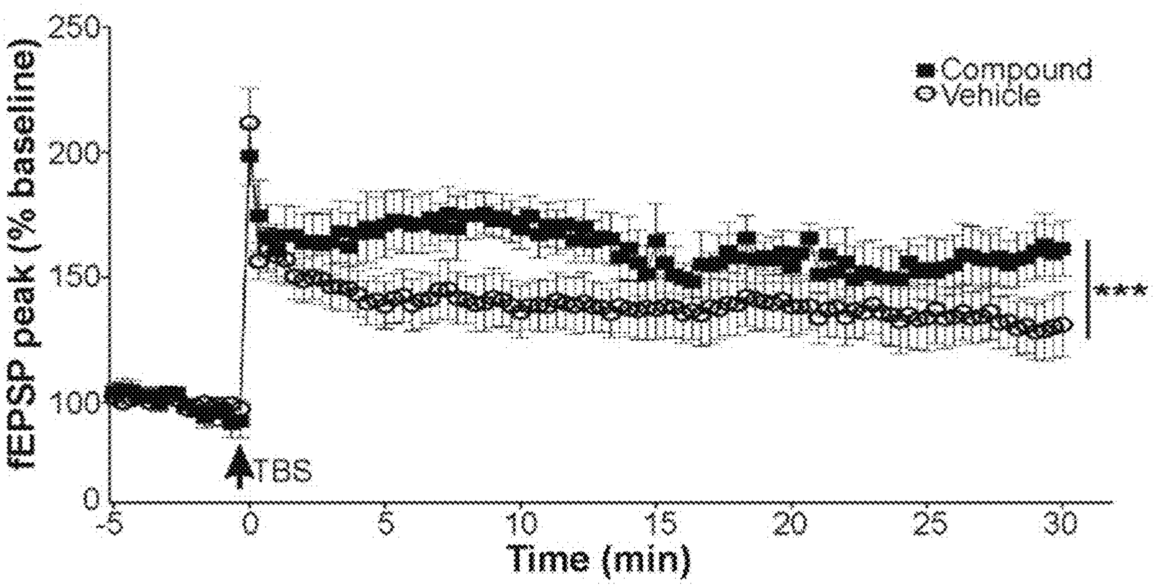

Compound 100 Increases EAAT2 Protein Levels and Enhances Synaptic Plasticity in the Brains of Wild-Type Mice Wild-type FVB/NJ mice (3-4 months old) were treated orally with compound 100 at 1, 2.5, 5, 10, 20, 40 mg/kg. At 24 hours post-treatment, mice were euthanized and for brains were harvested. Gliosomes (astrocytic processes) were then isolated for measuring EAAT2 protein levels by Western blot analysis. As shown in FIG. 2A, compound treatment induced EAAT2 expression in a dose-dependent manner. This induction could be seen as early as 4 hours post-treatment (FIG. 2B). To determine the functional consequences of the increased EAAT2 to the synaptic plasticity, wild-type mice were treated with vehicle or compound 100 at 10 mg/kg for 7 days. Acute hippocampal slices were then collected and assessed for changes in long-term potentiation (LTP). As shown in FIG. 2C, field potential recordings from CA1 of compound treated mice (10 slices, 4 animals) showed significantly increased responses to stimulation of CA3 afferents up to 30 min after LTP induction compared to vehicle treated animals (11 slices, 4 animals). These results indicate that compound treatment increases EAAT2 protein levels and subsequently enhances synaptic plasticity in the hippocampus.

Compound 100 Increases EAAT2 Protein Levels in the Brains of Dogs

Figure 3:
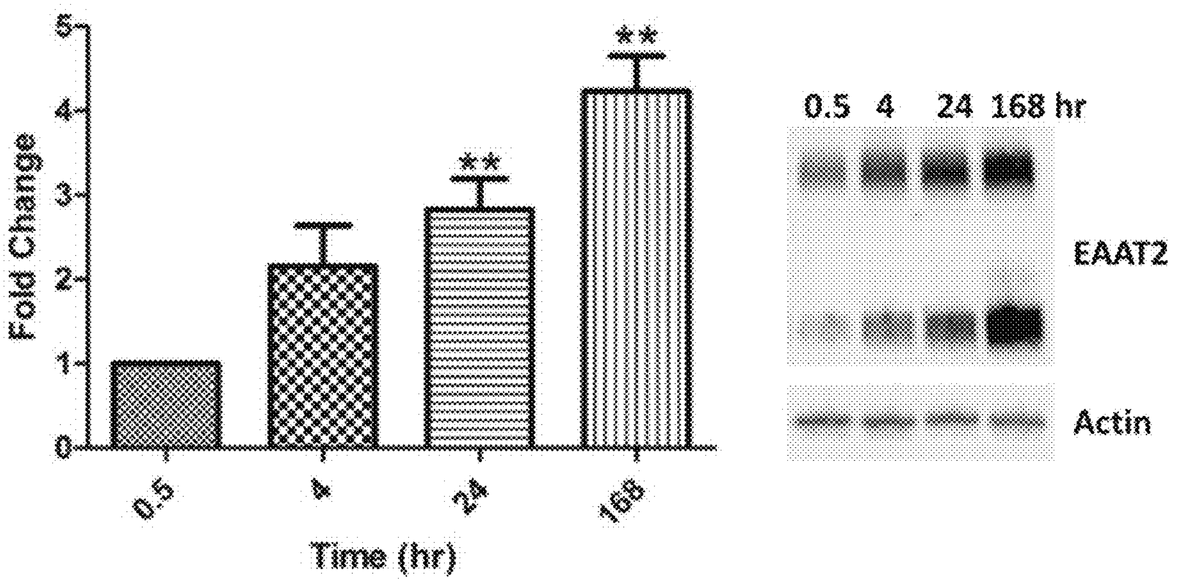
FIG. 3 shows the time-dependent increase in EAAT2 protein expression in the brains of beagle dogs in response to treatment with Compound 100 (n=3/group).

Male Beagle dogs were treated orally with compound 100 at 20 mg/kg. At 0.5, 4, and 24 hours post-treatment, mice were euthanized and brains were harvested for measuring EAAT2 protein levels by Western blot analysis. In addition, we also measured EAAT2 protein levels after seven daily treatment. As shown in FIGS. 3, EAAT2 levels were increased in a time-dependent manner.

Compound 100 Prevents Neurodegeneration, Improves Cognitive Function, Enhances Synaptic Plasticity, Reduces Tau Hyperphosphorylation, and Delays Disease Progression in a Tauopthy Model of Alzheimer's Disease rTg(tauP301L)4510 mice develop progressive, age-related Alzheimer's disease (AD)-like pathologies. These mice exhibit hippocampal hyperexcitability at age of ~3 months. Hippocampal dependent spatial, short-term, and long-term memory deficits can be detected as early as 1, 2, and 4 months, respectively. By ~4 months in the hippocampus and ~5-6 months in the cortex, mild to moderate tau pathology is seen. By ~5-6 months of age, rTg4510 mice exhibit ~60% loss of hippocampal pyramidal neurons.

To investigate the effects of compound 100 in rTg4510 mice at early symptomatic stage, littermate-matched mice with equal gender distribution were divided into four groups: control (wild-type)/vehicle; control/compound; rTg4510/vehicle; and rTg4510/compound (n=30-35 per group). Mice received compound at 10 mg/kg/day by voluntary ingestion of compound in honey starting at two months of age. At four months old (moderate disease stage), mice were subjected to open field tests to assess agitation-like behavior and then three cognitive tests, including Y-maze, novel object recognition, and T-maze tests. Examiners were blinded regarding treatment. Upon completion of behavioral assessment, a subset of mice (n=10-12 per group) were euthanized for pathological studies and the rest of mice continued receiving treatment. At eight months old (severe disease stage), mice again were subjected to open field tests and cognitive tests. Following behavioral testing, mice were euthanized for pathological studies or electrophysiological studies.

Figure 4A:
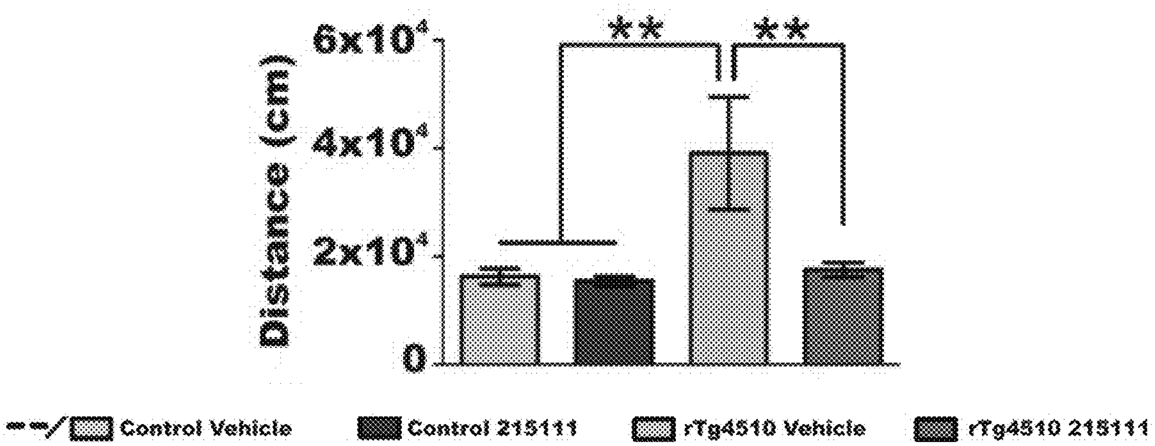
FIGS. 4A-4G illustrate the efficacy of Compound 100 in rTg(tauP301L)4510 mice at moderate disease stage.
Figure 4B:
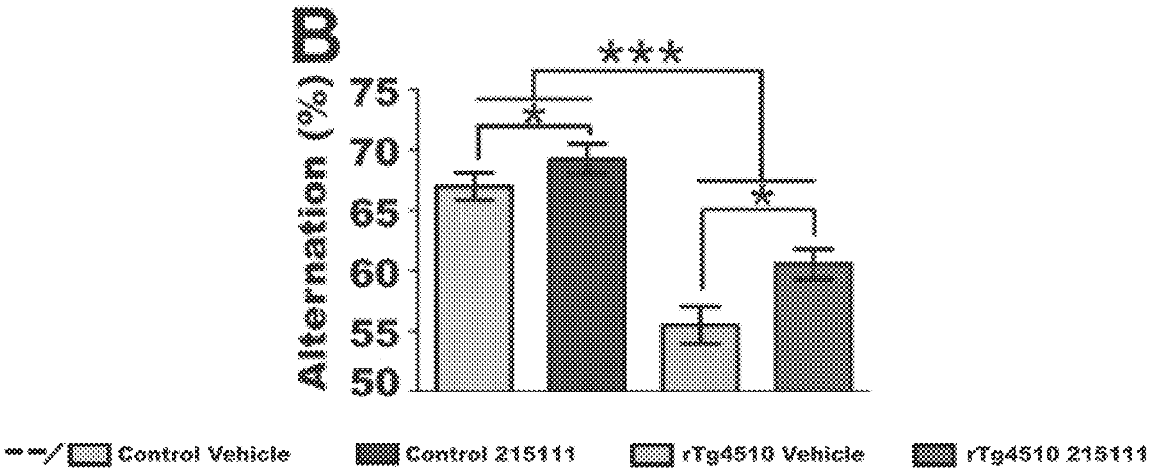
Figure 4C:
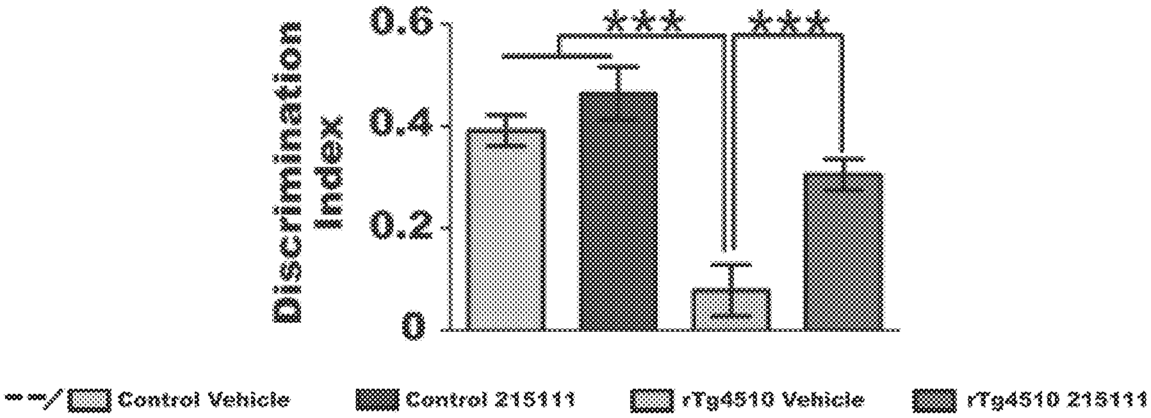
Figure 4D:
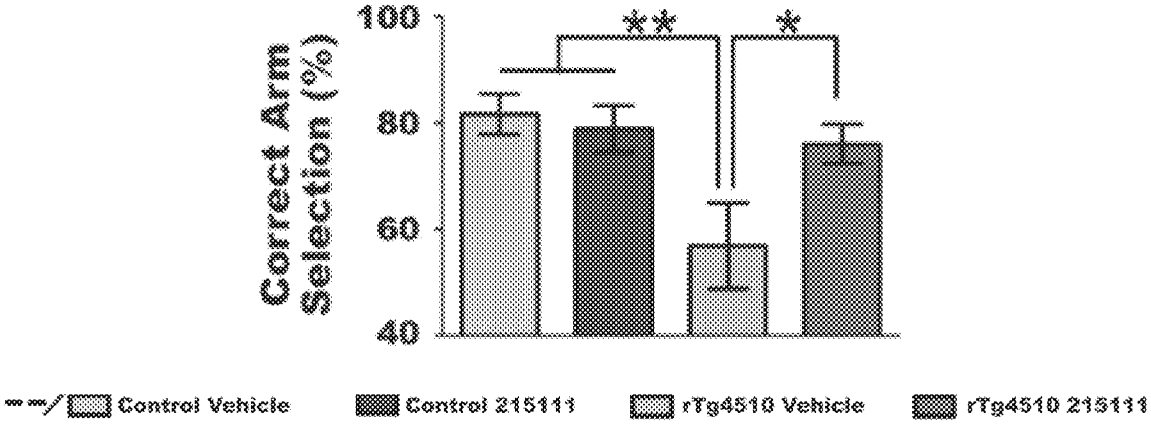
Figure 4E:
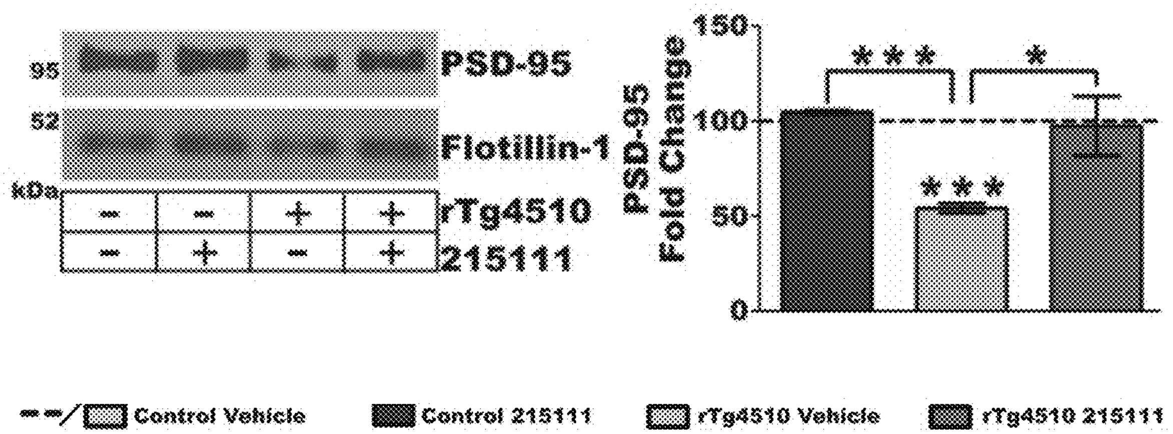
Figure 4F:
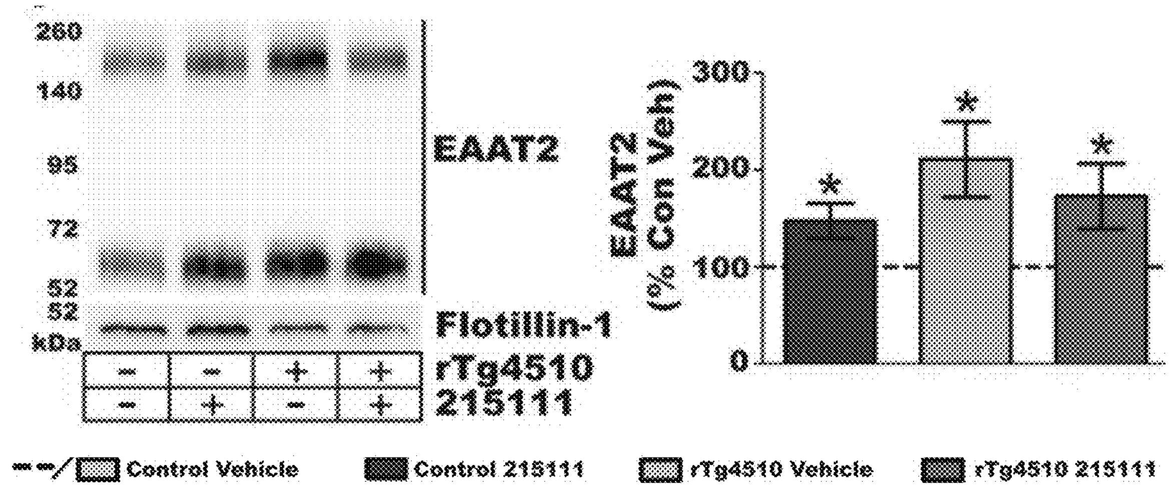
Figure 4G:
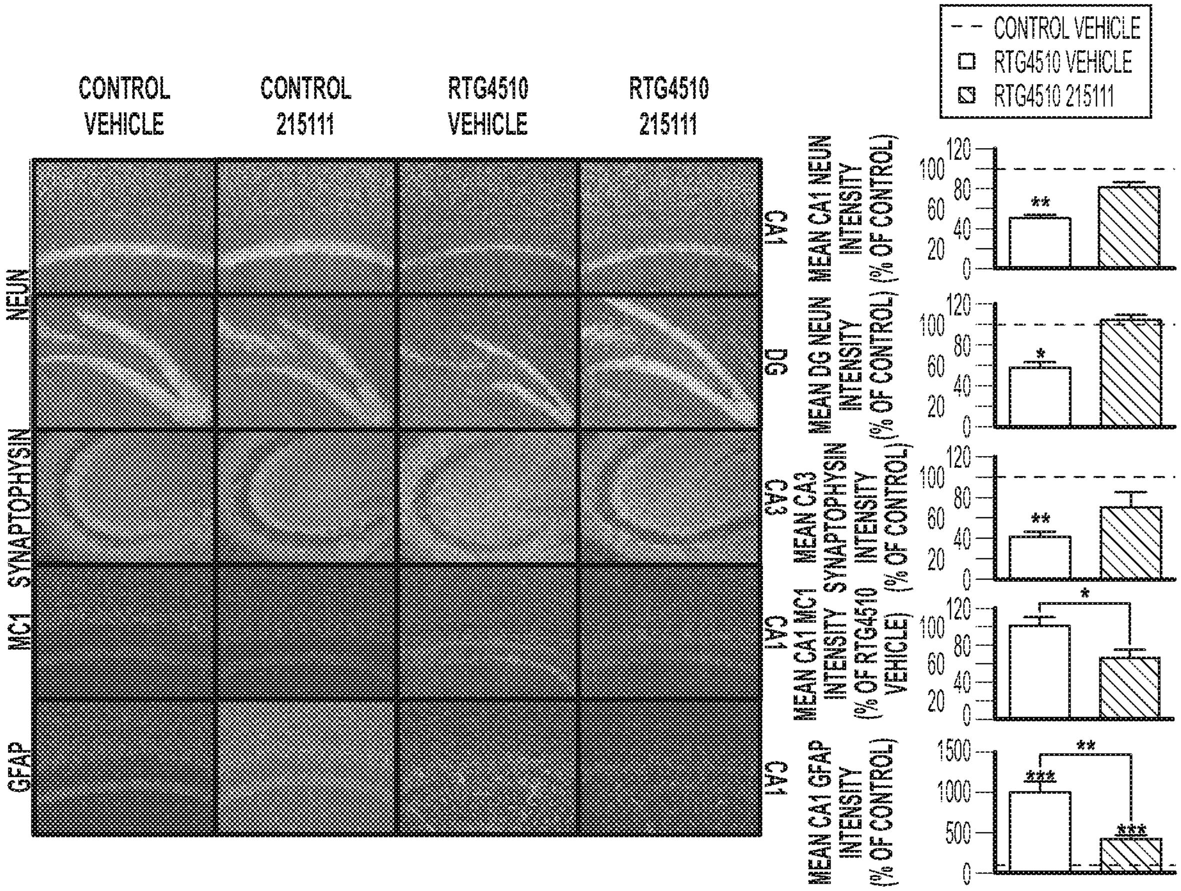

The results of behavioral and pathological assessments at four months of age are presented in FIGS. 4A-4G. No obvious differences were observed between genders. Open field results indicated that compound treatment completely ameliorated agitative-like behavior in rTg4510 mice (FIG. 4A). In all three cognitive tests, vehicle-treated rTg4510 mice showed very significant impairments. Importantly, compound treatment significantly improved short-term memory (Y-maze; FIG. 4B), non-spatial long-term memory (novel object recognition; FIG. 4C), and spatial learning memory (T-maze; FIG. 4D). Upon completion of behavioral assessment, mice were euthanized for pathological studies. To assess synaptic integrity, we isolated postsynaptic density complexes prepared from hippocampus. Postsynaptic density 95 (PSD-95) levels, a postsynaptic density protein, were measured by Western blot analysis. Results showed that vehicle-treated rTg4510 mice exhibited significantly reduced PSD-95 levels in the postsynaptic density complexes, indicating a reduced number of synapses, which was normalized in compound-treated rTg4510 mice (FIG. 4E). We examined EAAT2 levels in the hippocampus by performing crude plasma membrane preparations to assess membrane-bound EAAT2. Unexpectedly, results showed an increase in expression of EAAT2 in vehicle-treated rTg4510 mice, which were partially normalized by the compound treatment (FIG. 4F). Furthermore, immunohistochemical analysis of hippocampal regions revealed that vehicle-treated rTg4510 mice exhibited severe neurodegeneration in the CA1 and the DG region, as assessed by NeuN immunostaining, but the neuronal loss was almost completely prevented in compound-treated rTg4510 mice (FIG. 4G). Moreover, expression of the pre-synaptic marker synaptophysin (a proxy for synaptic integrity) was completely lost in the CA3 region in vehicle-treated rTg4510 mice but was well-preserved in compound-treated rTg4510 mice (FIG. 4G). Neurofibrillary tangles, which were detected in the CA1 region of vehicle-treated rTg4510 mice by MC1 immunostaining, were significantly reduced in compound-treated rTg4510 mice (FIG. 4G). We examined astroglial activation and gliosis by GFAP (glial fibrillary acidic protein) immunostaining and found a remarkable increase in GFAP immunoreactivity in CA1 region of vehicle-treated rTg4510 mice, which was significantly decreased in compound-treated rTg4510 mice (FIG. 4G). Taken together, we found that when treatment began at two months of age, rTg4510 mice demonstrated near-normal cognition and behavior, almost indistinguishable from control mice, at four months old. This indicates the exceptional efficacy of compound 100.

Figure 5A:
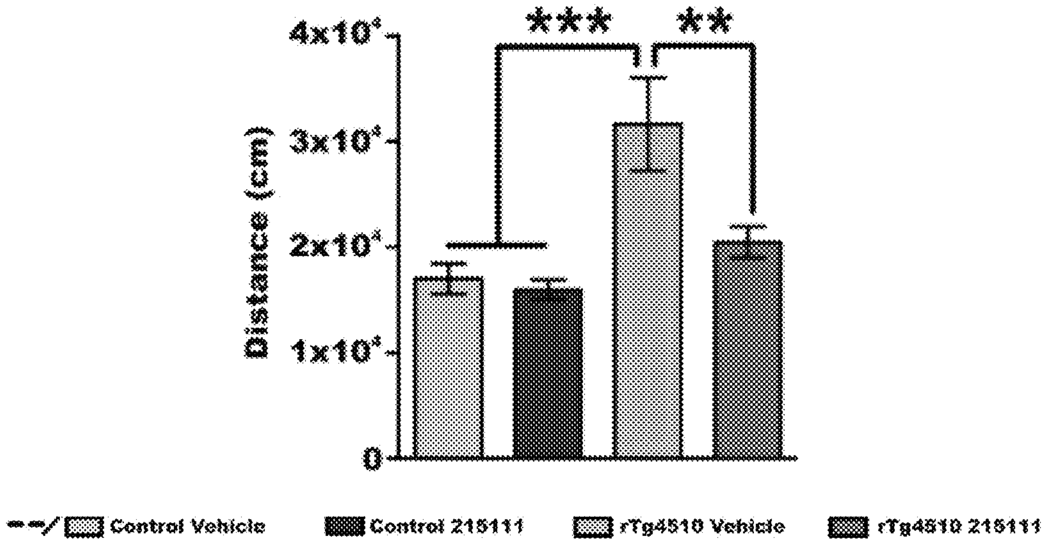
FIGS. 5A-5I illustrate the efficacy of Compound 100 efficacy in rTg(tauP301L)4510 mice at severe disease stage.
Figure 5B:
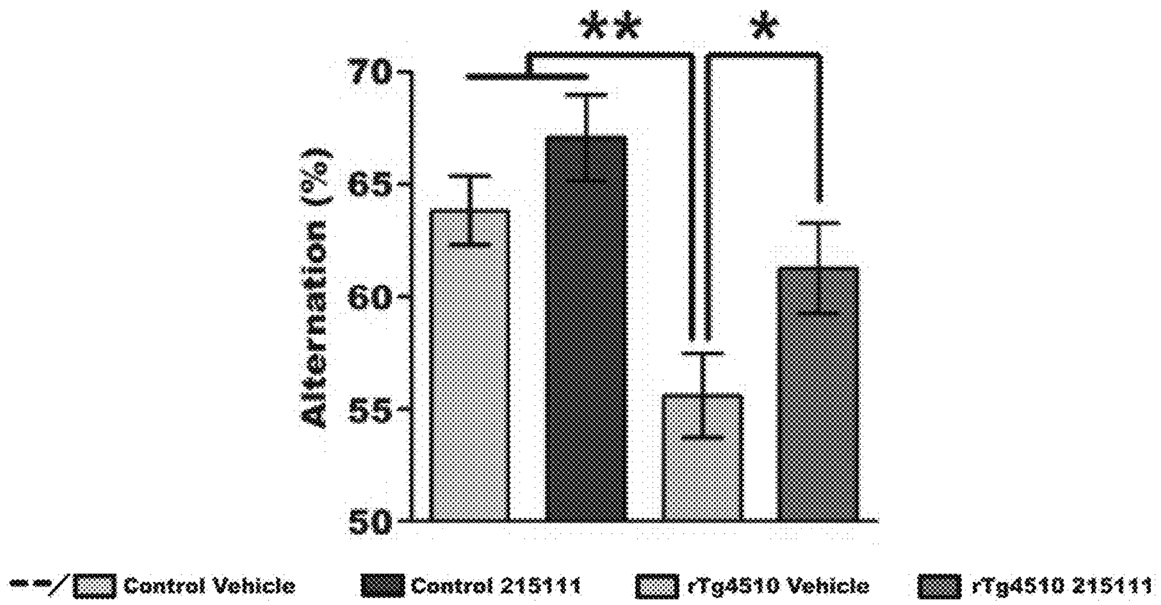
Figure 5C:
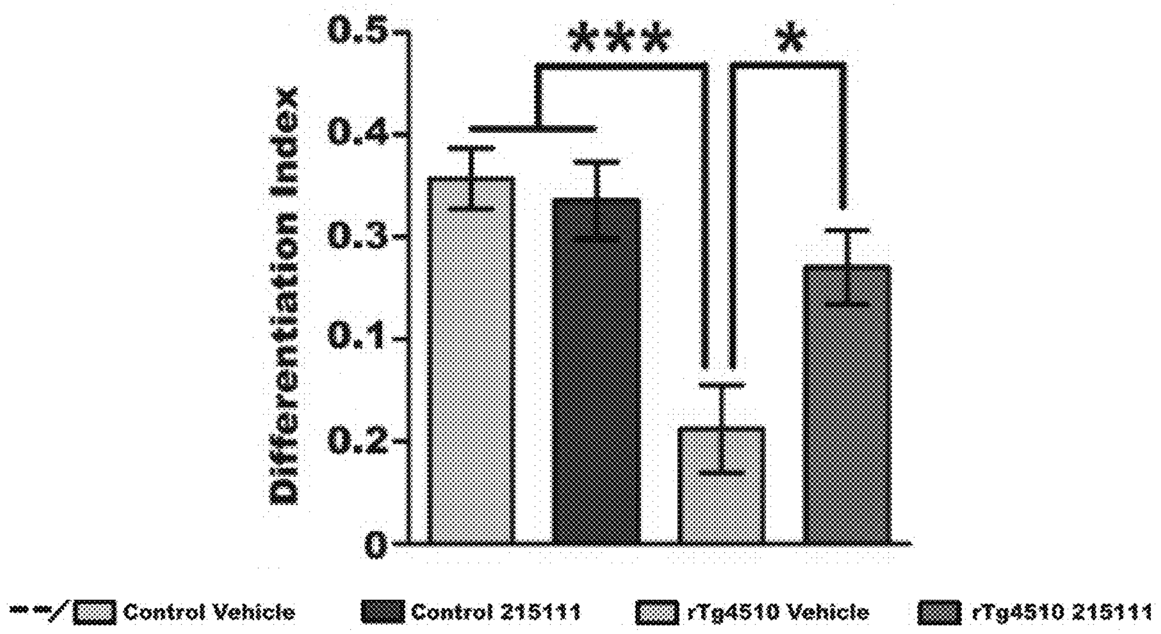
Figure 5D:
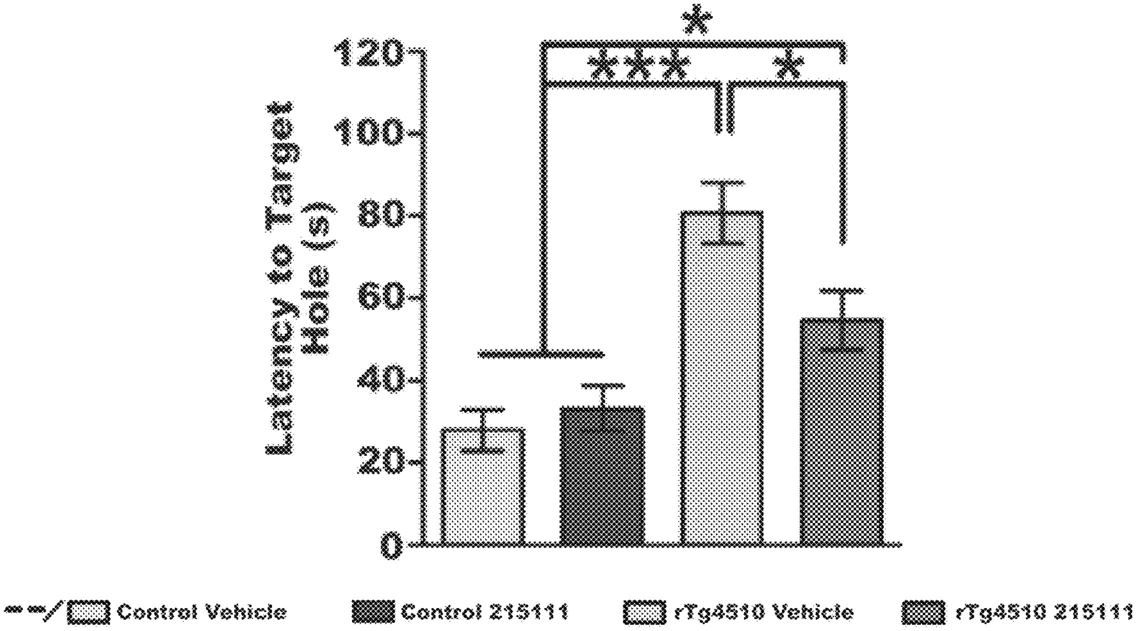
Figure 5E:
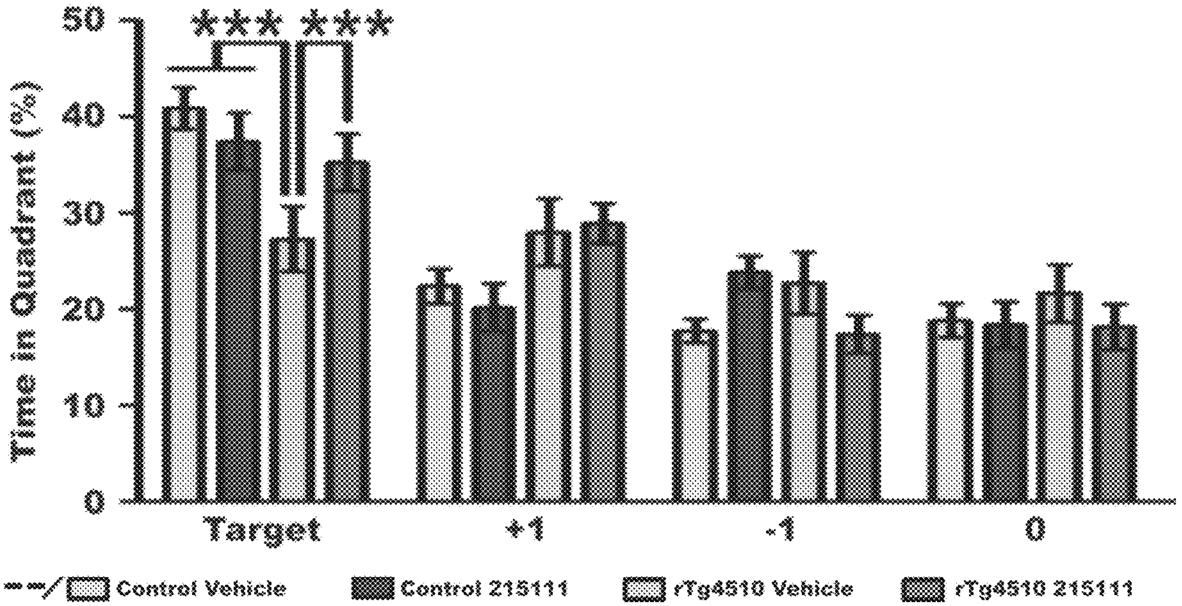
Figure 5F:
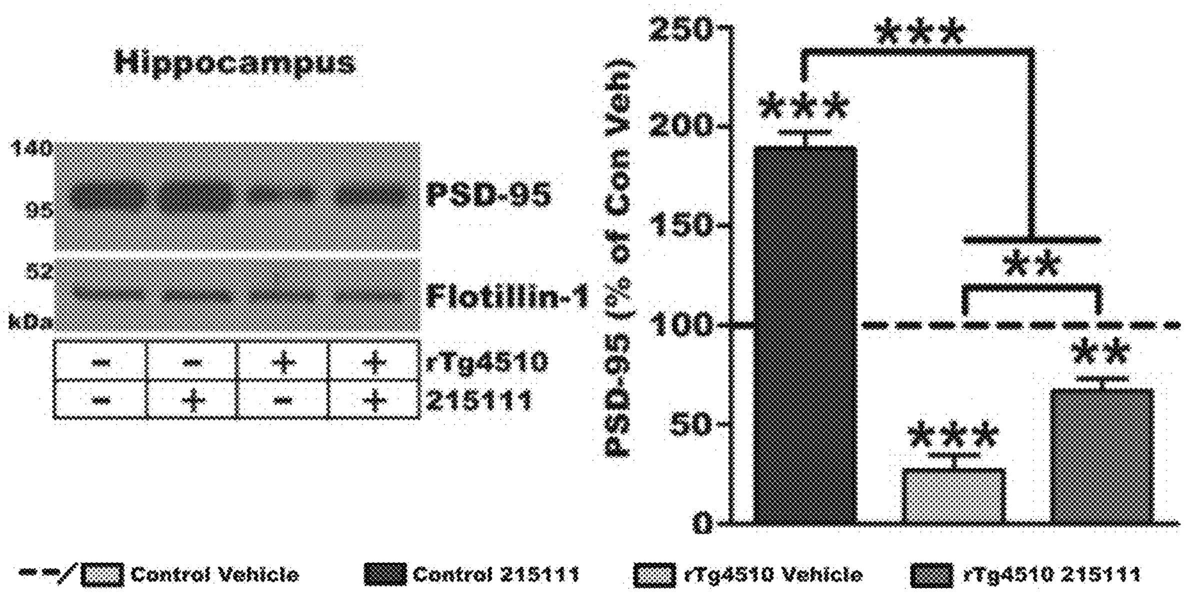
Figure 5G:
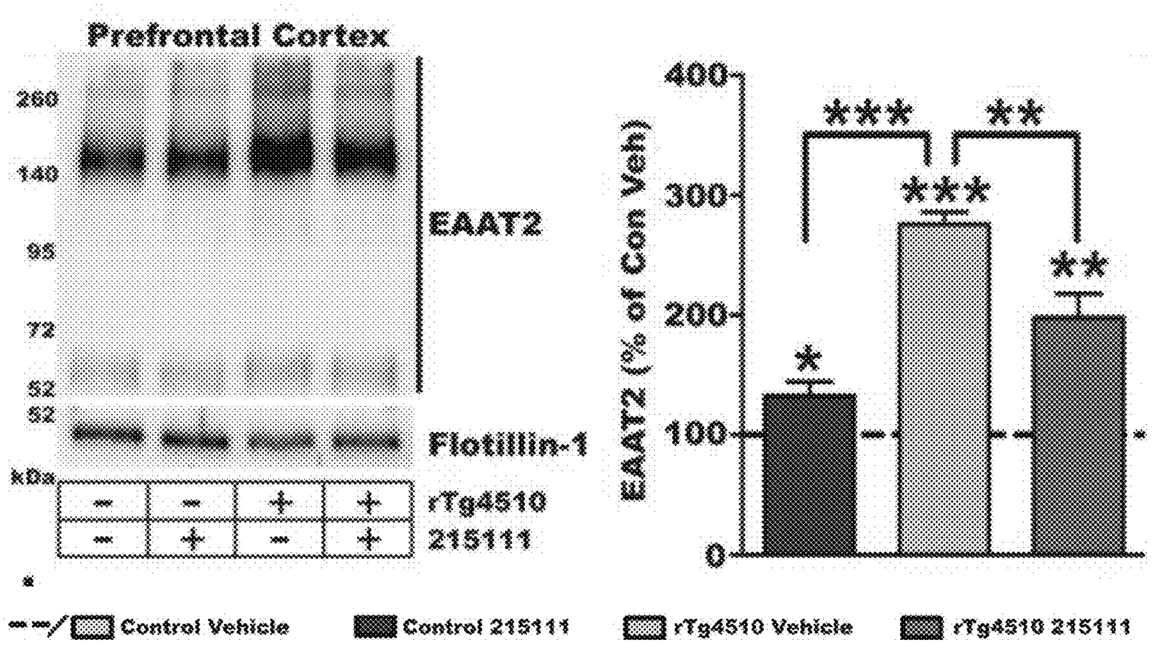
Figure 5H:
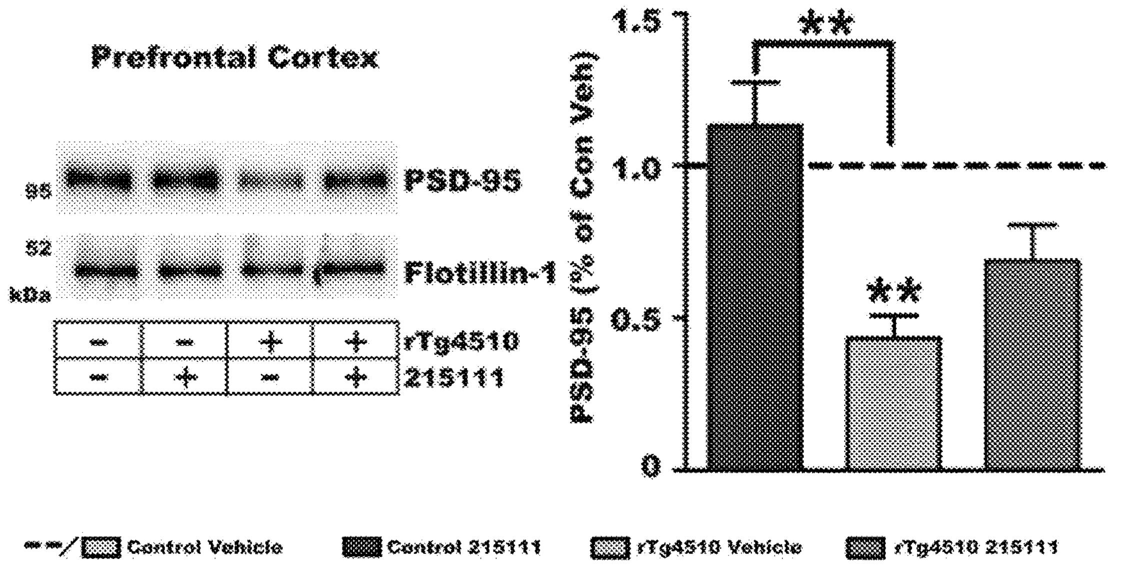
Figure 5I:
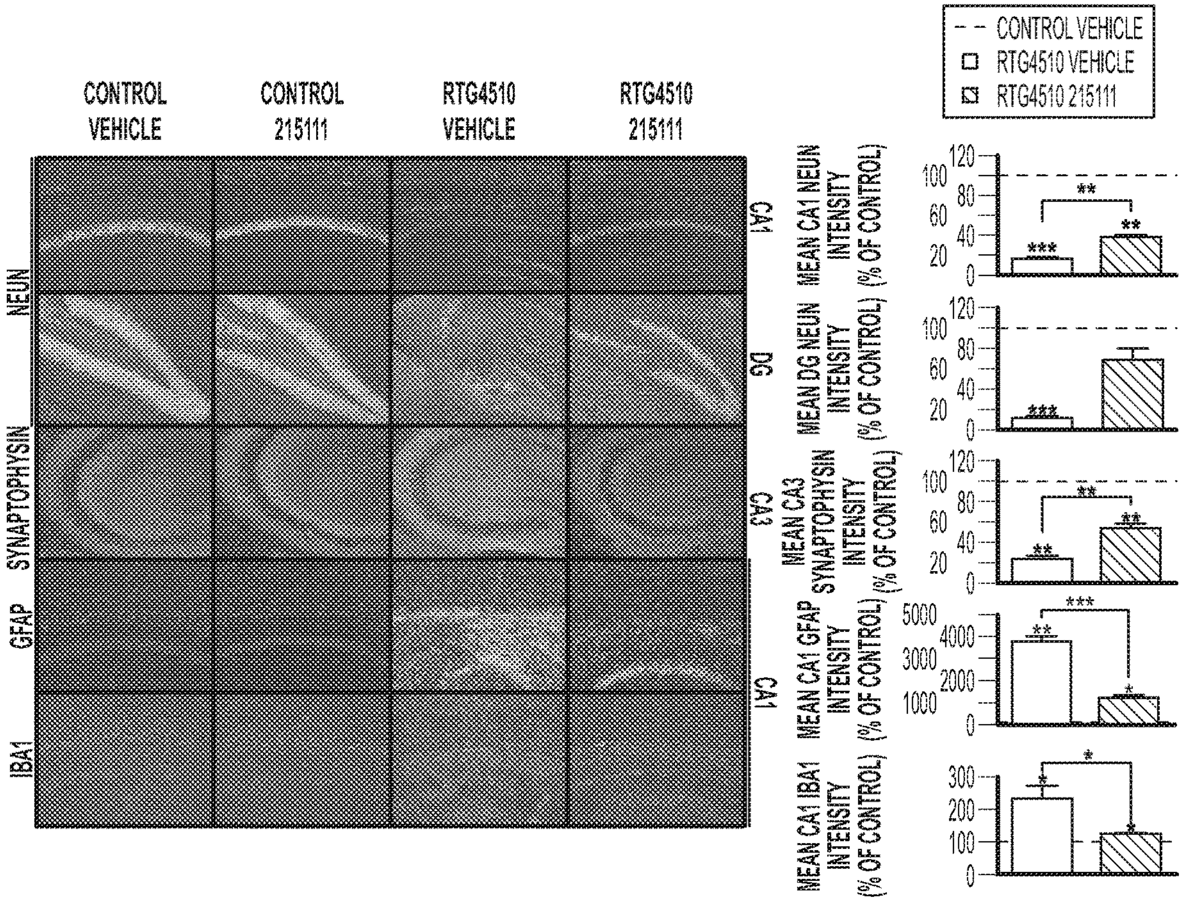

The results of behavioral and pathological assessments at eight months of age are presented in FIGS. 5A-5I. The agitative-like behavior was still normalized by compound treatment, as assessed by open field tests (FIG. 5A). For the cognitive assessment, compound 100 still significantly prevented short-term memory decline (Y-maze; FIG. 5B) and non-spatial long-term memory decline (novel object recognition; FIG. 5C). We utilized Barnes maze test in lieu of T-maze test to assess spatial learning memory. Vehicle-treated rTg4510 mice took significantly longer to find the target hole (FIG. 5D) and spent significantly less time in the target quadrant of the maze (FIG. 5E). On the other hand, compound-treated rTg4510 mice found the target hole significantly faster (FIG. 5D) and spent more time in the target quadrant (FIG. 5E). These behavior studies indicated that compound treatment still provided significant beneficial effects to cognitive functions at this late stage of the disease. Follow-up pathological studies showed that vehicle-treated rTg4510 mice exhibited very significantly reduced PSD-95 levels in the postsynaptic density complexes prepared from hippocampi (FIG. 5F). Compound-treated rTg4510 mice maintained significantly higher PSD-95 expression than vehicle-treated rTg4510 mice. Unlike at four months of age, EAAT2 expression in the hippocampus showed no difference between treated and untreated rTg4510 mice. However, by eight months, the prefrontal cortex exhibited synaptic pathology, similar to what was observed in the hippocampus at four months old. We found a significant increase of EAAT2 expression and a significant loss of PSD-95 protein in the prefrontal cortex of vehicle-treated rTg4510 mice (FIG. 5G, 5H). Compound treatment partially normalized the expression of both PSD-95 and EAAT2. Furthermore, immunohistochemical analysis of hippocampal regions revealed that at this stage of disease progression, both vehicle- and compound-treated rTg4510 mice exhibit significant neurodegeneration in CA1 and DG regions, as assessed by NeuN immunostaining. However, compound treated rTg4510 mice showed significantly reduced levels of neurodegeneration in both regions (FIG. 5I). In addition, expression of synaptophysin was partially preserved in compound-treated rTg4510 mice (FIG. 5I). Both rTg4510 groups exhibit increased GFAP immunoreactivity; however, compound treatment significantly reduced GFAP immunoreactivity in the CA1 (FIG. 5I). Vehicle-treated rTg4510 mice had a significant increase in Ibal immunoreactivity. The increase in Ibal immunoreactivity was significantly lower in compound-treated mice (FIG. 5I). Overall, Compound 100 continues to provide disease-modifying and disease-delaying benefits against all phenotypes tested after long-term treatment.

Figure 6A:
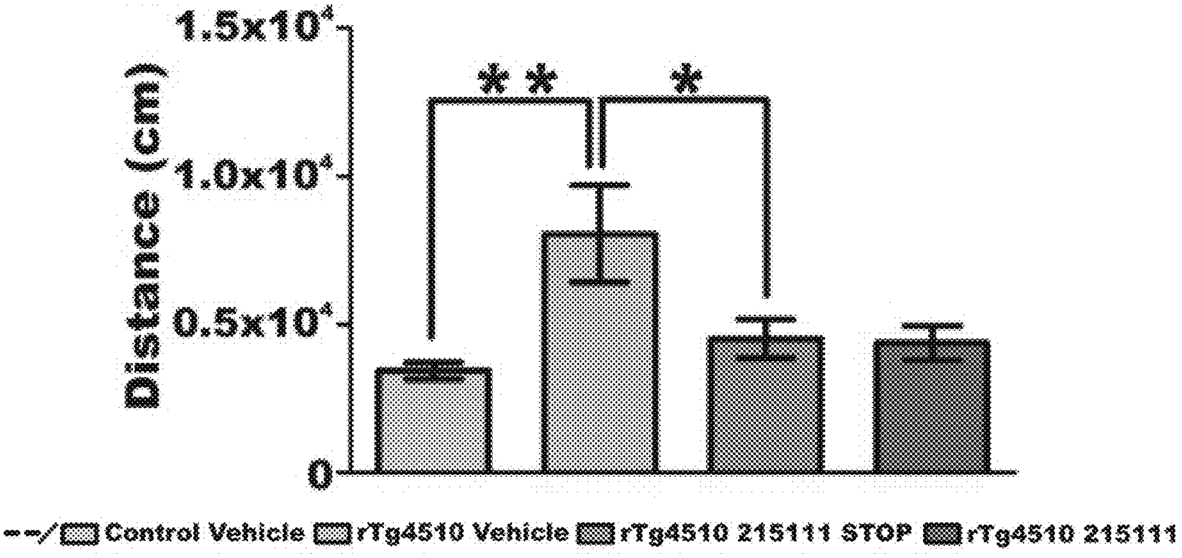
FIGS. 6A-6E illustrate that Compound 100 modifies disease progression in rTg(tauP301L)4510 mice. In a cohort of rTg4510 compound treated mice, treatment was terminated (STOP) and 30 days later behavioral analysis (n=9/9/6/4 respectively), tissue collection, and long-term potentiation (LTP) were performed. Hyperactivity in the open field (FIG. 6A) and cognitive function in the novel object recognition (FIG. 6B) remained normalized in the rTg4510 treatment STOP group relative to the rTg4510 vehicle group.
Figure 6B:
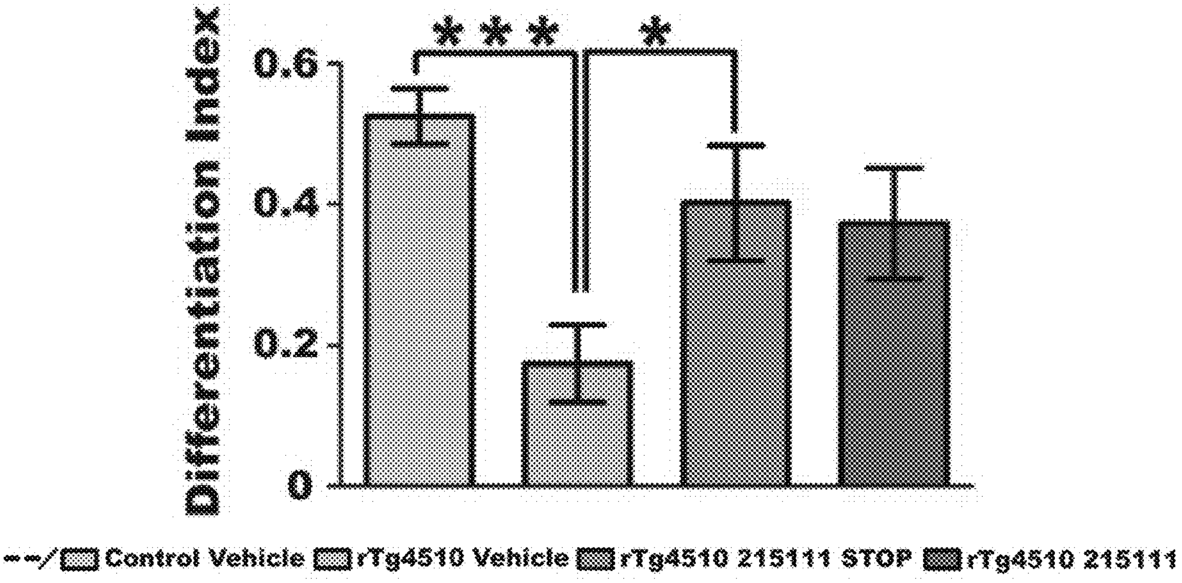
Figure 6C:
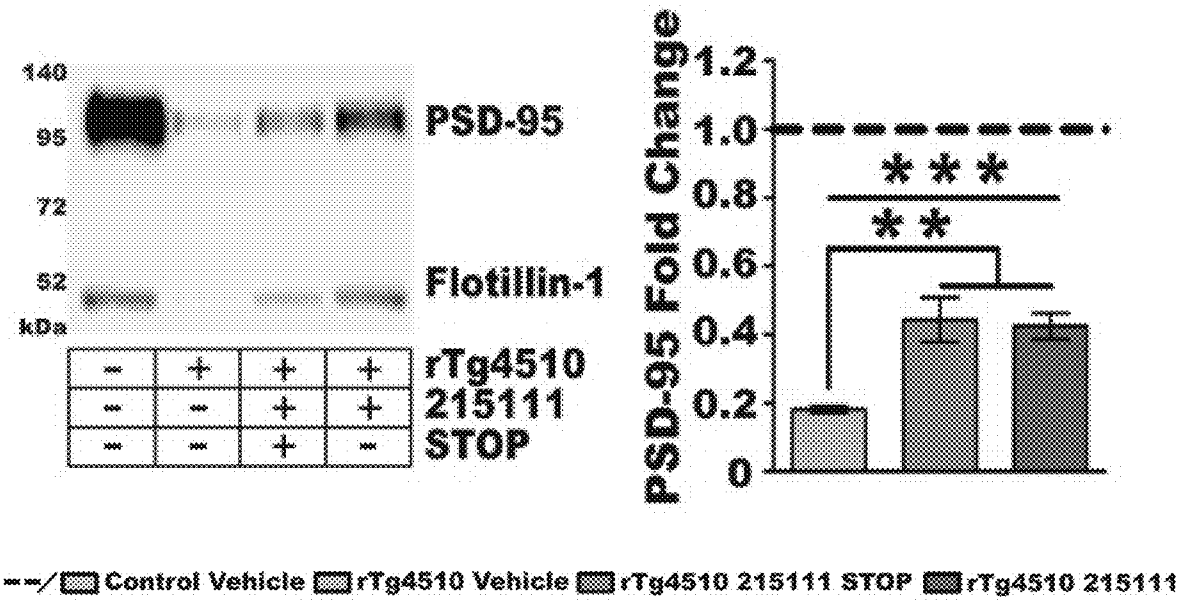

To determine how long the benefits of treatment could persist, a cohort of compound-treated rTg4510 mice was switched to vehicle-treatment (STOP-treatment) at eight months of age. One-month post-treatment cessation, behavior tests, followed by pathological studies, were conducted to compare the STOP-treatment rTg4510 group with the continued-treatment rTg4510 group, the vehicle rTg4510 group, and the control vehicle group. Surprisingly, locomotor activity levels in the open field remained normalized in the STOP-treatment group (FIG. 6A). Novel object recognition results indicated that long-term memory was preserved in the STOP-treatment rTg4510 mice (FIG. 6B). For both behavioral tasks, the STOP-treatment and the continued-treatment groups performed essentially identically. Follow-up pathological studies showed that all rTg4510 groups exhibited significant reductions in PSD-95 levels in the postsynaptic densities of the hippocampus; however, the STOP-treatment group showed a significant increase, approximately two-folds, in PSD-95 levels relative to the vehicle group (FIG. 6C). The expression level of PSD-95 in the STOP-treatment group was indistinguishable from the continued-treatment group. These results indicated that compound 100 directly modifies disease pathology and does not act as a palliative care agent.

Figure 6D:
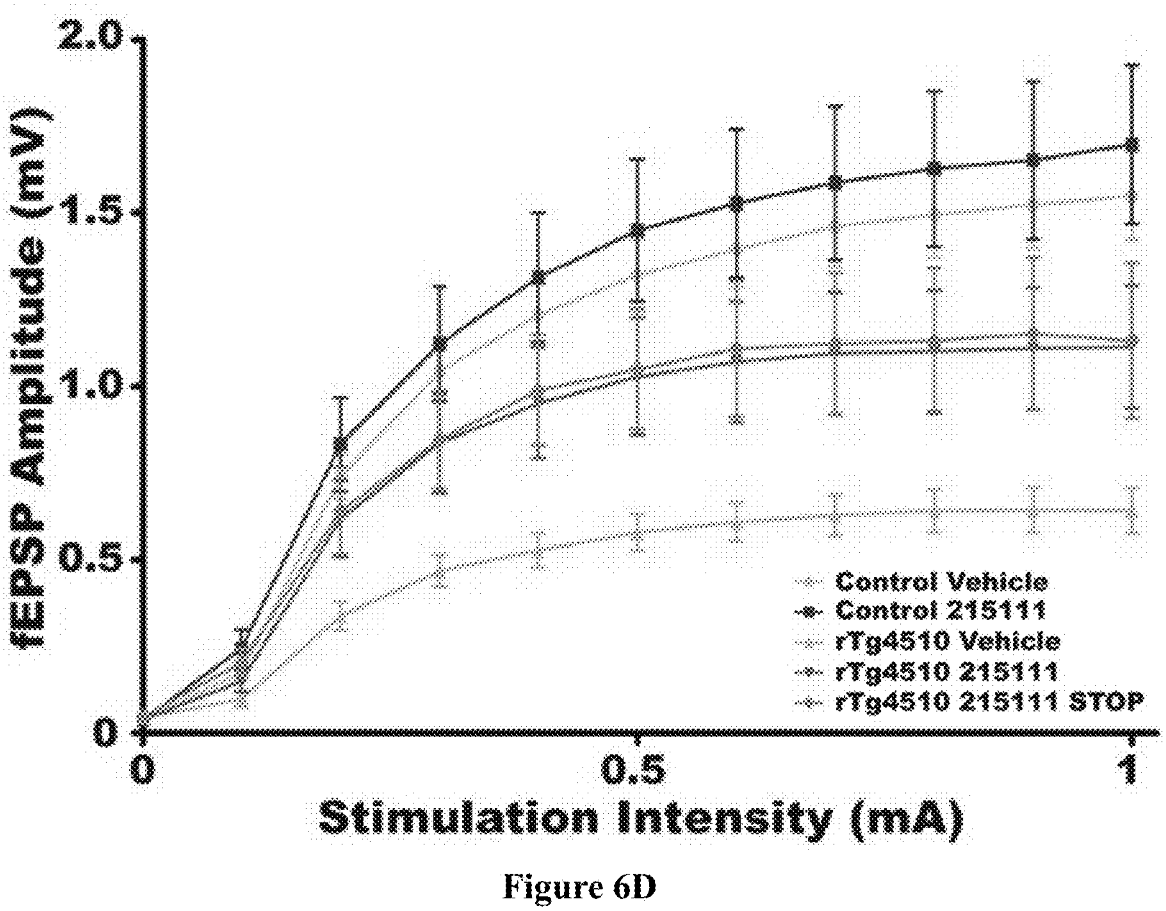
Figure 6E:
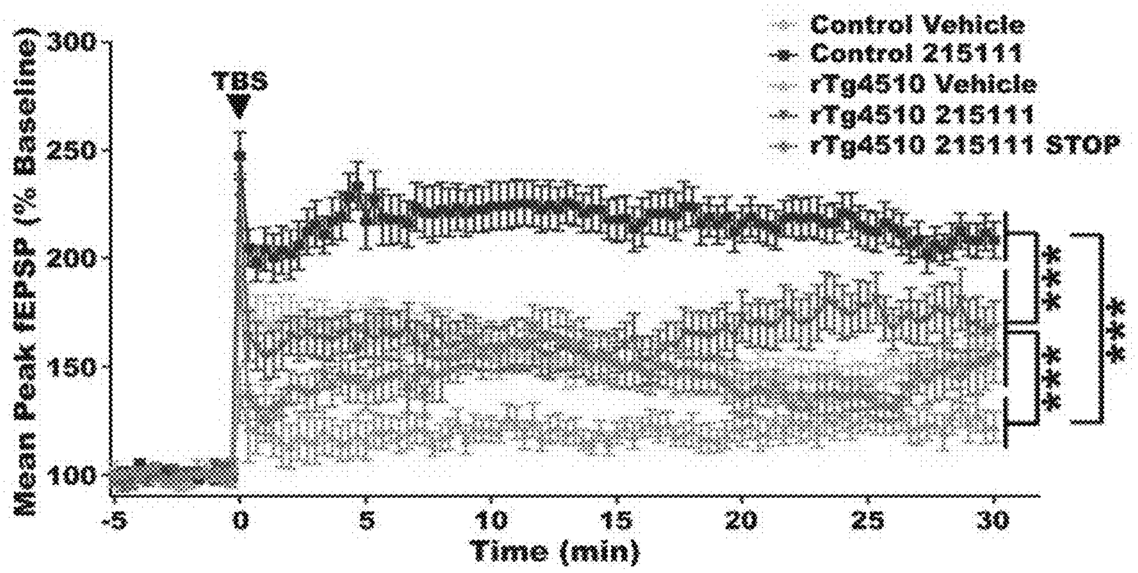

We further conducted electrophysiological studies to examine the integrity of the hippocampal synaptic circuit. We analyzed changes to LTP in the hippocampal CA3-CA1 circuit along the Schaffer collateral pathway. By only looking at the input/output curves, it was clear that all three rTg4510 groups had reduced synaptic strength (FIG. 6D). However, the vehicle rTg4510 group had the most substantially reduced synaptic strength while the continued-treatment and the STOP-treatment groups showed an intermediate reduction. The vehicle rTg4510 group exhibited very little LTP (FIG. 6E). Both STOP-treatment and continued-treatment rTg4510 groups were found to have significantly enhanced LTP relative to the vehicle rTg4510 group that was statistically indistinguishable from the control vehicle group. This is surprising because, although both continued-treatment and STOP-treatment groups exhibited neurodegeneration and reduced synaptic integrity relative to controls, both were able to form relatively normal LTP. Of note, compound-treated controls were found to have highly elevated levels of LTP after stimulation compared to vehicle-treated controls suggesting these mice exhibit enhanced synaptic plasticity. These results indicate that Compound 100's benefits are sustained one-month after treatment cessation.

Figure 7A:
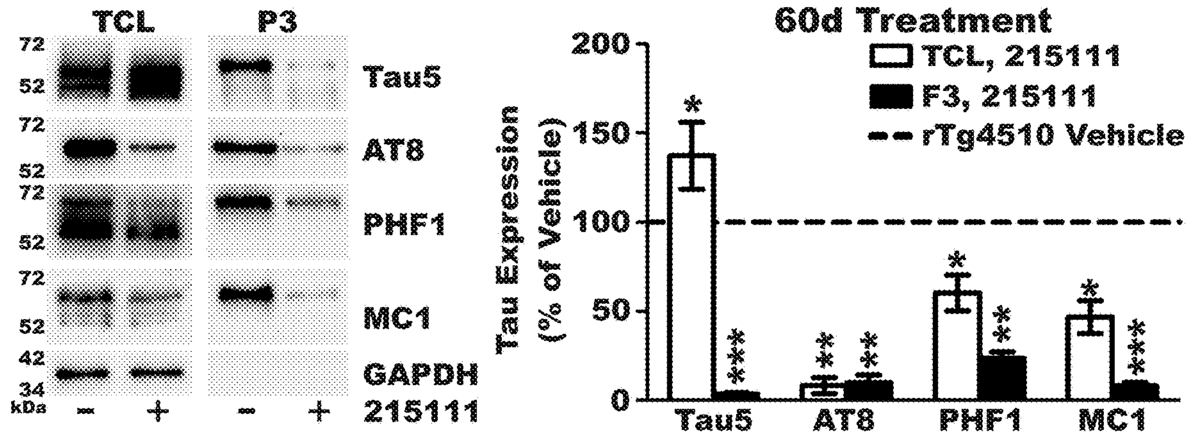
FIGS. 7A-7C show that Compound 100 reduces pTau and inhibits GSK30 in rTg(tauP301L)4510 mice.

As shown in FIG. 4G, we observed reduced neurofibrillary tangles in long-term compound-treated rTg4510 mice. We, therefore, investigated if the compound could reduce toxic forms of tau. We examined tau expression levels in total cell lysates (TCL) and Sarkosyl insoluble fractions (P3) prepared from the forebrains of rTg4510 mice that were harvested at four months old (after two months of treatment) by Western blot analysis. Four antibodies, which recognized different phosphorylation sites or pathological forms of tau, were used: PHF1 recognized Ser 396 & Ser404; AT8 recognized Ser202 & Thr205; MC-1 recognized neurofibrillary tangles and Tau5 recognized all of tau (phosphorylated and non-phosphorylated isoforms). Results showed a robust decrease in the expression of all forms of phosphorylated tau tested in compound-treated rTg4510 samples, both TCL and P3 fractions (FIG. 7A). There was an especially significant reduction in the 64 kDa (hyperphosphorylated) variant for each antibody tested; it has been reported that the 64 kDa variant was strongly correlated with neurodegeneration. Importantly, transgene expression of tau was not negatively affected as there was no reduction in total-tau; rather, a slight increase in the level of total-tau expression was observed, which we attributed to an increased number of surviving neurons.

Figure 7B:
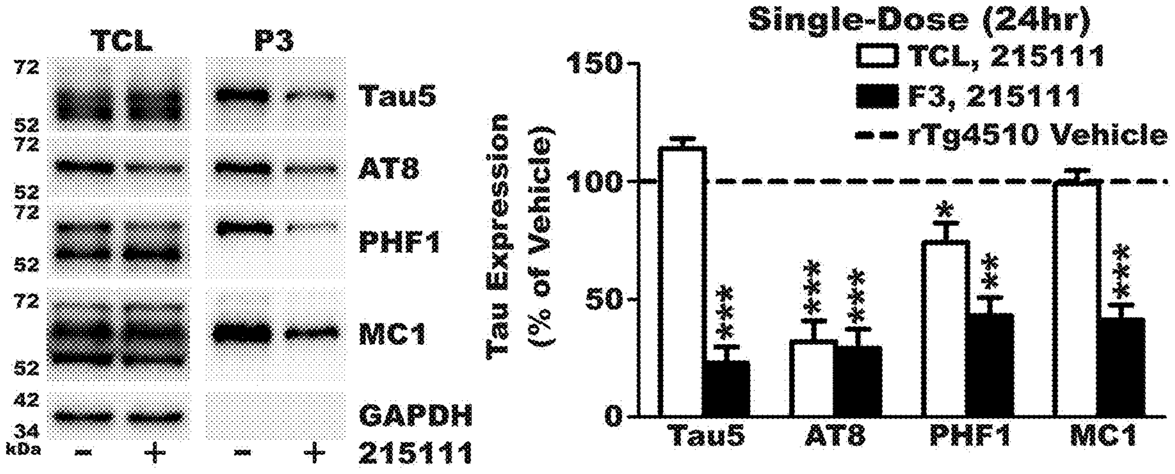
Figure 7C:
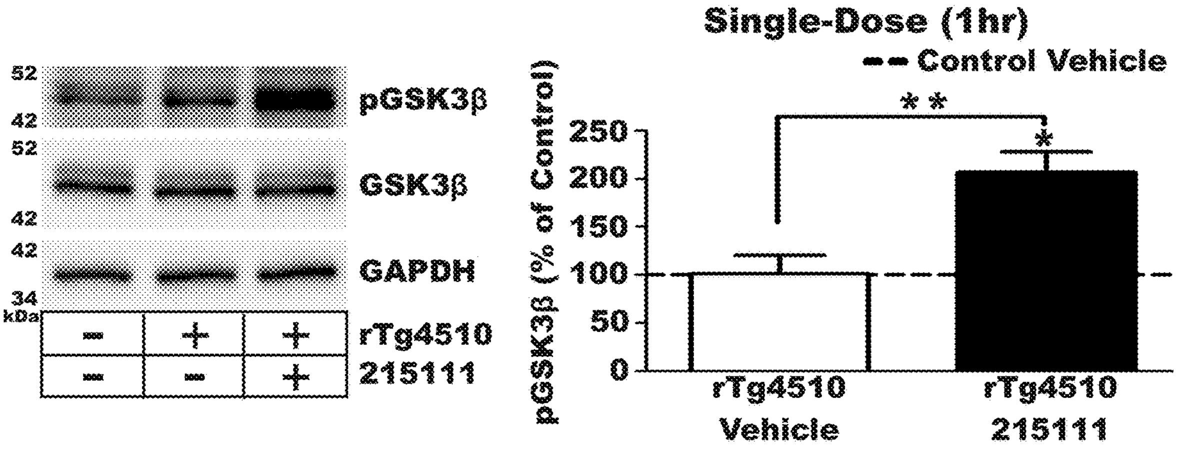

Next, we asked if this reduction in tau phosphorylation and deposition was a direct effect of Compound 100, or due to compensatory changes secondary to long-term compound-treatment. To accomplish this, naïve rTg4510 mice were given a single dose of vehicle or compound 100, and, 24 hours later, forebrains were collected and processed for Sarkosyl isolation. We found that, even after a single dose, there was a significant decrease in pTau (AT8 and PHF1), but no change in total tau (Tau-5) or tau tangles (MC1) in TCL (FIG. 7B). Even more prominently, there was a very clear reduction of all forms of tau in the P3 fraction (FIG. 7B). This indicated a direct effect of compound mediating reduced pTau and suggested that compound may activate/inhibit a kinase/phosphatase to mediate this effect. To identify which kinase/phosphatase is involved, forebrain TCL samples were collected from rTg4510 mice one-hour after a single dose. The phosphorylation (activation) state of kinases that have been reported to target tau as a substrate were assessed. Of all the kinases tested, only GSK30 showed a significant change—two-fold upregulation of phosphorylation at Ser9 (FIG. 7C). This form of phosphorylation inhibits GSK30 activity. Therefore, inactivation of the GSK30 kinase may mediate reduced tau phosphorylation in rTg4510 mice after compound treatment. These results indicate that compound 100 reduces tau hyperphosphorylation/deposition by modifying kinase activity.

In summary, these data demonstrate that Compound 100 exhibits significant beneficial effects in rTg4510 mice (a model for age-related Alzheimer's disease (AD)-like pathologies).

Compound 100 Prevents and Reduces Anxiety, Depression, and Cognitive Problems in a Mouse Model of Gulf War Illness Gulf War illness (GWI) afflicts~30% of the 700,000 military personnel who served in the Persian Gulf War. Central nervous system impairments are the most ubiquitous among the various symptoms of GWI. These mainly comprise of anxiety, depression, and cognitive difficulties. It is widely believed that these clinical symptoms are linked to a combination of exposures encountered by the service personnel. These include significant exposure to pyridostigmine (an anti-nerve gas drug), permethrin (an insecticide), and N,N-diethyl-m-toluamide (DEET; an insect repellant), and war-related stress. Literature indicates that chronic exposure to these GWI-related chemicals and stress results in an increase in extracellular glutamate level and the dyshomeostasis of glutamatergic system in the brain, which may be linked to memory and mood deficits.

We investigated if increased glutamate transporter EAAT2 expression by compound 100 can normalize the dyshomeostasis of the glutamatergic system and subsequently improve cognitive and mood deficits. Three months old C57BL/6J mice were randomly divided into three groups: control (no GWI, with vehicle), GWI with vehicle, and GWI with compound. For GWI groups, mice were exposed to GWI chemicals and chronic unpredictable stress daily for 6 weeks. GWI chemicals include pyridostigmine (1.3 mg/kg), permethrin (0.13 mg/kg), and DEET (40 mg/kg). The stress regimen included exposure to two different stressors each day. The stressors used in this study include restraint, cage rotation, hot stress, cold stress, predator sound, periods of darkness during the light cycle, wet bedding, replace bedding with water, cage tilt at 45 degree angle, and stroboscopic lighting. Mice received either compound 100 (20 mg/kg) or vehicle daily starting from the beginning of 6-weeks exposure. At 3-months post-exposure, mice were subjected to several behavior tests to assess mood and cognitive functions. These tests included dark and light exploration, elevated plus maze, novelty suppressed feeding, tail suspension open field, novel object recognition, and Barnes maze tests.

Figure 8A:
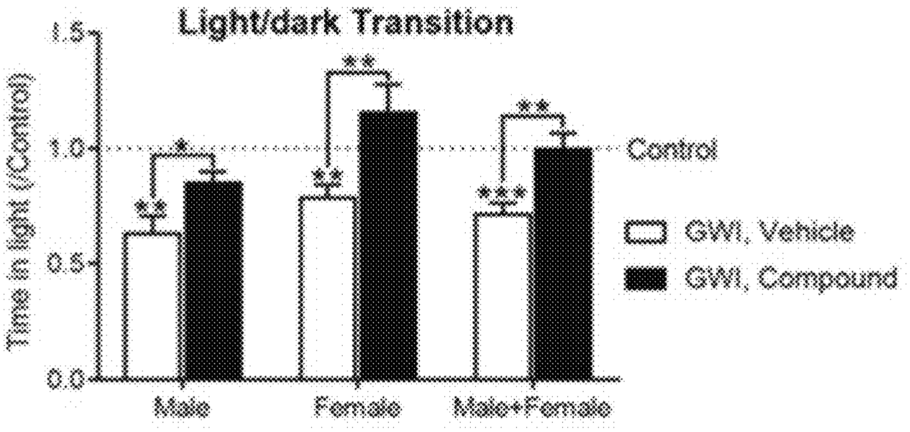
FIGS. 8A-8H show that Compound 100 prevents the development of mood (FIG. 5A-5E) and cognitive (FIGS. 5F-5G) deficits in a mouse model of Gulf War Illness (GWI) (n=15-18/group).
Figure 8B:
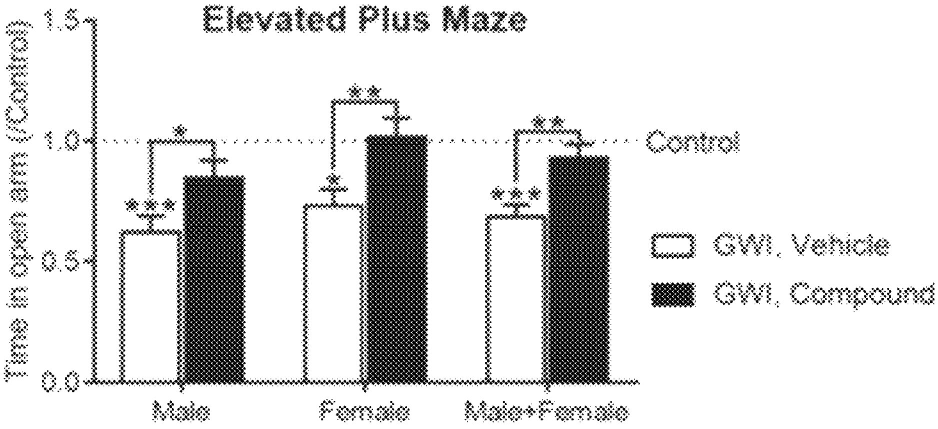
Figure 8C:
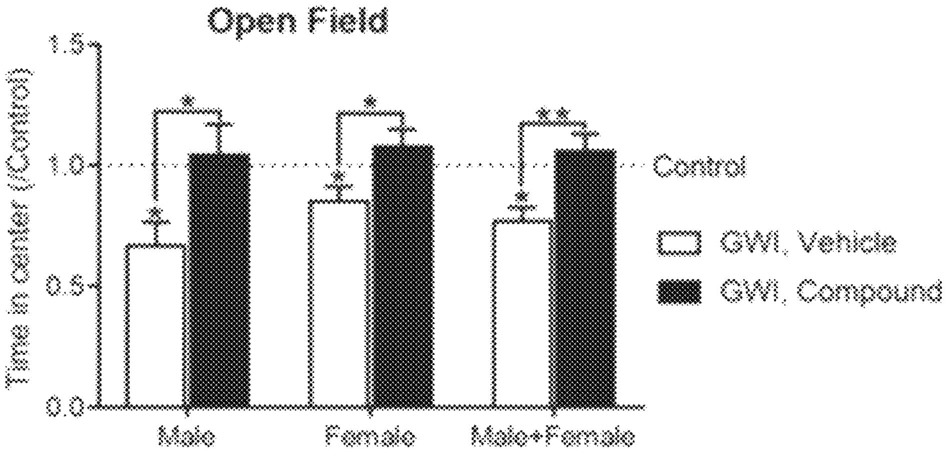
Figure 8D:
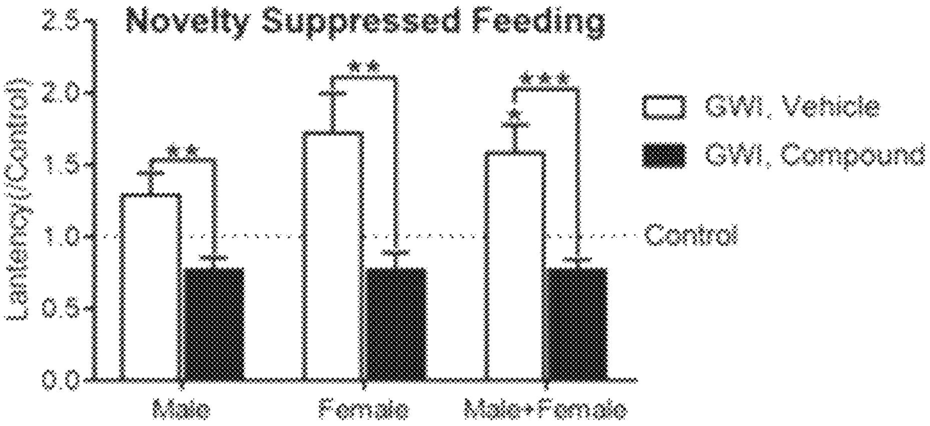
Figure 8E:
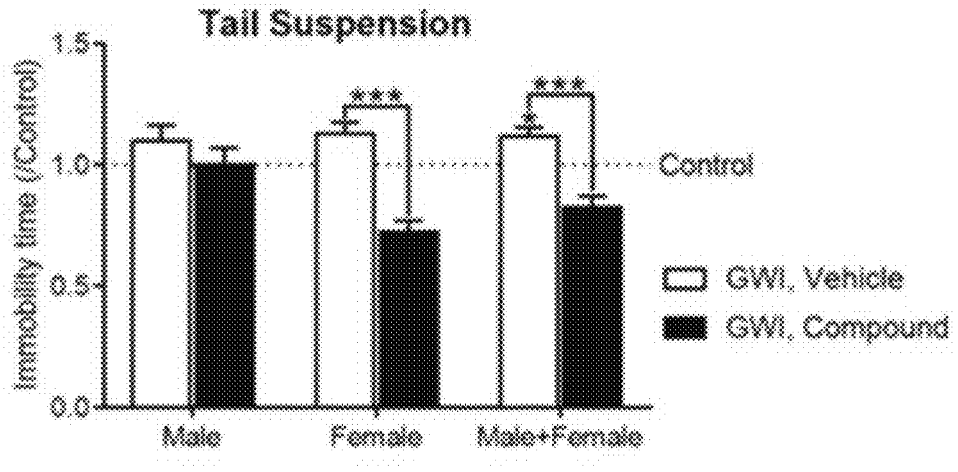
Figure 8F:
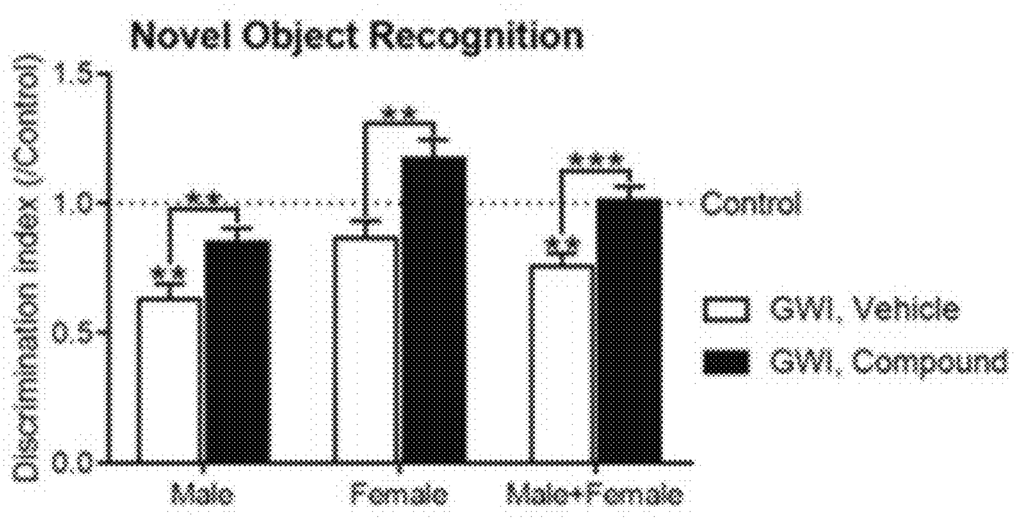
Figure 8G:
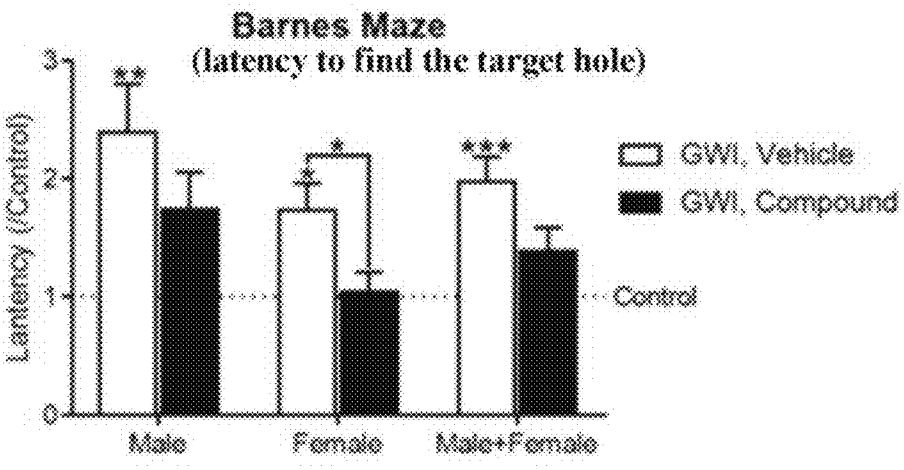
Figure 8H:
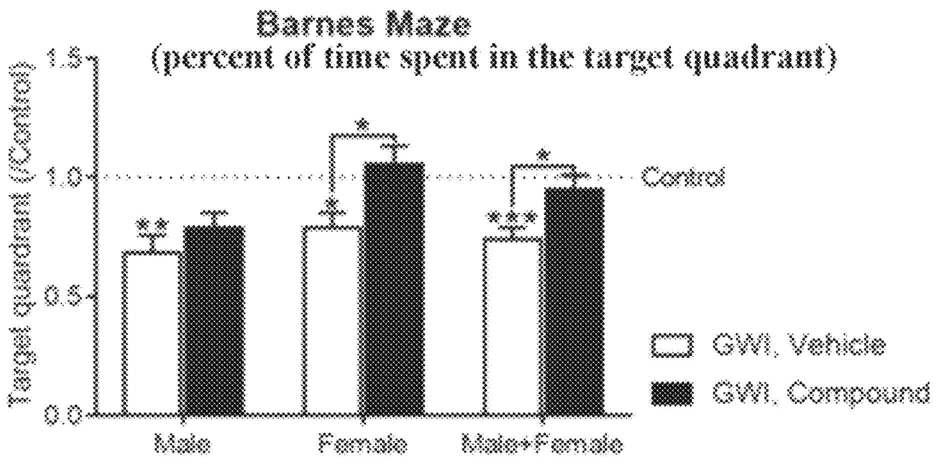

Results showed that GWI conditioned mice developed anxiety- and depression-like behaviors (FIGS. 8A-8E; GWI/vehicle group) and also exhibit a decrease in cognitive functions in these GWI conditioned mice (FIGS. 8F-8H; GWI/vehicle group). Importantly, anxiety- and depression-like behaviors were significantly reduced in the GWI compound-treated mice (FIGS. 8A-8E). Compound-treated mice also demonstrated improved cognitive functions (FIGS. 8F-8H). These results indicate that compound 100 can prevent development of cognitive and mood deficits in GWI mice.

Figure 9A:
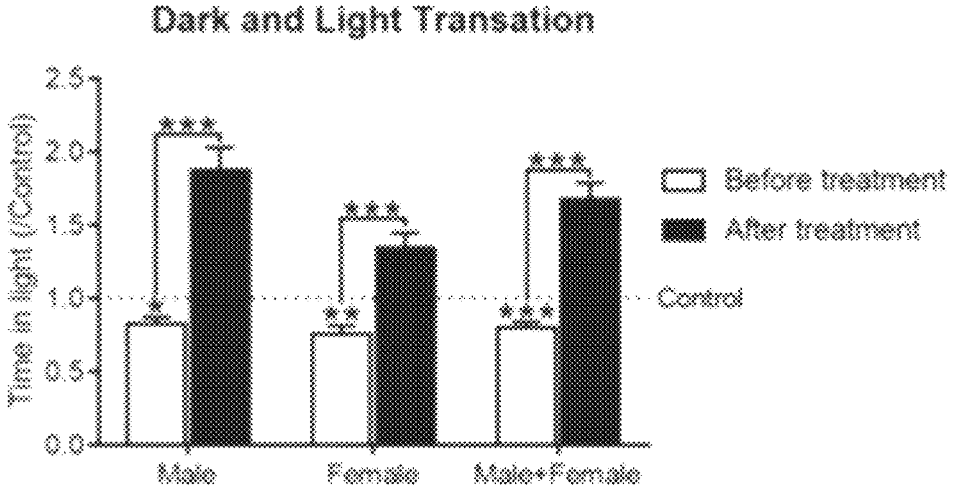
FIGS. 9A-9H show that Compound 100 improves mood (FIGS. 5A-5E) and cognitive (FIGS. 5F-5H) deficits when symptoms are presentin a mouse model of Gulf War illness (n=15-18/group).
Figure 9B:
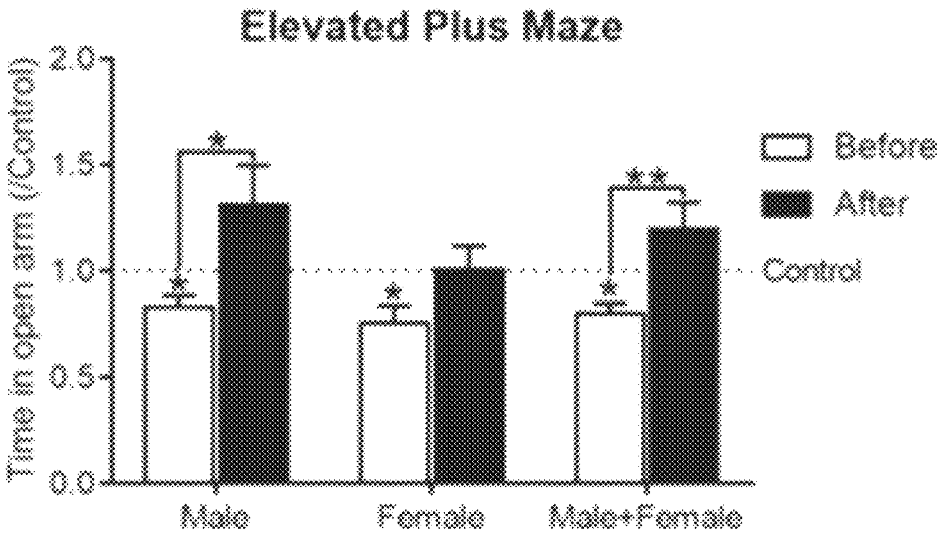
Figure 9C:
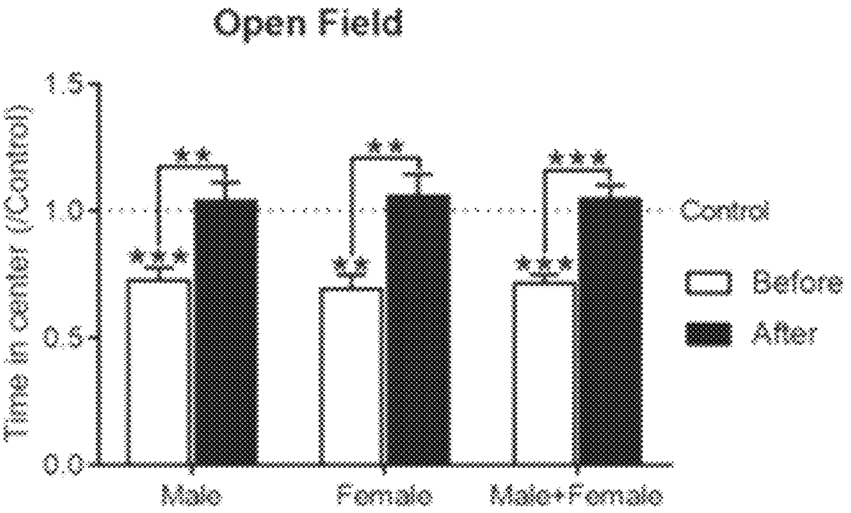
Figure 9D:
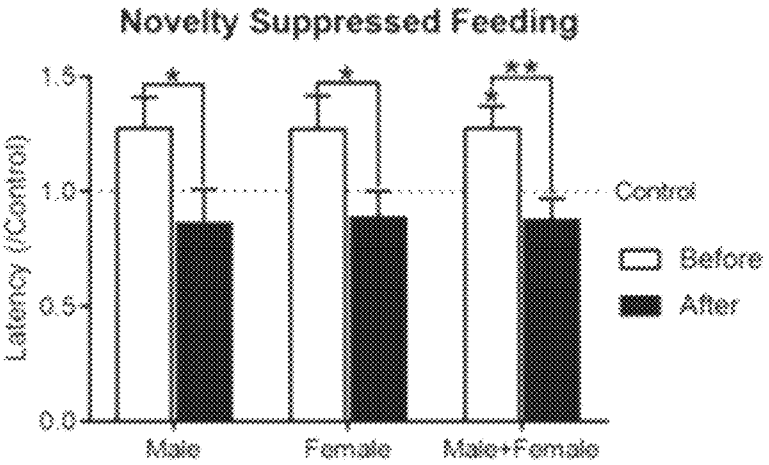
Figure 9E:
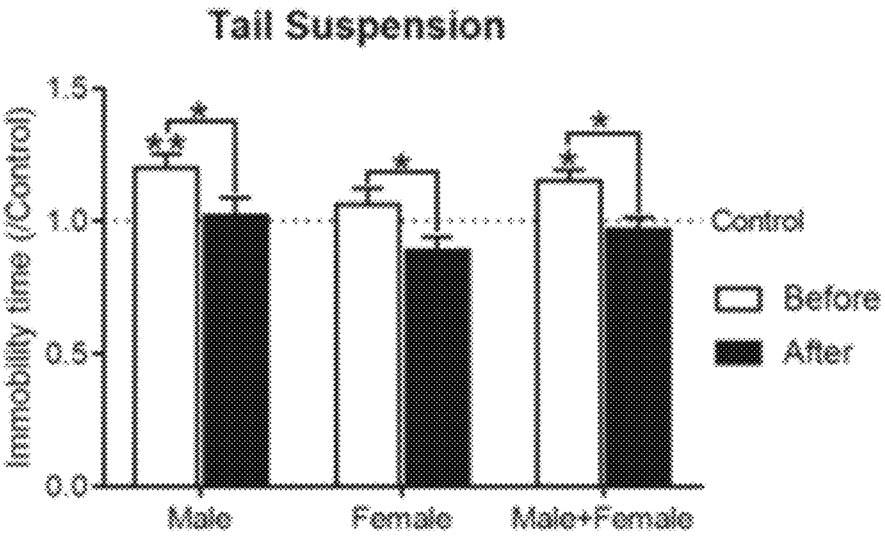
Figure 9F:
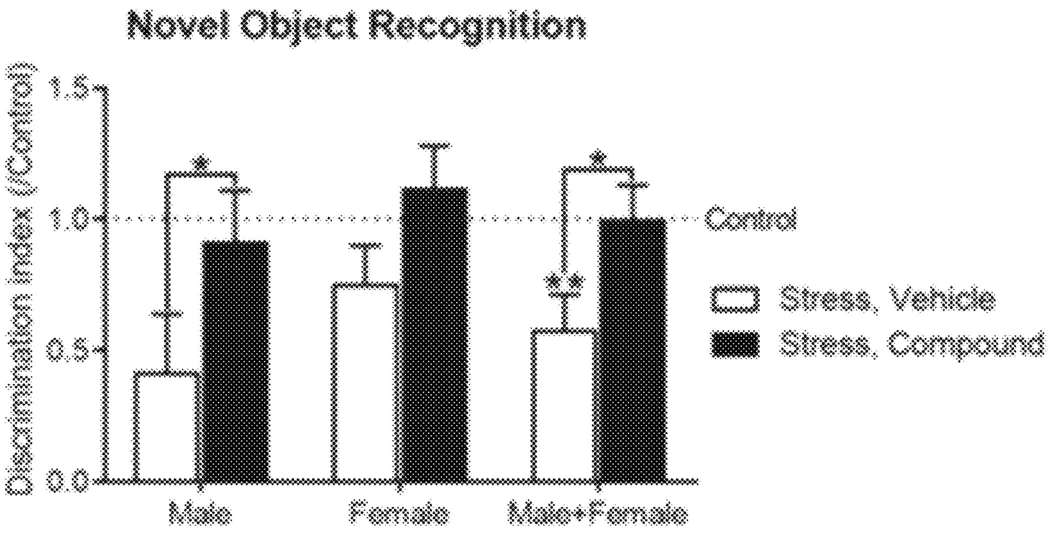
Figure 9G:
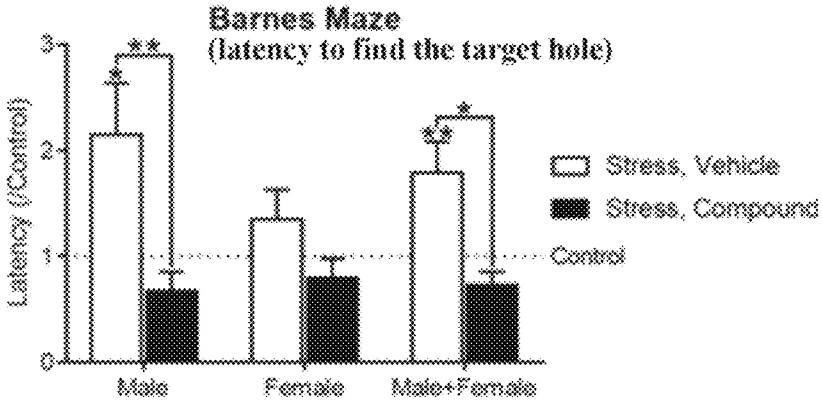
Figure 9H:
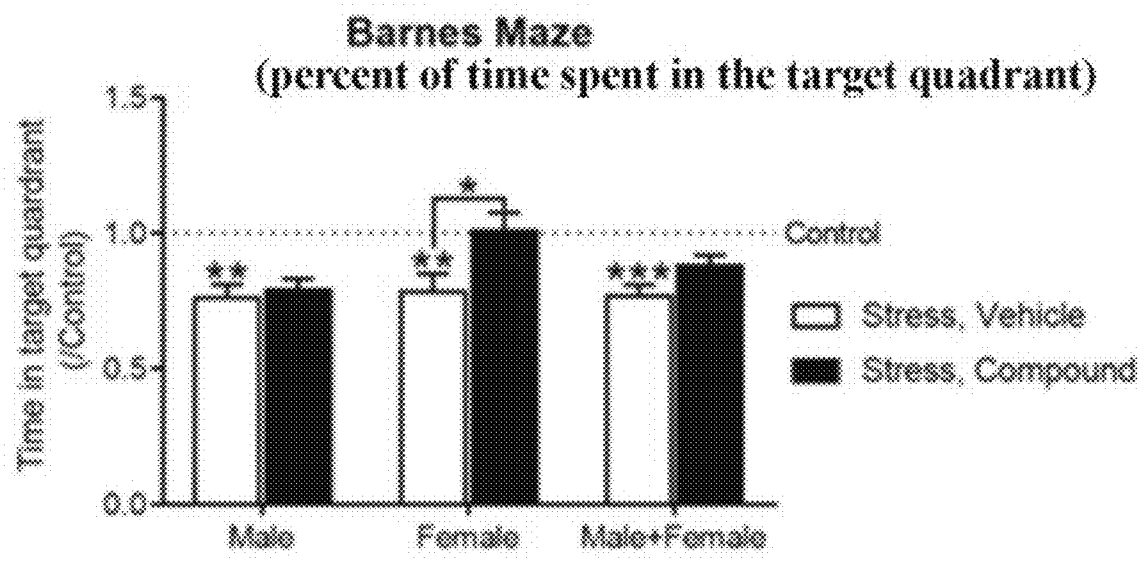

Next, we conducted treatment studies—GWI mice were treated with compound 100 (20 mg/kg) at five months post-exposure when the deficits have developed. After one month of treatment, mice were evaluated for mood and cognitive functions. Results indicated that compound treatment reduced anxiety- and depression-like behaviors (FIGS. 9A-9E). Cognitive functions were also significantly improved (FIGS. 9F-9H). These results indicate that compound 100 is able to reduce mood and cognitive deficits when the symptoms are present.

Figure 10A:
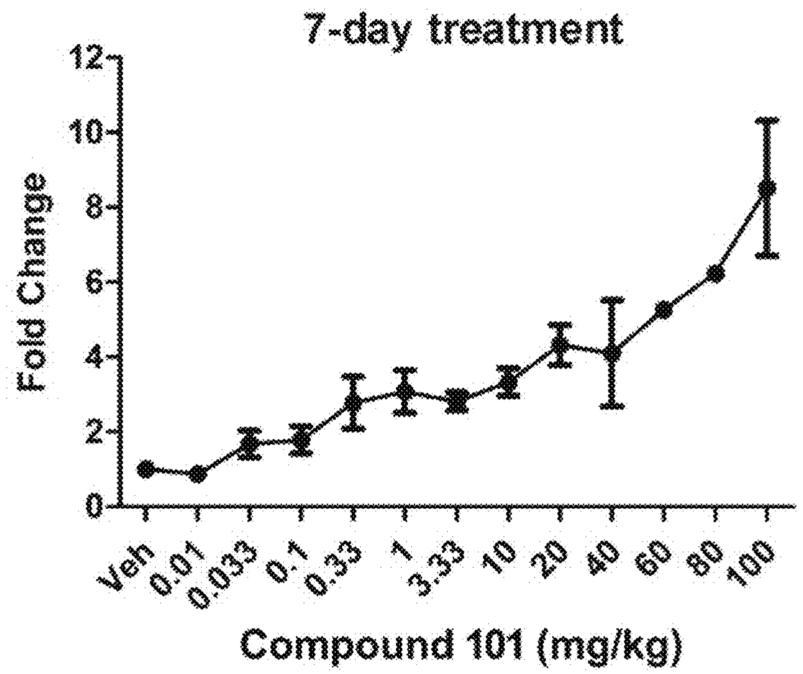
FIGS. 10A-10B show the dose-dependent increase of EAAT2 protein expression in mouse brains after 7-day or 28-day daily treatment with Compound 101 at indicated doses. n=6 for each group.
Figure 10B:
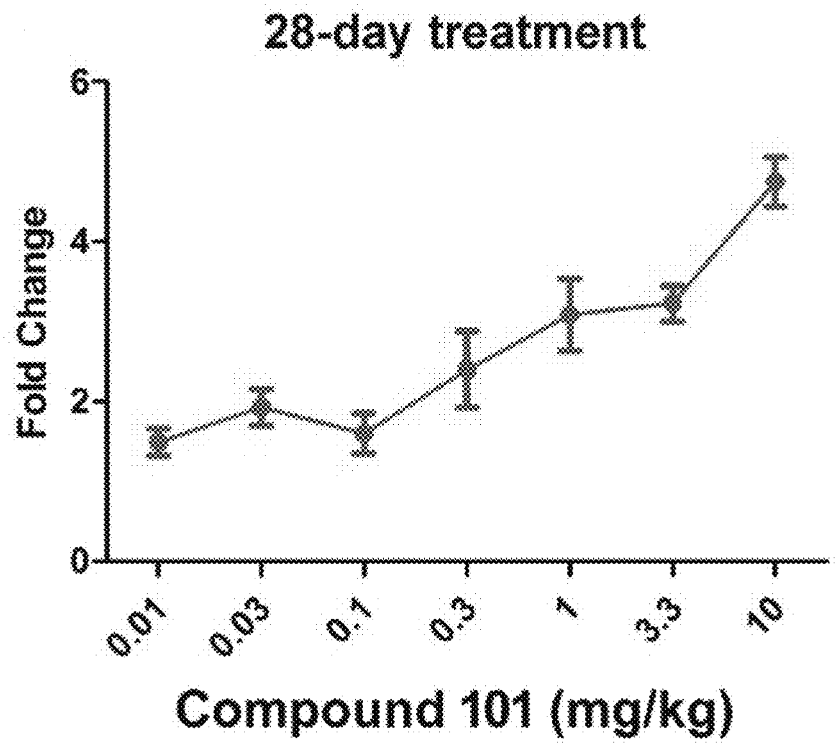
Figure 10C:
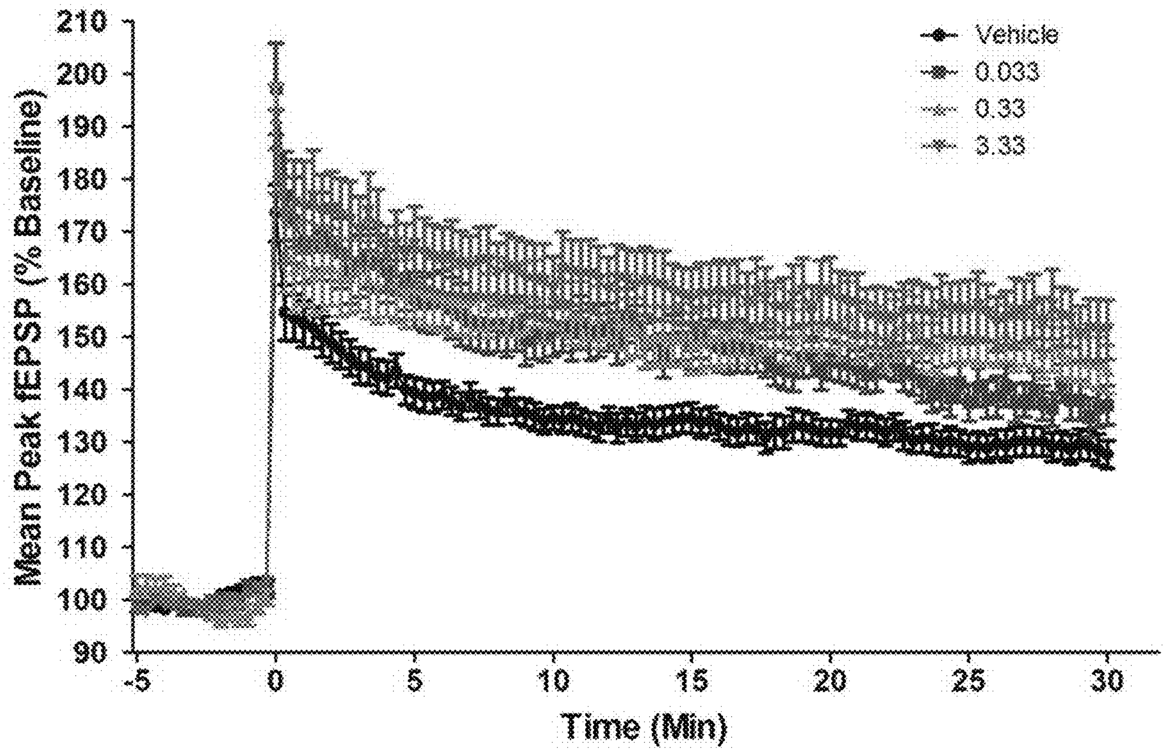
FIG. 10C shows that Compound 101 treatment enhances CA3-CA1 long-term potentiation (LTP) in the hippocampus in a dose-dependent manner. 8-12 slices, 4 animals for each group.

Compound 101 Increases EAAT2 Protein Levels and Enhances Synaptic Plasticity in the Brains of Wild-Type Mice Wild-type C57BL/6 mice (2-3 months old) were treated orally with compound 101 at 0.01, 0.033, 0.1, 0.33, 1, 3.33, 10, 20, 40, 60, and 100 mg/kg/day (voluntary ingestion of compound in honey) for seven or 28 days. Mice then were euthanized and brains were harvested for examining EAAT2 protein levels by Western blot analysis. Results showed that EAAT2 protein levels were dose-dependently increased (FIGS. 10A and 10B). To determine the functional consequences of the increased EAAT2 to the synaptic plasticity, wild-type mice were treated with vehicle or compound 101 at 0.033, 0.33, and 3.3 mg/kg for seven days. Mice were then euthanized and acute hippocampal slices were collected and assessed for changes in long-term potentiation (LTP). As shown in FIG. 10C, field potential recordings from CA1 of compound treated mice showed significantly increased responses to stimulation of CA3 afferents up to 30 min after LTP induction compared to vehicle treated animals (8-12 slices/4 animals for each group). These results indicate that compound treatment increases EAAT2 protein levels and subsequently enhances synaptic plasticity in the hippocampus.

The compounds, compositions, and methods of the appended claims are not limited in scope by the specific compounds, compositions, and methods described herein, which are intended as illustrations of a few aspects of the claims. Any compounds, compositions, and methods that are functionally equivalent are intended to fall within the scope of the claims. Various modifications of the compounds, compositions, and methods in addition to those shown and described herein are intended to fall within the scope of the appended claims. Further, while only certain representative compounds, components, compositions, and method steps disclosed herein are specifically described, other combinations of the compounds, components, compositions, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A compound defined by Formula I

Formula I

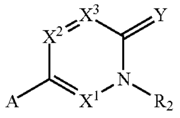

wherein

Y is O;

$X^1$ is N;

$X^2$ is $CR^3$;

$X^3$ is $CR^4$;

A is pyridyl, pyrazinyl, pyrimidinyl, triazinyl, or pyridazinyl substituted by 1, 2, 3, or 4 independently selected $R^A$ groups;

$R^2$ is $—(CHR^E)_nR^5$;

$R^5$ is 5-6 membered heteroaryl optionally substituted by 1 or 2 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently H;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)\ OR^a$, $OC(O)R^b$, $OC(O)NR^cR^d$, $NR^cR^d$, $NR^cOR^d$, $NR^cC(O)R^b$, $NR^cC(O)\ OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl) carbamyl, aminosulfonyl, $C_{1-6}$ alkylaminosulfonyl, and di($C_{1-6}$ alkyl) aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl) aminosulfonylamino, aminocarbonylamino, $C_{1-6}$ alkylaminocarbonylamino, and di($C_{1-6}$ alkyl) aminocarbonylamino; and n is 1;

or a pharmaceutically acceptable salt, ester, or N-oxide thereof.

2. The compound of claim 1, wherein $R^2$ is $—(CH_2)_nR^5$.

3. The compound of claim 1, wherein $R^5$ is pyridyl, pyrazinyl, pyrimidinyl, triazinyl, or pyridazinyl optionally substituted by 1 or 2 independently selected $R^B$ groups.

4. A pharmaceutical composition comprising a compound of claim 1 and a pharmaceutically acceptable excipient.

* * * * *